United States Patent
Bartkovitz et al.

(10) Patent No.: US 8,017,607 B2
(45) Date of Patent: Sep. 13, 2011

(54) N-SUBSTITUTED-PYRROLIDINES AS INHIBITORS OF MDM2-P-53 INTERACTIONS

(75) Inventors: David Joseph Bartkovitz, Nutley, NJ (US); Xin-Jie Chu, Livingston, NJ (US); Jin-Jun Liu, Warren Township, NJ (US); Tina Morgan Ross, Royersford, PA (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/898,974

(22) Filed: Oct. 6, 2010

(65) Prior Publication Data

US 2011/0086854 A1    Apr. 14, 2011

Related U.S. Application Data

(60) Provisional application No. 61/345,626, filed on May 18, 2010, provisional application No. 61/251,413, filed on Oct. 14, 2009.

(51) Int. Cl.
| | |
|---|---|
| *A61K 31/5377* | (2006.01) |
| *A61K 31/402* | (2006.01) |
| *A61K 31/4155* | (2006.01) |
| *A61K 31/496* | (2006.01) |
| *A61K 31/454* | (2006.01) |
| *A61K 31/4025* | (2006.01) |
| *A61K 31/4439* | (2006.01) |
| *C07D 207/16* | (2006.01) |
| *C07D 403/12* | (2006.01) |
| *C07D 403/06* | (2006.01) |
| *C07D 401/12* | (2006.01) |
| *C07D 413/14* | (2006.01) |
| *A61P 35/00* | (2006.01) |

(52) U.S. Cl. ............... 514/235.5; 514/254.13; 514/326; 514/343; 514/381; 514/407; 514/423; 544/131; 544/372; 546/208; 546/278.4; 546/279.1; 548/253; 548/364.1; 548/538

(58) Field of Classification Search ............... None
See application file for complete search history.

(56) References Cited

U.S. PATENT DOCUMENTS

2010/0075948 A1    3/2010 Ding

FOREIGN PATENT DOCUMENTS

| EP | 0 947 511 | 10/1999 |
|---|---|---|
| WO | 0105790 | 1/2001 |
| WO | 2005099687 | 10/2005 |
| WO | 2006091646 | 8/2006 |
| WO | 2007/082805 | 7/2007 |
| WO | 2008005268 | 10/2008 |
| WO | 2010031713 | 3/2010 |

OTHER PUBLICATIONS

Bergel et al., caplus an 1947:20747.*
J. Amer. Chem. Soc. (2005) 127 p. 10130.
Howard C. Ansel, Pharmaceutical Dosage Forms and Drug Delivery Systems, 6th Ed. 1995, pp. 196, 456-457.
International Search Report in Corres. Appl. PCT/EP2010/065159 dated Feb. 28, 2011.

* cited by examiner

*Primary Examiner* — Sun Jae Loewe
(74) *Attorney, Agent, or Firm* — George W. Johnston; Patricia S. Rocha-Tramaloni

(57) ABSTRACT

There are provided compounds of the formula

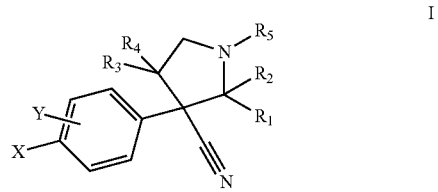

wherein X, Y, $R_1$, $R_2$, $R_3$, $R_3$, $R_4$, and $R_5$ are as described herein
and enantiomers and pharmaceutically acceptable salts and esters thereof which are useful as anticancer agents.

13 Claims, No Drawings

N-SUBSTITUTED-PYRROLIDINES AS INHIBITORS OF MDM2-P-53 INTERACTIONS

PRIORITY TO RELATED APPLICATION(S)

This application claims the benefit of U.S. Provisional Application No. 61/345,626, filed May 18, 2010, and U.S. Provisional Application No. 61/251,413, filed Oct. 14, 2009, which is hereby incorporated by reference in its entirety.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention relates to pyrrolidine-2-carboxamide derivatives I which act as antagonists of mdm2 interactions and hence are useful as potent and selective anticancer agents. The present compounds are of the general formula

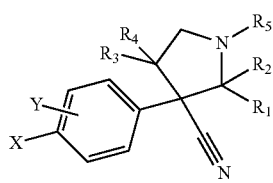

wherein X, Y, $R_1$, $R_2$, $R_3$, $R_4$, and $R_5$ are as described herein and enantiomers and pharmaceutically acceptable salts and esters thereof.

DETAILED DESCRIPTION OF THE INVENTION

There are provided compounds of the formula

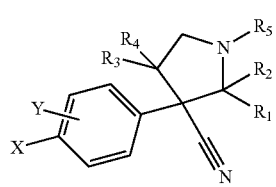

wherein
X is selected from the group consisting of H, F, Cl, Br, I, cyano, nitro, ethynyl, cyclopropyl, methyl, ethyl, isopropyl, vinyl and methoxy,
Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, heteroaryl, heterocycle, COOR', OCOR', CONR'R", NR'COR", NR"SO$_2$R', SO$_2$NR'R" and NR'R" wherein
R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle
and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle,
one of $R_1$ and $R_2$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen
one of $R_3$ and $R_4$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen,
$R_5$ is selected from the group consisting of lower alkyl, substituted lower alkyl, —CH$_2$(CH$_2$)$_n$—CHOH—R', —CH$_2$(CH$_2$)$_n$—CHOH—CH$_2$—(CH$_2$)$_n$—NR'R", CH$_2$(CH$_2$)$_n$—CO(CH$_2$)$_n$NR'R", CO(CH$_2$)$_n$—R', —CO(CH$_2$)$_n$—NR'—(CH$_2$)$_n$—CHOH—R', —CO(CH$_2$)$_n$—NR'R", (CH$_2$)$_n$—NR'SO$_2$R", —COCH$_2$(CH$_2$)$_n$—COOH, (CH$_2$)$_n$—COOR', (CH$_2$)$_n$—CONR'R", —CO(CH$_2$)$_n$—OR', —COCH$_2$(CH$_2$)$_n$—SR', —COCH$_2$(CH$_2$)$_n$—SOR', —COCH$_2$(CH$_2$)$_n$—SO$_2$R', —COCH$_2$(CH$_2$)$_n$—COR', —COCH$_2$(CH$_2$)$_n$—SO$_3$H, —COCH$_2$(CH$_2$)$_n$—SONR'R", —COCH$_2$(CH$_2$)$_n$—SO$_2$NR'R", —COCH$_2$(CH$_2$CH$_2$O)$_n$—(CH$_2$)$_n$—R', —COCH$_2$(CH$_2$CH$_2$O)$_m$—(CH$_2$)$_n$—OH, —COCH$_2$(CH$_2$CH$_2$O)$_m$—(CH$_2$), —OR', —COCH$_2$(CH$_2$CH$_2$O)$_m$—(CH$_2$)$_n$—NR'R", —COCH$_2$(CH$_2$CH$_2$O)$_m$—(CH$_2$)$_n$—NR'COR", —COCH$_2$(CH$_2$CH$_2$O)$_m$—(CH$_2$)$_n$—NR'SO$_2$R", —COCH$_2$(CH$_2$CH$_2$O)$_m$—(CH$_2$)$_n$—COOH, —COCH$_2$(CH$_2$CH$_2$O)$_n$, —(CH$_2$)$_n$—COOR', —COCH$_2$(CH$_2$CH$_2$O)$_m$—(CH$_2$)$_n$—CONR'R", —COCH$_2$(CH$_2$CH$_2$O)$_m$—(CH$_2$)$_n$—SO$_2$R', —COCH$_2$(CH$_2$CH$_2$O)$_m$—(CH$_2$)$_n$—COR', —COCH₂(CH₂CH₂O)ₘ—(CH₂)ₙ—SONR'R", —COCH₂(CH₂CH₂O)ₘ—(CH₂)ₙ—SO₂NR'R", —COCH₂(CH₂)ₚ—(CH₂CH₂O)ₘ—(CH₂)ₙ—R', —COCH₂(CH₂)ₚ—(CH₂CH₂O)ₘ—(CH₂)ₙ—OH, —COCH₂(CH₂)ₚ—(CH₂CH₂O)ₘ—(CH₂)ₙ—OR', —COCH₂(CH₂)ₚ—(CH₂CH₂O)ₘ—(CH₂)ₙ—NR'R", —COCH₂(CH₂)ₚ—(CH₂CH₂O)ₘ—(CH₂)ₙ—NR'COR", —COCH₂(CH₂)ₚ—(CH₂CH₂O)ₘ—(CH₂)ₙ—NR'SO₂R", —COCH₂(CH₂)ₚ—(CH₂CH₂O)ₘ—(CH₂)ₙ—COOH, —COCH₂(CH₂)ₚ—(CH₂CH₂O)ₘ—(CH₂)ₙ—COOR', —COCH₂(CH₂)ₚ—(CH₂CH₂O)ₘ—(CH₂)ₙ—CONR'R", —COCH₂(CH₂)ₚ—(CH₂CH₂O)ₘ—(CH₂)ₙ—SO₂R', —COCH₂(CH₂)ₚ—(CH₂CH₂O)ₘ, —(CH₂)ₙ—COR', —COCH₂(CH₂)ₚ—(CH₂CH₂O)ₘ—(CH₂)ₙ—SONR'R", —COCH₂(CH₂)ₚ—(CH₂CH₂O)ₘ—(CH₂)ₙ—SO₂NR'R", —COCH₂—COR', —COCH₂—SOR' and —COCH₂SO₂R' wherein R' and R" are as above, m, n, and p are independently 0 to 6, and the pharmaceutically acceptable salts and esters thereof.

Preferred are compounds of formula I having a stereochemical structure as shown as formula IA

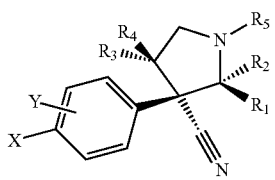

wherein
X is selected from the group consisting of F, Cl and Br,
Y is one to two group(s) independently selected from the group consisting of H, F, Cl, Br, I, CN, OH, nitro, lower alkyl, cycloalkyl and lower alkoxy,
R₁ is hydrogen,
one of R₂ and R₃ is selected from aryl, substituted aryl, heteroaryl or substituted heteroaryl and the other is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl,
R₄ is hydrogen,
R₅ is selected from the group consisting of lower alkyl, substituted lower alkyl, —CH₂(CH₂)ₙ—CHOH—R', —CH₂(CH₂)ₙ—CHOH—CH₂—(CH₂)ₙ—NR'R", —CH₂(CH₂)ₙ—CO(CH₂)ₙNR'R", CO(CH₂)ₙ—R', —CO(CH₂)ₙ—NR'—(CH₂)ₙ—CHOH—R', —CO(CH₂)ₙ—NR'R", (CH₂)ₙ—NR'SO₂R", —COCH₂(CH₂)ₙ—COOH, (CH₂)ₙ—COOR', (CH₂)ₙ—CONR'R", —CO(CH₂)ₙ—OR', —COCH₂(CH₂)ₙ—SR', —COCH₂(CH₂)ₙ—SOR', —COCH₂(CH₂)ₙ—SO₂R', —COCH₂(CH₂)ₙ—COR', —COCH₂(CH₂)ₙ—SO₃H, —COCH₂(CH₂)ₙ—SONR'R", —COCH₂(CH₂)ₙ—SO₂NR'R", —COCH₂(CH₂CH₂O)ₘ—(CH₂)ₙ—R', —COCH₂(CH₂CH₂O)ₘ—(CH₂)ₙ—OH, —COCH₂(CH₂CH₂O)ₘ—(CH₂)ₙ—OR', —COCH₂(CH₂CH₂O)ₘ—(CH₂)ₙ—NR'R", —COCH₂(CH₂CH₂O)ₘ—(CH₂)ₙ—NR'COR", —COCH₂(CH₂CH₂O)ₘ—(CH₂)ₙ—NR'SO₂R", —COCH₂(CH₂CH₂O)ₘ—(CH₂)ₙ—COOH, —COCH₂(CH₂CH₂O)ₘ—(CH₂)ₙ—COOR', —COCH₂(CH₂CH₂O)ₘ—(CH₂)ₙ—CONR'R", —COCH₂(CH₂CH₂O)ₘ—(CH₂)ₙ—SO₂R', —COCH₂(CH₂CH₂O)ₘ—(CH₂)ₙ—COR', —COCH₂(CH₂CH₂O)ₘ—(CH₂)ₙ—SONR'R", —COCH₂(CH₂CH₂O)ₘ—(CH₂)ₙ—SO₂NR'R", —COCH₂(CH₂)ₚ—(CH₂CH₂O)ₘ—(CH₂)ₙ—R', —COCH₂(CH₂)ₚ—(CH₂CH₂O)ₘ—(CH₂)ₙ—OH, —COCH₂(CH₂)ₚ—(CH₂CH₂O)ₘ—(CH₂)ₙ—OR', —COCH₂(CH₂)ₚ—(CH₂CH₂O)ₘ—(CH₂)ₙ—NR'R", —COCH₂(CH₂)ₚ—(CH₂CH₂O)ₘ—(CH₂)ₙ—NR'COR", —COCH₂(CH₂)ₚ—(CH₂CH₂O)ₘ—(CH₂)ₙ—NR'SO₂R", —COCH₂(CH₂)ₚ—(CH₂CH₂O)ₘ—(CH₂)ₙ—COOH, —COCH₂(CH₂)ₚ—(CH₂CH₂O)ₘ—(CH₂)ₙ—COOR', —COCH₂(CH₂)ₚ—(CH₂CH₂O)ₘ—(CH₂)ₙ—CONR'R", —COCH₂(CH₂)ₚ—(CH₂CH₂O)ₘ—(CH₂)ₙ—SO₂R', —COCH₂(CH₂)ₚ—(CH₂CH₂O)ₘ—(CH₂)ₙ—COR', —COCH₂(CH₂)ₚ—(CH₂CH₂O)ₘ—(CH₂)ₙ—SONR'R", —COCH₂(CH₂)ₚ—(CH₂CH₂O)ₘ—(CH₂)ₙ—SO₂NR'R", —COCH₂—COR', —COCH₂—SOR' and —COCH₂SO₂R'

R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, m, n, and p are independently 0 to 6 and the pharmaceutically acceptable salts and esters and enantiomers thereof.

Further preferred are compounds shown as formula IB wherein:

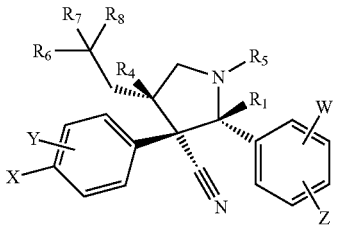

X is F, Cl or Br
Y is a mono substituting group consisted of H or F
Z is F, Cl or Br,
W is H, F or Cl
R₁ is H
R₄ is H
R₅ is selected from the group consisting of lower alkyl, substituted lower alkyl, —CH₂(CH₂)ₙ—CHOH—R', —CH₂(CH₂)ₙ—CHOH—CH₂—(CH₂)ₙ—NR'R", —CH₂(CH₂)ₙ—CO(CH₂)ₙNR'R", CO(CH₂)ₙ—R', —CO(CH₂)ₙ—NR'—(CH₂)ₙ—CHOH—R', —CO(CH₂)ₙ—NR'R", (CH₂)ₙ—NR'SO₂R", —COCH₂(CH₂)ₙ—COOH, (CH₂)ₙ—COOR', (CH₂)ₙ—CONR'R", —CO(CH₂)ₙ—OR', —COCH₂(CH₂)ₙ—SR', —COCH₂(CH₂)ₙ—SOR', —COCH₂(CH₂)ₙ—SO₂R', —COCH₂(CH₂)ₙ—COR', —COCH₂(CH₂)ₙ—SO₃H, —COCH₂(CH₂)ₙ—SONR'R", —COCH₂(CH₂)ₙ—SO₂NR'R", —COCH₂(CH₂CH₂O)ₘ—(CH₂)ₙ—R', —COCH₂(CH₂CH₂O)ₘ—(CH₂)ₙ—OH, —COCH₂(CH₂CH₂O)ₘ—(CH₂)ₙ—OR', —COCH₂(CH₂CH₂O)ₙ, —(CH₂)ₙ—NR'R", —COCH₂(CH₂CH₂O)ₘ—(CH₂)ₙ—NR'COR", —COCH₂(CH₂CH₂O)ₘ—(CH₂)ₙ—NR'SO₂R", —COCH₂(CH₂CH₂O)ₘ—(CH₂)ₙ—COOH, —COCH₂(CH₂CH₂O)ₘ—(CH₂)ₙ—COOR', —COCH₂(CH₂CH₂O)ₘ—(CH₂)ₙ—CONR'R", —COCH₂(CH₂CH₂O)ₘ—(CH₂)ₙ—

SO₂R', —COCH₂(CH₂CH₂O)ₘ—(CH₂)ₙ—COR',
—COCH₂(CH₂CH₂O)ₘ—(CH₂)ₙ—SONR'R", —COCH₂
(CH₂CH₂O)ₘ—(CH₂)ₙ—SO₂NR'R", —COCH₂(CH₂)ₚ—
(CH₂CH₂O)ₘ—(CH₂)ₙ—R', —COCH₂(CH₂)ₚ—
(CH₂CH₂O)ₘ—(CH₂)ₙ—OH, —COCH₂(CH₂)ₚ—
(CH₂CH₂O)ₘ—(CH₂)ₙ—OR', —COCH₂(CH₂)ₚ—
(CH₂CH₂O)ₘ—(CH₂)ₙ—NR'R", —COCH₂(CH₂)ₚ—
(CH₂CH₂O)ₘ—(CH₂)ₙ—NR'COR", —COCH₂(CH₂)ₚ—
(CH₂CH₂O)ₘ—(CH₂)ₙ—NR'SO₂R", —COCH₂(CH₂)ₚ—
(CH₂CH₂O)ₘ—(CH₂)ₙ—COOH, —COCH₂(CH₂)ₚ—
(CH₂CH₂O)ₘ—(CH₂)ₙ—COOR', —COCH₂(CH₂)ₚ—
(CH₂CH₂O)ₘ—(CH₂)ₙ—CONR'R", —COCH₂(CH₂)ₚ—
(CH₂CH₂O)ₘ—(CH₂)ₙ—SO₂R', —COCH₂(CH₂)ₚ—
(CH₂CH₂O)ₘ—(CH₂)ₙ—COR', —COCH₂(CH₂)ₚ—
(CH₂CH₂O)ₘ—(CH₂)ₙ—SONR'R", —COCH₂(CH₂)ₚ—
(CH₂CH₂O)ₘ—(CH₂)ₙ—SO₂NR'R", —COCH₂—COR',
—COCH₂—SOR' and —COCH₂SO₂R', R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, m, n, and p are independently 0 to 6, $R_6$, $R_7$ are both methyl, or linked to form cyclopropyl, cyclobutyl, cyclopentyl or cyclohexyl, $R_8$ is $(CH_2)_q$—$R_9$, q is 0, 1 or 2

$R_9$ is selected from hydrogen, hydroxyl, lower alkyl, lower alkoxy, lower cycloalkyl, aryl, substituted aryl. heteroaryl, substituted heteroaryl, heterocycle or substituted heterocycle, and the pharmaceutically acceptable salts and esters and enantiomers thereof.

Especially preferred are compounds shown as formula IC

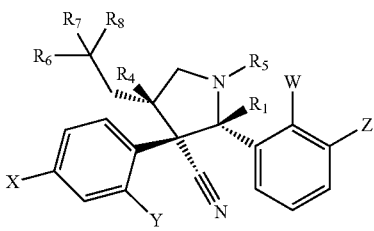

IC wherein

X is F, Cl or Br,

Y is a mono substituting group consisted of H or F,

Z is F, Cl or Br,

W is H, F, $R_1$ is H, $R_4$ is H, $R_5$ is selected from the group consisting of —CO(CH₂)ₙ—R', —CO(CH₂)ₙ—NR'R", (CH₂)ₙ—CONR'R", —CH₂(CH₂)ₙ—CHOH—R', —CH₂(CH₂)ₙ—CHOH—CH₂—(CH₂)ₙ—NR'R", CH₂(CH₂)ₙ—CO(CH₂)ₙNR'R", CO(CH₂)ₙ—R', —CO(CH₂)ₙ—NR'—(CH₂)ₙ—CHOH—R', and —CO(CH₂)ₙ—NR'R", n is 0, 1 or 2, R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle, and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, $R_6$, $R_7$ are both methyl, or linked to form cyclopropyl, cyclobutyl, cyclopentyl or cyclohexyl, $R_8$ is $(CH_2)_q$—$R_9$, q is 0, 1 or 2

$R_9$ is selected from hydrogen, hydroxyl, lower alkyl, lower alkoxy, cycloalkyl, aryl, substituted aryl. heteroaryl, substituted heteroaryl, heterocycle or substituted heterocycle, and the pharmaceutically acceptable salts and esters thereof.

Especially preferred are compounds selected from the group consisting of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide, (2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide, rac-(2S,3S,4S)-2-(3-chloro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid [1-(2-hydroxy-2-methyl-propyl)-1H-pyrazol-3-yl]-amide, rac-(2S,3S,4S)-2-(3-chloro-2-fluoro-phenyl)-3-(4-chloro-2-fluoro-phenyl)-4-(2,2-dimethyl-propyl)-1-(4-ethyl-piperazine-1-carbonyl)-pyrrolidine-3-carbonitrile, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (piperidin-4-ylmethyl)-amide, rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-benzoic acid, 4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-methyl)-benzoic acid, rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-benzoic acid, 4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-benzoic acid, rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid, rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid, rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-chloro-phenyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-fluoro-phenyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid 4-chloro-benzylamide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid [3-(1H-tetrazol-5-yl)-phenyl]-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-cyano-phenyl)-amide,
rac-(2S,3S,4S)-2-(3-chloro-2-fluoro-phenyl)-3-(4-chloro-2-fluoro-phenyl)-1-(4-cyano-benzoyl)-4-(2,2-dimethyl-propyl)-pyrrolidine-3-carbonitrile,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-carbamoyl-phenyl)-amide,
rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzamide,
rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-2-oxo-ethyl}-2-ethoxy-benzoic acid,
rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-4-oxo-butyl}-benzoic acid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid 4-fluoro-benzylamide,
rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propenyl}-benzoic acid,
rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propionic acid,
rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]acetic acid tert-butyl ester,
rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid,
rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid methyl ester
rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid,
rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzamide,
rac-2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-N—((S)-3,4-dihydroxy-butyl)-acetamide,
rac-(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carboxylic acid ((S)-3,4-dihydroxy-butyl)-amide,
rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl]amino}-benzoic acid ethyl ester,
rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl]-amino}-benzoic acid.
rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid,
rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-benzoic acid methyl ester,
rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-benzoic acid,
rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid methyl ester,
rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid,
rac-2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-N—((S)-3,4-dihydroxy-butyl)-acetamide,
rac-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]acetic acid ethyl ester,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid pyridin-4-ylamide,
rac-2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid methyl ester,
rac-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid,
2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-fluoro-phenyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methylsulfanyl-phenyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methanesulfonyl-phenyl)-amid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid pyridin-3-ylamide,
rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-butyric acid ethyl ester,
rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-carbamoyl-propyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methylcarbamoyl-propyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (1-methanesulfonyl-piperidin-4-yl)-amide,
rac-2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]acetamide,
rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid ethyl ester,
rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid methylcarbamoylmethyl-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid carbamoylmethyl-amide,
rac-(2S,3S,4S)-2-(3-chloro-2-fluoro-phenyl)-3-(4-chloro-2-fluoro-phenyl)-4-(2,2-dimethyl-propyl)-1-(pyridine-3-sulfonyl)-pyrrolidine-3-carbonitrile,
rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid methyl ester,
rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid,
rac-(2S,3S,4S)-2-(3-chloro-2-fluoro-phenyl)-3-(4-chloro-2-fluoro-phenyl)-4-(2,2-dimethyl-propyl)-1-(6-morpholin-4-yl-pyridine-3-sulfonyl)-pyrrolidine-3-carbonitrile,
rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-2-methoxy-benzoic acid methyl ester,
rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid,
rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-propionic acid ethyl Ester,
rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-propionic acid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-methylcarbamoyl-ethyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-dimethylcarbamoyl-ethyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-carbamoyl-ethyl)-amide,
rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid ethyl ester,
rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid,
rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-propionic acid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (6-chloro-pyridin-3-ylmethyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (6-chloro-pyridin-3-yl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (1-methyl-2-oxo-1,2-dihydro-pyridin-4-yl)-amide,
rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-sulfonyl]-benzoic acid,
rac-(2S,3S,4S)-2-(3-chloro-2-fluoro-phenyl)-3-(4-chloro-2-fluoro-phenyl)-1-(6-chloro-pyridine-3-sulfonyl)-4-(2,2-dimethyl-propyl)-pyrrolidine-3-carbonitrile,
rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-sulfonyl)-pyrrolidine-3-carbonitrile,
rac-(2S,3S,4S)-2-(3-chloro-2-fluoro-phenyl)-3-(4-chloro-2-fluoro-phenyl)-1-(6-chloro-pyridine-3-carbonyl)-4-(2,2-dimethyl-propyl)-pyrrolidine-3-carbonitrile,
rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-carbonyl)-pyrrolidine-3-carbonitrile,
rac-(2S,3S,4S)-2-(3-chloro-2-fluoro-phenyl)-3-(4-chloro-2-fluoro-phenyl)-4-(2,2-dimethyl-propyl)-1-(1-methyl-6-oxo-1,6-dihydro-pyridine-3-carbonyl)-pyrrolidine-3-carbonitrile,
rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid methyl ester,
rac-4-(((2S,3S,4S)-2-(3-chloro-2-fluorophenyl)-3-(4-chloro-2-fluorophenyl)-3-cyano-4-neopentylpyrrolidine-1-carboxamido)methyl)-2-methoxybenzoic acid,
rac-(2R,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid benzylamide,
rac N-[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-benzamide,
chiral 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid,
chiral 4-({[(2R,3R,4R)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid,
4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid methyl ester,
rac 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid,
chiral 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid, chiral 4-({[(2R,3R,4R)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid and 4-{[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-2-methyl-benzoic acid.

TERMS & DEFINITIONS

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl) or lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the aryl, heteroaryl and heterocycle rings are halogen, lower alkoxy, lower alkyl and amino.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I and II as well as their salts that have at least one asymmetric carbon atom may be present as racemic mixtures or different stereoisomers. The various isomers can be isolated by known separation methods, e.g., chromatography.

Compounds disclosed herein and covered by formula I and II above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

The compounds of the present invention are useful in the treatment or control of cell proliferative disorders, in particular oncological disorders. These compounds and formulations containing said compounds may be particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"IC50" refers to the concentration of a particular compound required to inhibit 50% of a specific measured activity. $IC_{50}$ can be measured, inter alia, as is described subsequently.

Synthetic Methods

The present invention provides methods for the synthesis of N-substituted pyrrolidines. The compounds of the invention can be prepared by processes known in the art. Suitable processes for synthesizing these compounds are provided in the examples.

Compounds of this invention can be synthesized according to the following general schemes. The key transformation is a convergent [2+3] cycloaddition of imine II and activated olefin III to generate pyrrolidine-3-carbonitrile compounds IV in a stereoselective manner.

The starting materials are either commercially available or can be synthesized by methods known to those of ordinary skill in the art. Preparations of intermediates II and III are illustrated in Scheme 1 and 2. In general an appropriately selected aldehyde or ketone can be reacted with methyl amine or C-trimethylsilanyl-methylamine in $CH_2Cl_2$ to generate imines IIa or IIb and were used as crude products without purification (Scheme 1).

Scheme 1

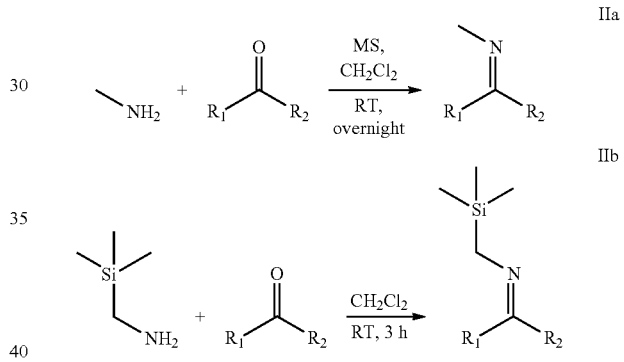

An intermediate of formula III can be made from a base-catalyzed condensation reaction of appropriately selected substituted-phenyl acetonitrile and aldehyde or ketone. The reaction proceeds in a highly regioselective manner with Z-isomer as the major or exclusive product.

Scheme 2

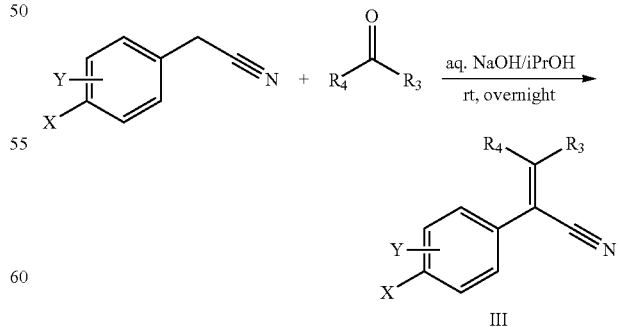

As illustrated in Scheme 3, pyrrolidine of formula IV can be made from of intermediates IIa or IIb, and III by a base catalyzed 1,3-dipolar cycloaddition reaction. The [2+3] cycloaddition reactions of azomethine ylides 1,3-dipoles with olefinic dipolarophiles to form pyrrolidine ring formation have been described in published procedures.

Scheme 3

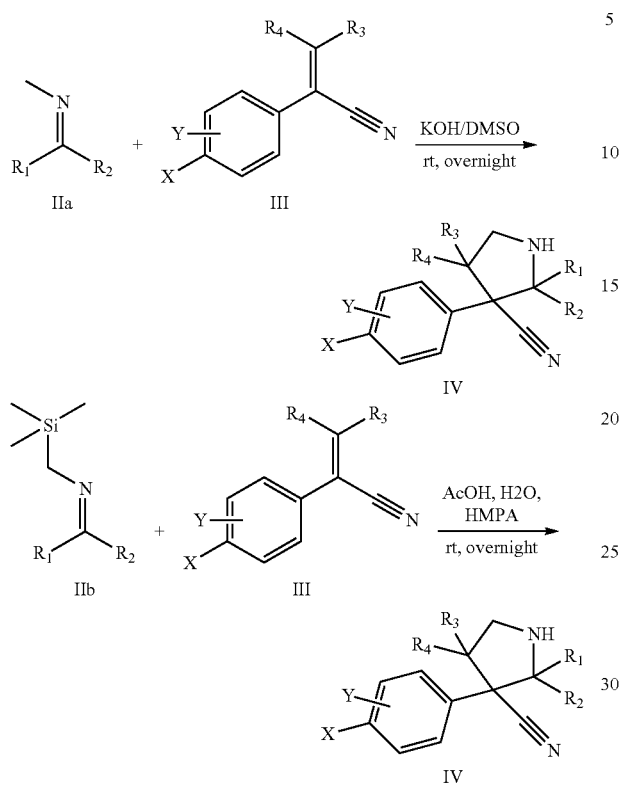

Formula IV is subsequently converted to a) formula VI either through intermediate V or by reacting with isocyanate; b) formula VII by amide formation with various acids using HATU as the coupling reagent; c) formula IX via intermediate VIII followed by amide formation with various amines (Scheme 4). The amide formation from IV to VII or VIII to IX can also be achieved under other conditions using EDCI and HOBt or oxalyl chloride as the coupling reagent to activate the acid V.

Scheme 4

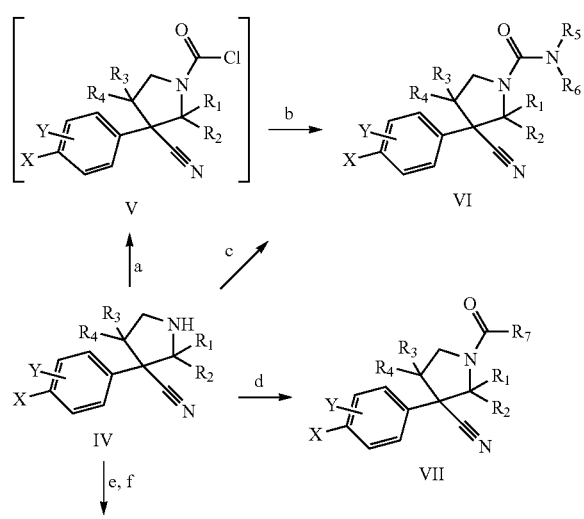

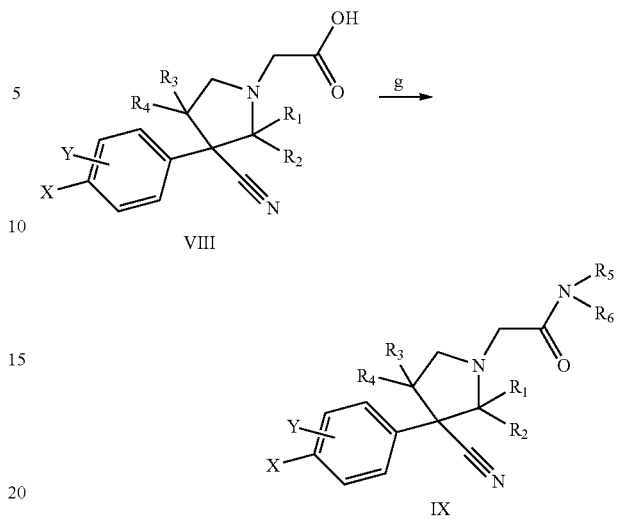

Reagents and conditions: (a) COCl$_2$/TEA/CH$_2$Cl$_2$, rt, 5 min; (b) HNR$_5$R$_6$/TEA/CH$_2$Cl$_2$, rt, 30 min; (c) R$_5$N═C═O/CH$_2$Cl$_2$, rt, 2 hrs; (d) R$_7$COOH/HATU/iPr$_2$NEt/CH$_2$Cl$_2$, rt 2 hrs, or R$_7$COCl/iPr$_2$NEt/CH$_2$Cl$_2$, rt 2 hrs; (e) BrCH$_2$COOtBu/Cs$_2$CO$_3$/DMF, rt, overnight; (f) TFA/CH$_2$Cl$_2$, rt, 3 hrs; (g) HNR$_5$R$_6$/HATU/iPr$_2$NEt/CH$_2$Cl$_2$, rt, 30 min The pyrrolidine compounds I, VI, VII and IX are prepared initially as a racemic mixture and can be chirally separated using chiral Super Fluid Chromatography (SFC) or chiral HPLC or chiral column chromatography. For example, racemic mixture of formula I can be readily resolved into two optically pure or enriched chiral enantiomers Ia and Ib by separation using SFC. (Scheme 5).

Scheme 5

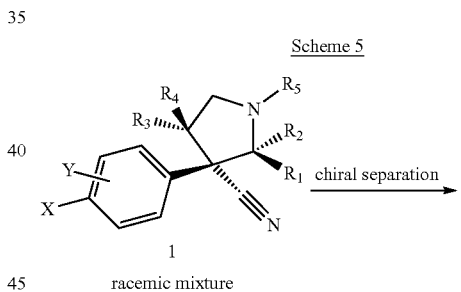

EXAMPLES

The compounds of the present invention may be synthesized according to known techniques. The following examples and references are provided to aid the understanding of the present invention, the true scope of which is set forth in the appended claims.

Example 1a

Preparation of intermediate [1-(3-chloro-2-fluoro-phenyl)-meth-(E)-ylidene]-methyl-amine

M. W. 171.6  C₈H₇FClN

A mixture of 3-chloro-2-fluoro-benzoaldehyde (Oakwood, 97%) (1.59 g, 10.0 mmol) and methyl amine (2.0 M in THF, Aldrich, 7.5 mL, 15.0 mmol) in CH₂Cl₂ (20 mL) was stirred at rt overnight. The reaction mixture was concentrated and the residue was dried under reduced pressure to afford [[1-(3-chloro-2-fluoro-phenyl)-meth-(E)-ylidene]-methyl-amine (1.72 g, 100%) as colorless oil which was used in the next step without further purification.

Example 1b

Preparation of intermediate [1-(3-chloro-phenyl)-meth-(E)-ylidene]methyl-amine

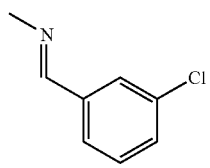

M. W. 153.6  C₈H₈ClN

A mixture of 3-chloro-benzoaldehyde (Aldrich, 97%) (4.21 g, 30.0 mmol) and methyl amine (2.0 M in THF, Aldrich, 22.5 mL, 45.0 mmol) in CH₂Cl₂ (50 mL) was stirred at rt overnight. The reaction mixture was concentrated and the residue was dried under reduced pressure to afford [[1-(3-chloro-phenyl)-meth-(E)-ylidene]-methyl-amine (4.60 g, 100%) as colorless oil which was used in the next step without further purification.

Example 1c

Preparation of intermediate [1-(4-chloro-phenyl)-meth-(E)-ylidene]-methyl-amine

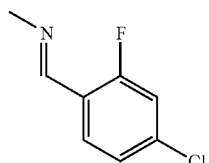

M. W. 171.6  C₈H₇FClN

A mixture of 4-chloro-2-fluoro-benzoaldehyde (Matrix Sci, 3.17 g, 20.0 mmol) and methyl amine (2.0 M in THF, Aldrich, 15 mL, 15.0 mmol) in CH₂Cl₂ (20 mL) was stirred at rt overnight. The reaction mixture was concentrated and the residue was dried under reduced pressure to afford [[1-(4-chloro-2-fluoro-phenyl)-meth-(E)-ylidene]-methyl-amine (3.32 g, 97.0%) as colorless oil which was used in the next step without further purification.

Example 1d

Preparation of intermediate [1-(4-chloro-phenyl)-meth-(E)-ylidene]-methyl-amine

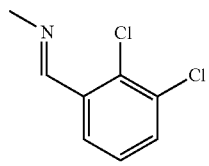

M. W. 188.6  C₈H₇Cl₂N

A mixture of 2,3-dichloro-benzoaldehyde (Aldrich, 3.50 g, 20.0 mmol) and methyl amine (2.0 M in THF, Aldrich, 15 mL, 15.0 mmol) in CH₂Cl₂ (20 mL) was stirred at rt overnight. The reaction mixture was concentrated and the residue was dried under reduced pressure to afford [[1-(4-chloro-2-fluoro-phenyl)-meth-(E)-ylidene]-methyl-amine (3.62 g, 96.3%) as colorless oil which was used in the next step without further purification.

Example 1e

Preparation of intermediate [3,3-dimethyl-but-(E)-ylidene]-trimethylsilanylmethyl-amine

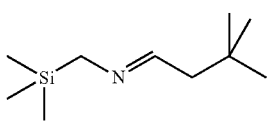

M. W. 185.39  C₁₀H₂₃Cl₂NSi

To a solution of (aminomethyl)trimethylsilane (Fluka) (1.03 g, 10 mmol) in dichloromethane (20 mL) was added 3,3-dimethyl-butyraldehyde (Aldrich) (1.0 g, 10 mmol). The reaction mixture was stirred at room temperature for 3 h. Water was added. The organic layer was separated, washed with brine, dried over MgSO₄, and concentrated to give [3,3-dimethyl-but-(E)-ylidene]-trimethylsilanylmethyl-amine as a colorless oil (1.8 g, 97%).

Example 2a

Preparation of intermediate (Z)-2-(4-chloro-2-fluoro-phenyl)-5,5-dimethyl-hex-2-enenitrile

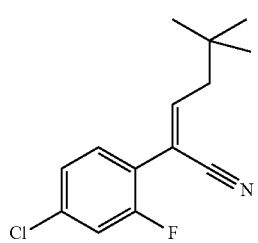

M. W. 251.7  C₁₄H₁₅FClN

To a solution of 4-chloro-2-fluoro-benzyl cyanide (Oakwood) (1.70 g, 10.0 mmol) and 3,3-dimethyl-butyraldehyde (Aldrich) (1.0 g, 10.0 mmol) in iPrOH (20 mL) was added 2 N NaOH (2.0 mL) dropwise at rt and the reaction mixture was stirred at rt overnight. The reaction mixture was diluted with EtOAc and the organic layer was separated, washed with water, brine, dried over Na$_2$SO$_4$ and concentrated. The residue was dried overnight in vacuum to give (Z)-2-(4-chloro-2-fluoro-phenyl)-5,5-dimethyl-hex-2-enenitrile (2.52 g, 100%) as a colorless oil which was used in the next step without further purification.

Example 2b

Preparation of intermediate (Z)-2-(4-chloro-2-fluoro-phenyl)-4-cyclopropyl-but-2-enenitrile

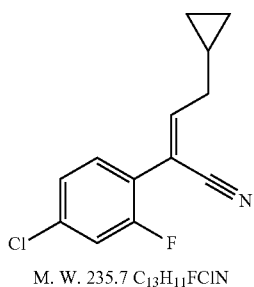

M. W. 235.7 C$_{13}$H$_{11}$FClN

To a solution of 4-chloro-2-fluoro-benzyl cyanide (Oakwood) (3.39 g, 20.0 mmol) and cyclopropyl-acetaldehyde (Aldrich) (1.68.0 g, 20.0 mmol) in iPrOH (25 mL) was added 2 N NaOH (2.0 mL) dropwise at rt and the reaction mixture was stirred at rt overnight. The reaction mixture was diluted with EtOAc and the organic layer was separated, washed with water, brine, dried over Na$_2$SO$_4$ and concentrated. The residue was dried overnight under reduced pressure to afford (Z)-2-(4-chloro-2-fluoro-phenyl)-4-cyclopropyl-but-2-enenitrile (2.36 g, 50.0%) as a colorless oil which was used in the next step without further purification.

Example 2c

Preparation of intermediate (Z)-3-(3-chloro-2-fluoro-phenyl)-2-(4-chloro-2-fluoro-phenyl)-acrylonitrile

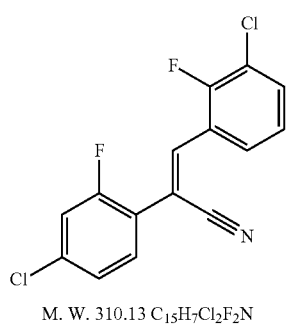

M. W. 310.13 C$_{15}$H$_{7}$Cl$_2$F$_2$N

To a solution of 4-chloro-2-fluorophenylacetonitrile (Matrix) (5 g, 30 mmol) and 3-chloro-2-fluorobenzaldehyde (Oakwood) (5 g, 32 mmol) in methanol (200 mL) was slowly added a methanolic solution (Aldrich, 25 wt. %) of sodium methoxide (21 mL, 92 mmol). The reaction mixture was heated and stirred at 45° C. for 5 h. The mixture was cooled to room temperature and filtered. The white precipitate was washed with water, cold methanol, and then dried under reduced pressure to afford (Z)-3-(3-chloro-2-fluoro-phenyl)-2-(4-chloro-2-fluoro-phenyl)-acrylonitrile as a white powder (8 g, 86%).

Example 3a

Preparation of intermediate rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile

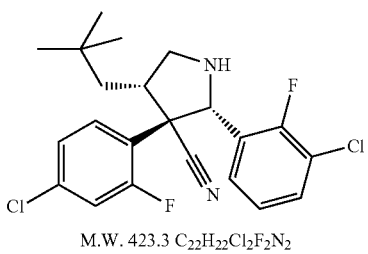

M.W. 423.3 C$_{22}$H$_{22}$Cl$_2$F$_2$N$_2$

To a solution of [1-(3-chloro-2-fluoro-phenyl)-meth-(E)-ylidene]-methyl-amine (1.72 g, 10.00 mmol) and (Z)-2-(4-chloro-2-fluoro-phenyl)-5,5-dimethyl-hex-2-enenitrile (2.52 g, 10.00 mmol) in DMSO (10 mL) was added KOH powder (1.12 g, 20.00 mmol) in one portion. The mixture was stirred at rt overnight. The reaction mixture was diluted with water and extracted with EtOAc three times (3×50 mL). The combined organic layers were washed with water and brine and dried over Na$_2$SO$_4$, and concentrated. The residue was purified by flash column (SiO$_2$, 1%-15% of EtOAc in hexanes) after concentration to give rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (0.86 g, 20.3%; HRMS (ES$^+$) m/z Calcd for C$_{22}$H$_{22}$Cl$_2$F$_2$N$_2$+H [(M+H)$^+$]: 423.1201, found: 423.1199) and rac (3S,4S,5S)-5-(3-chloro-2-fluoro-phenyl)-3-(4-chloro-2-fluoro-phenyl)-4-(2,2-dimethyl-propyl)pyrrolidine-3-carbonitrile (0.66 g, 15.6%); HRMS (ES$^+$) m/z Calcd for C$_{22}$H$_{22}$Cl$_2$F$_2$N$_2$+H [(M+H)$^+$]: 423.1201. found: 423.1202.

Example 3b

Preparation of intermediate rac-(2S,3S,4S)-2-(3-chloro-o-phenyl)-3-(4-chloro-2-fluoro-phenyl)-4-(2,2-dimethyl-propyl)-pyrrolidine-3-carbonitrile

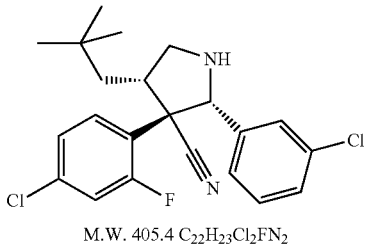

M.W. 405.4 C$_{22}$H$_{23}$Cl$_2$FN$_2$

To a solution of [1-(3-chloro-phenyl)-meth-(E)-ylidene]-methyl-amine (0.77 g, 5.00 mmol) and (Z)-2-(4-chloro-2-fluoro-phenyl)-5,5-dimethyl-hex-2-enenitrile (1.72 g, 5.00 mmol) in DMSO (5 mL) was added KOH powder (0.56 g, 10.00 mmol) in one portion. The mixture was stirred at rt overnight. The reaction mixture was diluted with water and extracted with EtOAc three times (3×50 mL). The combined organic layers were washed with water and brine and dried over Na$_2$SO$_4$, and concentrated. The residue was purified by flash column (SiO$_2$, 1%-15% of EtOAc in hexanes) after concentration to give rac-(2S,3S,4S)-2-(3-chloro-phenyl)-3-(4-chloro-2-fluoro-phenyl)-4-(2,2-dimethyl-propyl)-pyrrolidine-3-carbonitrile (0.73 g, 36.1%); HRMS (ES$^+$) m/z Calcd for C$_{22}$H$_{23}$Cl$_2$FN$_2$+H [(M+H)$^+$]: 405.1295, found: 405.1292, rac-(2S,3S,4R)-4-(4-chloro-2-fluoro-phenyl)-2-(3-chloro-phenyl)-3-(2,2-dimethyl-propyl)-pyrrolidine (0.0.42 g, 20.8%); HRMS (ES$^+$) m/z Calcd for C$_{22}$H$_{23}$Cl$_2$FN$_2$+H [(M+H)$^+$]: 405.1295, found: 405.1294, and (2S,3R,4R)-4-(4-chloro-2-fluoro-phenyl)-2-(3-chloro-phenyl)-3-(2,2-dimethyl-propyl)-pyrrolidine (0.42 g, 20.8%); HRMS (ES$^+$) m/z Calcd for C$_{22}$H$_{23}$Cl$_2$FN$_2$+H [(M+H)$^+$]: 405.1295, found: 405.1294.

Example 3c

Preparation of intermediate rac-(2S,3S,4S)-2,3-bis-(4-chloro-2-fluoro-phenyl)-4-(2,2-dimethyl-propyl)-pyrrolidine-3-carbonitrile

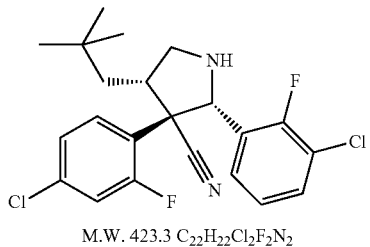

M.W. 423.3 C$_{22}$H$_{22}$Cl$_2$F$_2$N$_2$

In a manner similar to the method described in Example 3a, [1-(4-chloro-2-fluoro-phenyl)-meth-(E)-ylidene]-methyl-amine (3.43 g, 20.00 mmol) reacted with (Z)-2-(4-chloro-2-fluoro-phenyl)-5,5-dimethyl-hex-2-enenitrile (5.03 g, 20.00 mmol) in DMSO (30 mL) in the presence of KOH powder (5.72 g, 56.11 mmol) to give rac-(2S,3S,4S)-2,3-bis-(4-chloro-2-fluoro-phenyl)-4-(2,2-dimethyl-propyl)-pyrrolidine-3-carbonitrile (1.12 g 13.3%) and rac-(3S,4S,5S)-3,5-bis-(4-chloro-2-fluoro-phenyl)-4-(2,2-dimethyl-propyl)-pyrrolidine-3-carbonitrile (1.66 g 19.7%). HRMS (ES$^+$) m/z Calcd for C$_{22}$H$_{22}$Cl$_2$F$_2$N$_2$+H [(M+H)$^+$]: 423.1201, found: 423.1200.

Example 3d

Preparation of intermediate rac-(2S,3S,4S)-3-(4-chloro-2-fluoro-phenyl)-2-(2,3-dichloro-phenyl)-4-(2,2-dimethyl-propyl)-pyrrolidine-3-carbonitrile

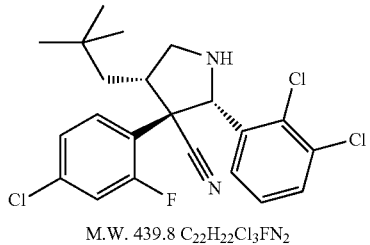

M.W. 439.8 C$_{22}$H$_{22}$Cl$_3$FN$_2$

In a manner similar to the method described in Example 3a, [1-(2,3-dichloro-phenyl)-meth-(E)-ylidene]-methyl-amine (3.76 g, 20.00 mmol) reacted with (Z)-2-(4-chloro-2-fluoro-phenyl)-5,5-dimethyl-hex-2-enenitrile (5.03 g, 20.00 mmol) in DMSO (30 mL) in the presence of KOH powder (5.72 g, 56.11 mmol) to give rac-(2S,3S,4S)-3-(4-chloro-2-fluoro-phenyl)-2-(2,3-dichloro-phenyl)-4-(2,2-dimethyl-propyl)-pyrrolidine-3-carbonitrile (1.85 g 21.0%). LC-MS (ES$^+$) m/z Calcd for C$_{22}$H$_{22}$Cl$_3$FN$_2$+H [(M+H)$^+$]: 441, found: 441.

Example 3e

Preparation of intermediate rac (2S,3S,4S)-3-(4-chloro-2-fluoro-phenyl)-2-(2,4-dichloro-phenyl)-4-(2,2-dimethyl-propyl)-pyrrolidine-3-carbonitrile

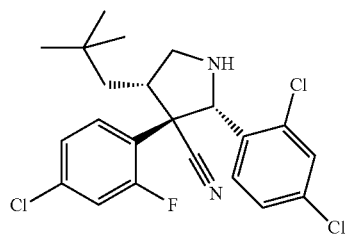

M.W. 439.8 C$_{22}$H$_{22}$Cl$_3$FN$_2$

In a manner similar to the method described in Example 3a, [1-(2,3-dichloro-phenyl)-meth-(E)-ylidene]-methyl-amine (3.76 g, 20.00 mmol) reacted with (Z)-2-(4-chloro-2-fluoro-phenyl)-5,5-dimethyl-hex-2-enenitrile (5.03 g, 20.00 mmol) in DMSO (30 mL) in the presence of KOH powder (5.72 g, 56.11 mmol) to give rac-(2S,3S,4S)-3-(4-chloro-2-fluoro-phenyl)-2-(2,3-dichloro-phenyl)-4-(2,2-dimethyl-propyl)-pyrrolidine-3-carbonitrile (1.56 g 17.7%). HRMS (ES$^+$) m/z Calcd for C$_{22}$H$_{22}$Cl$_3$FN$_2$+H [(M+H)$^+$]: 439.0906, found: 439.0905.

Example 3f

Preparation of intermediate rac-(2S,3R,4S)-4-(3-chloro-2-fluoro-phenyl)-3-(4-chloro-2-fluoro-phenyl)-2-(2,2-dimethyl-propyl)-pyrrolidine-3-carbonitrile

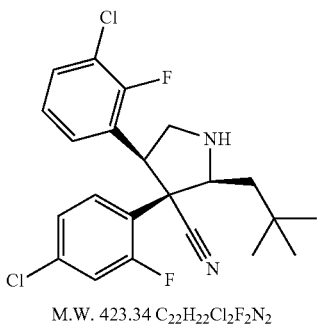

M.W. 423.34 C$_{22}$H$_{22}$Cl$_2$F$_2$N$_2$

To a solution of (Z)-3-(3-chloro-2-fluoro-phenyl)-2-(4-chloro-2-fluoro-phenyl)-acrylonitrile (1.2 g, 3.87 mmol) in hexamethylphosphoramide (20 mL) was added [3,3-dimethyl-but-(E)-ylidene]-trimethylsilanylmethyl-amine (1.1 g, 5.9 mmol), acetic acid (60 mg, 1 mmol) and H$_2$O (0.1 g, 5.6 mmol) sequentially. The reaction mixture was stirred at room temperature for 18 h. Water was added. The mixture was extracted with ethyl acetate. The organic layer was separated, and aqueous layer was extracted with ethyl acetate. The organic layers were combined, washed with water twice, dried over MgSO$_4$, then concentrated. The residue was purified by chromatography (EtOAc:hexanes=1:4, 1;3) to give rac-(2S,3R,4S)-4-(3-chloro-2-fluoro-phenyl)-3-(4-chloro-2-fluoro-phenyl)-2-(2,2-dimethyl-propyl)-pyrrolidine-3-carbonitrile as a white foam (0.4 g, 24%).

Example 4

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide

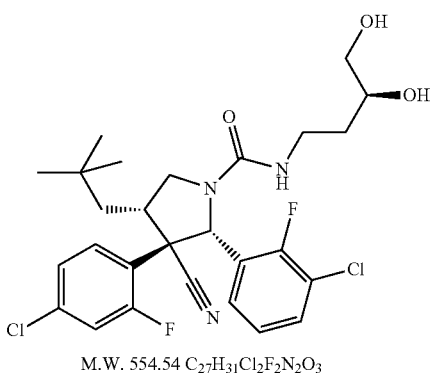

M.W. 554.54 C$_{27}$H$_{31}$Cl$_2$F$_2$N$_2$O$_3$

To a mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (126.9 mg, 0.30 mmol) and triethylamine (TEA, 120.0 mg, 1.20 mmol) in CH$_2$Cl$_2$ (10 mL) was added phosgene solution (Aldrich, 20% in toluene, 0.40 mL, 0.4 mmol) by injection, and the reaction mixture was stirred at rt for 20 min. 2-((S)-2,2-dimethyl-[1,3]dioxolan-4-yl)-ethylamine* (65.2 mg, 0.45 mmol) was then added. The reaction mixture was stirred at rt for another 30 min then concentrated to give the crude product (checked by LCMS) which was diluted with MeOH and treated with PPTS (cat.) at 120° C. for 5 min with CEM microwave reactor. The reaction mixture was concentrated under reduced pressure and the residue was diluted with CH$_2$Cl$_2$ and washed with water and brine. The organic phase was separated, filtered and dried over Na$_2$SO$_4$. The mixture was then concentrated under reduced pressure and purified by RP-HPLC to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide (62.5 mg, 39.5%, 2 steps) as a white amorphous. HRMS (ES$^+$) m/z Calcd for C$_{27}$H$_3$Cl$_2$F$_2$N$_3$O$_3$+H [(M+H)+]: 554.1784; Found: 554.1787.

*Preparation of intermediate 2-((S)-2,2-dimethyl-[1,3]dioxolan-4-yl)-ethylamine

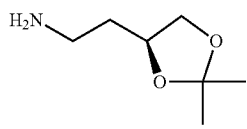

M.W. 145.20 C$_7$H$_{15}$NO$_2$

Step A. To a solution of (4S)-(+)-4-(2-hydroxyethyl)-2,2-dimethyl-1,3-dioxolane (Aldrich) (21.1 g, 0.14 mol) and triethylamine (40 mL, 0.28 mol) in dichloromethane (250 mL) at 0° C. was added methanesulfonyl chloride (13.4 mL, 0.17 mol) dropwise. The reaction mixture was stirred at 0° C. for 1.5 h, then water was added. The organic layer was separated, washed with water, brine, dried over MgSO$_4$, concentrated to give methanesulfonic acid 2-4S)-2,2-dimethyl-[1,3]dioxolan-4-yl)-ethyl ester as a yellow oil (31.7 g, 98%).

Step B. To a solution of methanesulfonic acid 2-((S)-2,2-dimethyl-[1,3]dioxolan-4-yl)-ethyl ester (31.7 g, 0.14 mol) in N,N-dimethylformamide (200 mL) was added NaN$_3$ (46 g, 0.71 mol). The reaction mixture was stirred at room temperature for 70 h. Then the mixture was partitioned between ethyl acetate and water. The organic layer was separated, washed with water, brine several times, dried over MgSO$_4$, concentrated to give (S)-4-(2-azido-ethyl)-2,2-dimethyl-[1,3]dioxolane as a yellow oil (21.3 g, 88%).

Step C. A suspension of (S)-4-(2-azido-ethyl)-2,2-dimethyl-[1,3]dioxolane as a yellow oil (18.7 g, 0.11 mol) and PtO$_2$ (2.5 g) in ethyl acetate (100 mL) was vigorously shaken in a Parr under atmosphere of H$_2$ (50 psi) for 18 h. The mixture was filtered through a short pad of celite. The filtrate was concentrated to give 2-((S)-2,2-dimethyl-[1,3]dioxolan-4-yl)-ethylamine as a colorless oil (14 g, 88%).

Preparation of (2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide and (2R,3R,4R)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide

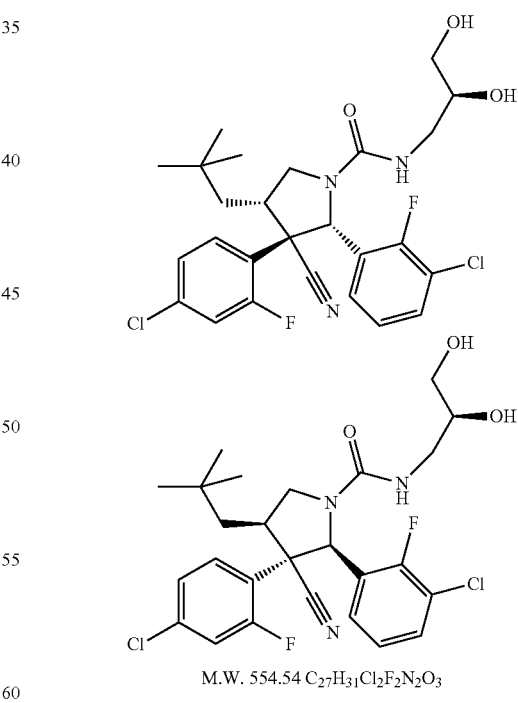

M.W. 554.54 C$_{27}$H$_{31}$Cl$_2$F$_2$N$_2$O$_3$

The racemic product obtained above (Example 4, 60 mg) was further separated by SFC chiral column to give (2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide (24.3 mg) and (2R,3R,4R)-2-(3-chloro-2-fluoro-phenyl)-3-(4-chloro-2- fluoro-phenyl)-3-cyano-4-(2,2-dimethyl-propyl)-pyrrolidine-1-carboxylic acid ((S)-3,4-dihydroxy-butyl)-amide (25.6 mg).

Example 5

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid [1-(2-hydroxy-2-methyl-propyl)-1-pyrazol-3-yl]-amide

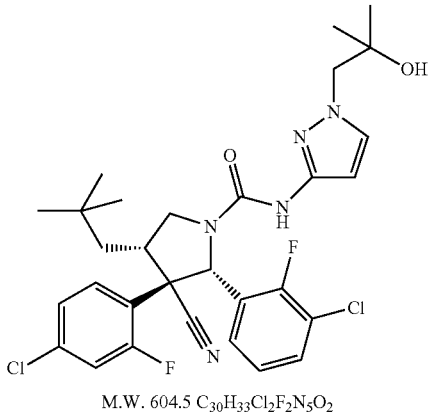

M.W. 604.5 $C_{30}H_{33}Cl_2F_2N_5O_2$

In a manner similar to the method described in Example 4, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol) prepared in Example 3a was reacted with phosgene solution (Aldrich, 20% in toluene, 0.12 mL, 0.12 mmol), in the presence of triethylamine (TEA, 30.0 mg, 0.30 mmol) in $CH_2Cl_2$ (2 mL) followed by reacting with 1-(3-amino-pyrazol-1-yl)-2-methyl-propan-2-ol (23.3 mg, 0.15 mmol) at rt for 30 min to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid [1-(2-hydroxy-2-methyl-propyl)-1H-pyrazol-3-yl]-amide (7.8 mg, 13.0%) as a white amorphous. FIRMS (ES$^+$) m/z Calcd for $C_{30}H_{33}Cl_2F_2N_5O_2$+H [(M+H)$^+$]: 604.20538, found: 604.2056.

Example 6

Preparation of rac-(2S,3S,4S)-2-(3-chloro-2-fluoro-phenyl)-3-(4-chloro-2-fluoro-phenyl)-4-(2,2-dimethyl-propyl)-1-(4-ethyl-piperazine-1-carbonyl)-pyrrolidine-3-carbonitrile

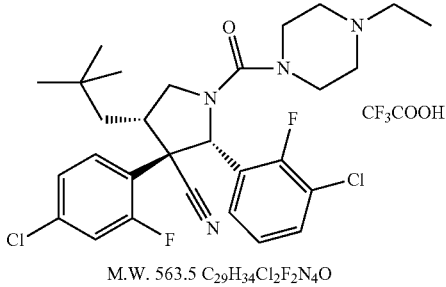

M.W. 563.5 $C_{29}H_{34}Cl_2F_2N_4O$

In a manner similar to the method described in Example 4, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol) was reacted with phosgene solution (Aldrich, 20% in toluene, 0.12 mL, 0.12 mmol), in the presence of triethylamine (TEA, 30.0 mg, 0.30 mmol) in $CH_2Cl_2$ (2 mL) followed by reacting with 1-ethyl-piperazine (17.2 mg, 0.15 mmol) at rt for 30 min to give rac-(2S,3S,4S)-2-(3-chloro-2-fluoro-phenyl)-3-(4-chloro-2-fluoro-phenyl)-4-(2,2-dimethyl-propyl)-1-(4-ethyl-piperazine-1-carbonyl)-pyrrolidine-3-carbonitrile (20.6 mg, 30.4%, as TFA salt) as a white amorphous. HRMS (ES$^+$) m/z Calcd for $C_{29}H_{34}Cl_2F_2N_4O$+H [(M+H)$^+$]: 563.2151, found: 563.2151.

Example 7

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (piperidin-4-ylmethyl)-amide

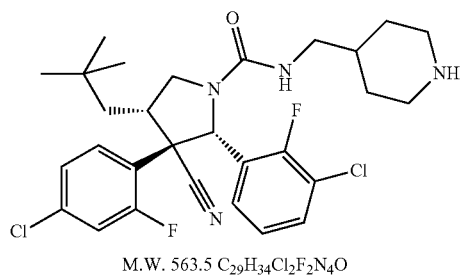

M.W. 563.5 $C_{29}H_{34}Cl_2F_2N_4O$

In a manner similar to the method described in Example 4, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol) was reacted with phosgene solution (Aldrich, 20% in toluene, 0.12 mL, 0.12 mmol), in the presence of triethylamine (TEA, 30.0 mg, 0.30 mmol) in $CH_2Cl_2$ (2 mL) followed by reacting with 4-aminomethyl-piperidine-1-carboxylic acid tert-butyl ester (66.3 mg, 0.30 mmol) at rt for 30 min to give rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-piperidine-1-carboxylic acid tert-butyl ester (48.5 mg, 73.0%) as a white amorphous.

To a mixture of rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-methyl)-piperidine-1-carboxylic acid tert-butyl ester (35.0 mg, 0.05 mmol) in $CH_2Cl_2$ (1.5 mL) was added TFA (aldrich, 97%, 1 mL) and the reaction mixture was stirred at rt for 2 hrs.

The reaction mixture was concentrated and the residue was diluted with $CH_2Cl_2$ and washed with water, sat. $NaHCO_3$ and brine. The organic phase was separated, dried over $Na_2SO_4$ and concentrated. The mixture was then concentrated and purified by flash column (1-60% of EtOAc in Hexanes) to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (piperidin-4-ylmethyl)-amide (27.3 mg, 91.9%). HRMS (ES$^+$) m/z Calcd for $C_{29}H_{34}Cl_2F_2N_4O$+H [(M+H): 563.2151; Found: 563.2149.

Example 8

Preparation of rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-methyl)-benzoic acid

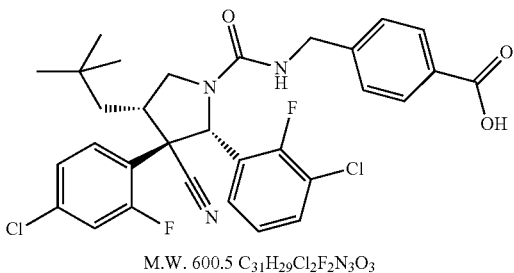

M.W. 600.5 C$_{31}$H$_{29}$Cl$_2$F$_2$N$_3$O$_3$

In a manner similar to the method described in Example 4, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (126.9 mg, 0.30 mmol) was reacted with phosgene solution (Aldrich, 20% in toluene, 0.45 mL, 0.45 mmol), in the presence of triethylamine (TEA, 272.7 mg, 2.7 mmol) in CH$_2$Cl$_2$ (10 mL) followed by reacting with 4-aminomethyl-benzoic acid methyl ester (90.7 mg, 0.45 mmol) at rt for 30 min to give rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-methyl)-benzoic acid methyl ester (108.0 mg, 59.9%) as a white amorphous which was used in the next step without further purification.

To a mixture of 4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-benzoic acid methyl ester (108.0 mg, 0.18 mmol) in THF/MeOH (0.6 mL/0.2 mL) was added 4 N LiOH (0.2 mL), and the reaction mixture was stirred at rt for 2 hrs. The reaction mixture was concentrated and quenched with 2 NH$_2$SO$_4$, extracted with EtOAc, and washed with water, brine. The organic phase was separated, and dried over Na$_2$SO$_4$. The mixture was then concentrated to 4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-benzoic acid (101.2 mg, 95.9%). FIRMS (ES$^+$) m/z Calcd for C$_{31}$H$_{29}$Cl$_2$F$_2$N$_3$O$_3$+H [(M+H): 600.1627; Found: 600.1629.

Preparation of 4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-benzoic acid and 4-({[(2R,3R,4R)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-benzoic acid

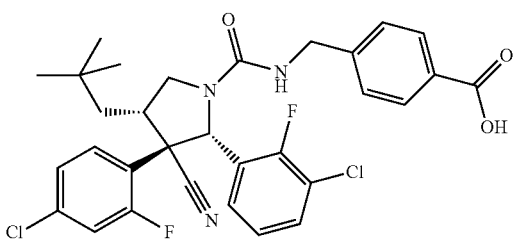

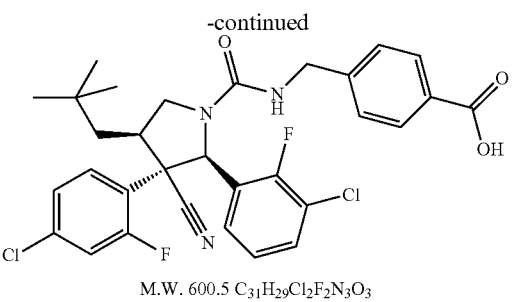

M.W. 600.5 C$_{31}$H$_{29}$Cl$_2$F$_2$N$_3$O$_3$

The racemic product obtained above (90 mg) was further separated by SFC chiral column to give 4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-benzoic acid (42.0 mg) and 4-({[(2R,3R,4R)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-methyl)-benzoic acid (38.8 mg).

Example 9

Preparation of rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid

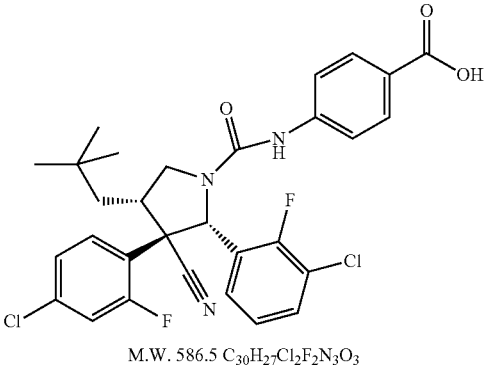

M.W. 586.5 C$_{30}$H$_{27}$Cl$_2$F$_2$N$_3$O$_3$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (84.6 mg, 0.20 mmol) and 4-isocyanato-benzoic acid methyl ester (Aldrich, 53.1 mg, 0.30 mmol) in CH$_2$Cl$_2$ (2 mL) was stirred at rt for 1 h. The reaction mixture was then concentrated and purified by flash column to give rac 4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid methyl ester (89.7 mg, 74.7%) which was used in the next step without further purification.

To a mixture of 4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid methyl ester (85.0 mg, 0.14 mmol) in THF/MeOH (0.6 mL/0.2 mL) was added 2 N LiOH (0.2 mL), and the reaction mixture was stirred at rt for 2 hrs. The reaction mixture was concentrated and quenched with 2 NH$_2$SO$_4$, extracted with EtOAc, and washed with water, brine. The organic phase was separated, and dried over Na$_2$SO$_4$. The mixture was then concentrated to give rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid (83.0 mg, 100%). HRMS (ES$^+$) m/z Calcd for C$_{30}$H$_{27}$Cl$_2$F$_2$N$_3$O$_3$+H [(M+H): 586.1471; Found: 586.1474.

Preparation of 4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid and 4-{[(2R,3R,4R)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid

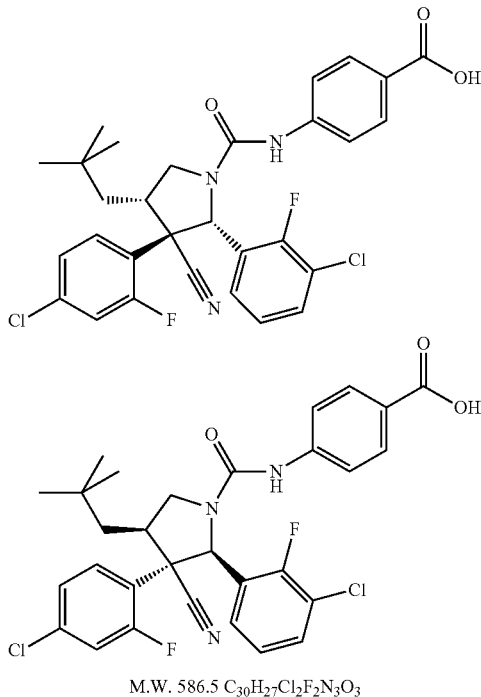

M.W. 586.5 $C_{30}H_{27}Cl_2F_2N_3O_3$

The racemic product obtained above (75 mg) was further separated by SFC chiral column to give (4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl] amino}-benzoic acid (16.5 mg) and 4-{[(2R,3R,4R)-2-(3-chloro-2-fluoro-phenyl)-3-(4-chloro-2-fluoro-phenyl)-3-cyano-4-(2,2-dimethyl-propyl)-pyrrolidine-1-carbonyl] amino}-benzoic acid (10.5 mg).

Example 10

Preparation of rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl] amino}-benzoic acid

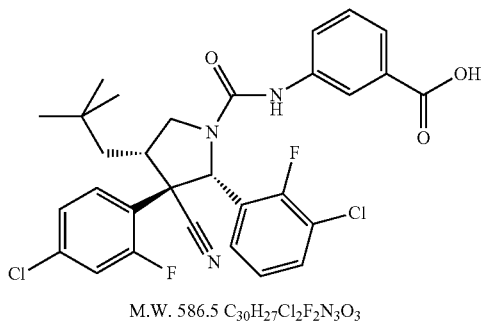

M.W. 586.5 $C_{30}H_{27}Cl_2F_2N_3O_3$

In a manner similar to the method described in Example 4, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol) was reacted with phosgene solution (Aldrich, 20% in toluene, 0.12 mL, 0.12 mmol), in the presence of triethylamine (TEA, 30.0 mg, 0.30 mmol) in $CH_2Cl_2$ (2 mL) followed by reacting with 3-amino-benzoic acid methyl ester (Aldrich, 45.0 mg, 0.30 mmol) at rt for 30 min to give rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-benzoic acid methyl ester (38.1 mg, 62.9%) as a white amorphous which was used in the next step without further purification.

To a mixture of 3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid methyl ester (20.0 mg, 0.03 mmol) in THF/MeOH (0.6 mL/0.2 mL) was added 4 N LiOH (0.2 mL), and the reaction mixture was stirred at rt for 2 hrs. The reaction mixture was concentrated and quenched with 2 $NH_2SO_4$, extracted with EtOAc, and washed with water, brine. The organic phase was separated, and dried over $Na_2SO_4$. The mixture was then concentrated to give rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid (19.5 mg, 100%). HRMS (ES+) m/z Calcd for $C_{30}H_{27}Cl_2F_2N_3O_3$+H [(M+H): 586.1471; Found: 586.1473.

Example 11

Preparation of rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid

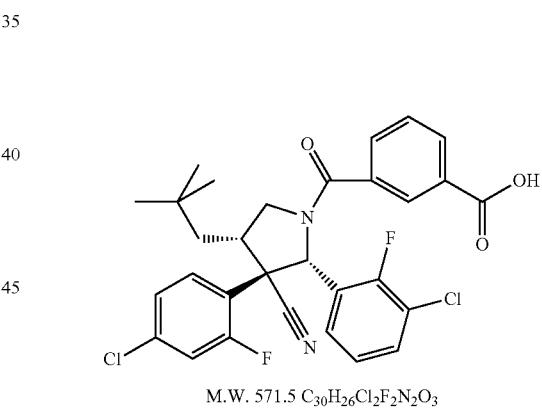

M.W. 571.5 $C_{30}H_{26}Cl_2F_2N_2O_3$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol), isophthalic acid (33.2 mg, 0.20 mmol), HATU (72.0 mg, 0.20 mmol) and $iPr_2NEt$ (0.1 mL) in $CH_2Cl_2$ (2 mL) was stirred at rt 2 hrs. The mixture was then diluted with $CH_2Cl_2$ and washed with water, brine. The organic phase was separated, filtered and dried over $Na_2SO_4$. The mixture was then concentrated and the residue was purified by RP-HPLC to give rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid (19.5 mg, 34.2%). HRMS (ES+) m/z Calcd for $C_{30}H_{26}Cl_2F_2N_2O_3$+H [(M+H): 571.1362; Found: 571.1364.

Example 12

Preparation of rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid

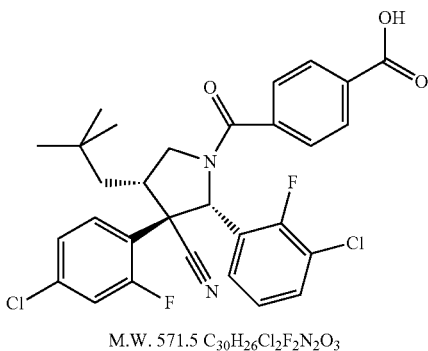

M.W. 571.5 $C_{30}H_{26}Cl_2F_2N_2O_3$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol), terephthalic acid (33.2 mg, 0.20 mmol), HATU (72.0 mg, 0.20 mmol) and iPr$_2$NEt (0.1 mL) in CH$_2$Cl$_2$ (2 mL) was stirred at rt 2 hrs. The mixture was then diluted with CH$_2$Cl$_2$ and washed with water, brine. The organic phase was separated, filtered and dried over Na$_2$SO$_4$. The mixture was then concentrated and the residue was purified by RP-HPLC to give rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid (21.5 mg, 37.6%). HRMS (ES$^+$) m/z Calcd for $C_{30}H_{26}Cl_2F_2N_2O_3$+H [(M+H): 571.1362; Found: 571.1363.

Example 13

Preparation of rac-(2S,3S,4S)-2-(3-chloro-2-fluoro-phenyl)-3-(4-chloro-2-fluoro-phenyl)-4-(2,2-dimethyl-propyl)-1-(4-hydroxymethyl-benzoyl)-pyrrolidine-3-carbonitrile

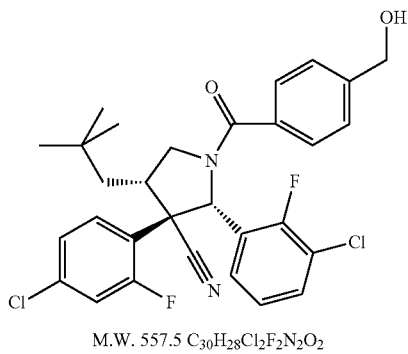

M.W. 557.5 $C_{30}H_{28}Cl_2F_2N_2O_2$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (100.0 mg, 0.23 mmol), 4-chlorocarbonyl-benzoic acid methyl ester (60.0 mg, 0.30 mmol), iPr$_2$NEt (0.12 mL, 0.69 mmol) in CH$_2$Cl$_2$ (5 mL) was stirred at rt overnight. The mixture was then diluted with CH$_2$Cl$_2$ and washed with water, brine. The organic phase was separated, filtered and dried over Na$_2$SO$_4$. The mixture was then concentrated and the residue was purified by flash column (1%-15% AcOEt in Hex) to give rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid methyl ester (132.0 mg, 98.0%).

To a solution of rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid methyl ester (130.0 mg, 0.222 mmol) in EtOH (1.0 mL) and THF (1.0 mL) was added NaBH$_4$ (36.0 mg, 0.96 mmol) and LiCl (40.7 mg, 0.96 mmol). The reaction mixture was stirred at rt overnight. Work up and the residue was purified by RP-HPLC to give rac-(2S,3S,4S)-2-(3-chloro-2-fluoro-phenyl)-3-(4-chloro-2-fluoro-phenyl)-4-(2,2-dimethyl-propyl)-1-(4-hydroxymethyl-benzoyl)-pyrrolidine-3-carbonitrile (5.7 mg, 4.6%). HRMS (ES$^+$) m/z Calcd for $C_{30}H_{28}Cl_2F_2N_2O_2$+H [(M+H): 557.1568; Found: 557.1569.

Example 14

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-chloro-phenyl)-amide

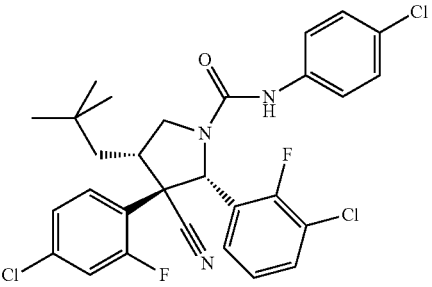

M.W. 576.9 $C_{29}H_{26}Cl_3F_2N_3O$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol) and 1-chloro-4-isocyanato-benzene (Aldrich, 45.0 mg, 0.30 mmol) in CH$_2$Cl$_2$ (2 mL) was stirred at rt for 1 h. The reaction mixture was then concentrated and purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-chloro-phenyl)-amide (35.9 mg, 59.3%) as a white amorphous. HRMS (ES$^+$) m/z Calcd for $C_{29}H_{26}Cl_2F_2N_3O$+H [(M+H)$^+$]: 576.1183, found: 576.1183.

Example 15

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid 4-chloro-benzylamide

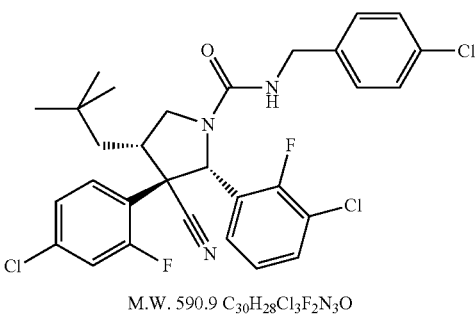

M.W. 590.9 $C_{30}H_{28}Cl_3F_2N_3O$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol) and 1-chloro-4-isocyanatomethyl-benzene (Aldrich, 20 mg, 0.12 mmol) in CH$_2$Cl$_2$ (2 mL) was stirred at rt for 1 h. The reaction mixture was then concentrated and purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-chloro-phenyl)-amide (39.7 mg, 67.2%) as a white amorphous. HRMS (ES$^+$) m/z Calcd for C$_{30}$H$_{28}$Cl$_3$F$_2$N$_3$O+H [(M+H)$^+$]: 590.1339, found: 590.1340

Example 16

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid [3-(1H-tetrazol-5-yl)-phenyl]-amide

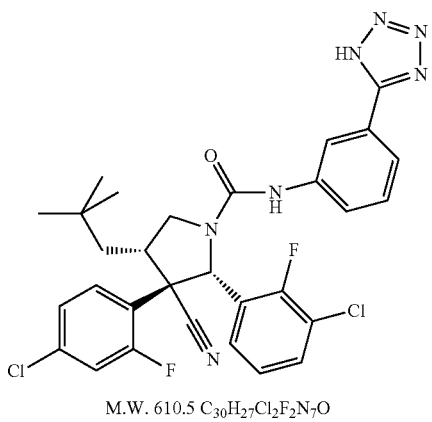

M.W. 610.5 C$_{30}$H$_{27}$Cl$_2$F$_2$N$_7$O

In a manner similar to the method described in Example 4, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol) was reacted with phosgene solution (Aldrich, 20% in toluene, 0.12 mL, 0.12 mmol), in the presence of triethylamine (TEA, 90 mg, 0.90 mmol) in CH$_2$Cl$_2$ (2 mL) followed by reacting with 3-(1H-tetrazol-5-yl)-phenylamine (48.3 mg, 0.30 mmol) at rt for 30 min to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid [3-(1H-tetrazol-5-yl)-phenyl]amide (25.3 mg, 41.4%) as a white amorphous. HRMS (ES$^+$) m/z Calcd for C$_{30}$H$_{27}$Cl$_2$F$_2$N$_7$O+H [(M+H)$^+$]: 610.1695. found: 610.1695

Example 17

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-cyano-phenyl)-amide

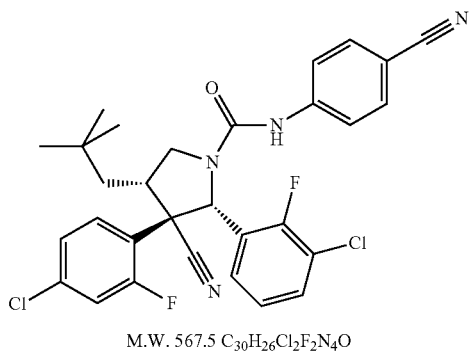

M.W. 567.5 C$_{30}$H$_{26}$Cl$_2$F$_2$N$_4$O

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (84.6 mg, 0.20 mmol) and 1-cyano-4-isocyanato-benzene (Aldrich, 34.7 mg, 0.24 mmol) in CH$_2$Cl$_2$ (2 mL) was stirred at rt for 1 h. The reaction mixture was then concentrated and triturated with EtOAt and the solid was collected to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-cyano-phenyl)-amide (1$^{st}$ crop, 54.4 mg, 2$^{nd}$ crop, 60.3 mg: 100%;) as a white solid. HRMS (ES$^+$) m/z Calcd for C$_{30}$H$_{26}$Cl$_2$F$_2$N$_4$O+H [(M+H)$^+$]: 567.1525, found: 567.1526.

Example 18

Preparation of rac-(2S,3S,4S)-2-(3-chloro-2-fluoro-phenyl)-3-(4-chloro-2-fluoro-phenyl)-1-(4-cyano-benzoyl)-4-(2,2-dimethyl-propyl)-pyrrolidine-3-carbonitrile

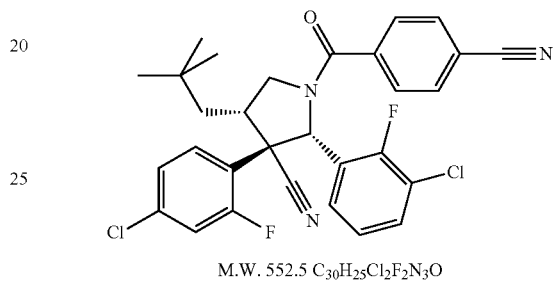

M.W. 552.5 C$_{30}$H$_{25}$Cl$_2$F$_2$N$_3$O

In a manner similar to the method described in Example 11, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (84.6 mg, 0.20 mmol) was reacted with 4-cyano-benzoic acid (Aldrich, 35.3 mg, 0.24 mmol), in the presence of HATU (72.0 mg, 0.20 mmol) and iPr$_2$NEt (0.1 mL) in CH$_2$Cl$_2$ (2 mL) at rt for 2 hrs to give rac-(2S,3S,4S)-2-(3-chloro-2-fluoro-phenyl)-3-(4-chloro-2-fluoro-phenyl)-1-(4-cyano-benzoyl)-4-(2,2-dimethyl-propyl)-pyrrolidine-3-carbonitrile (108.5 mg, 98.2%). HRMS (ES$^+$) m/z Calcd for C$_{30}$H$_{25}$Cl$_2$F$_2$N$_3$O+H [(M+H)$^+$]: 552.1417, found: 552.1416.

Example 19

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-carbamoyl-phenyl)-amide

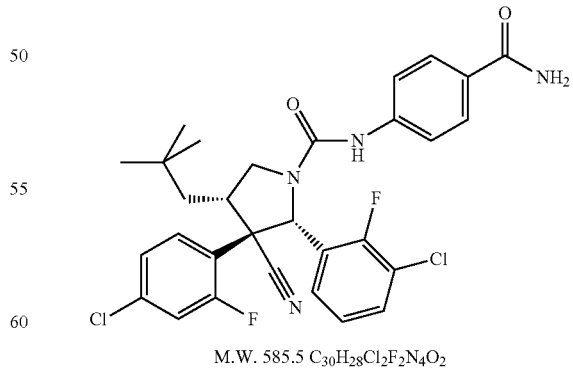

M.W. 585.5 C$_{30}$H$_{28}$Cl$_2$F$_2$N$_4$O$_2$

To the mixture of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-cyano-phenyl)-amide (56.8 mg, 0.10 mmol) and K$_2$CO$_3$ (excess) in DMSO (2 mL) was added 30% H$_2$O$_2$ (1.0 mL, excess) and the reaction mixture was stirred at rt overnight. The reaction mixture was then diluted with EtOAc washed with sat NH₄Cl, water and brine. The solvent was removed and the crude product was triturated with EtOAc and the solid was collected to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-carbamoyl-phenyl)-amide (55.9 mg, 95.5%). HRMS (ES⁺) m/z Calcd for $C_{30}H_{28}Cl_2F_2N_4O_2$+H [(M+H)⁺]: 585.1630, found: 585.1631.

Example 20

Preparation of rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzamide

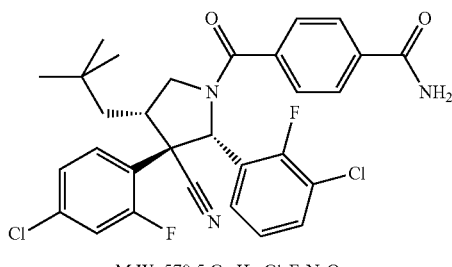

M.W. 570.5 $C_{30}H_{27}Cl_2F_2N_3O_2$

In a manner similar to the method described in Example 19, rac-(2S,3S,4S)-2-(3-chloro-2-fluoro-phenyl)-3-(4-chloro-2-fluoro-phenyl)-1-(4-cyano-benzoyl)-4-(2,2-dimethyl-propyl)-pyrrolidine-3-carbonitrile (27.6 mg, 0.05 mmol) was reacted with 30% $H_2O_2$ (1.0 mL, excess), $K_2CO_3$ (excess) in DMSO (2 mL) at rt overnight to give rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzamide (15.3 mg, 56.7%). HRMS (ES⁺) m/z Calcd for $C_{30}H_{27}Cl_2F_2N_3O_2$+H [(M+H)⁺]: 570.1521, found: 570.1523.

Example 21

Preparation of rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-2-oxo-ethyl}-2-ethoxy-benzoic acid

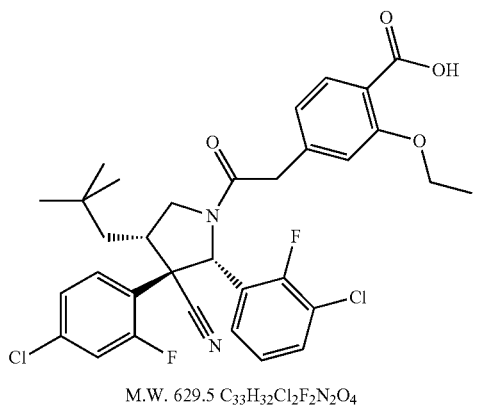

M.W. 629.5 $C_{33}H_{32}Cl_2F_2N_2O_4$

In a manner similar to the method described in Example 4, rac-(2S,3S,4S)-2-(3-chloro-2-fluoro-phenyl)-3-(4-chloro-2-fluoro-phenyl)-4-(2,2-dimethyl-propyl)-pyrrolidine-3-car-bonitrile (42.3 mg, 0.10 mmol) was reacted with 4-carboxymethyl-2-ethoxy-benzoic acid ethyl ester (Aldrich, 50.4 mg, 0.20 mmol), in the presence of HATU (91.0 mg, 0.24 mmol) and iPr₂NEt (0.1 mL) in $CH_2Cl_2$ (2 mL) at rt for 2 hrs to give rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-2-oxo-ethyl}-2-ethoxy-benzoic acid ethyl ester (52.6 mg, 37.6%) which was used in the next step without further purification.

To a mixture of rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-2-oxo-ethyl}-2-ethoxy-benzoic acid ethyl ester (50.0 mg, 0.076 mmol) in THF/MeOH (1.2 mL/0.4 mL) was added 4 N LiOH (0.4 mL), and the reaction mixture was stirred at rt for 2 hrs. The reaction mixture was concentrated and quenched with 2 $NH_2SO_4$, extracted with EtOAc, and washed with water, brine. The organic phase was separated, and dried over $Na_2SO_4$. The mixture was then concentrated and the residue was purified by RP-HPLC to give rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-2-oxo-ethyl}-2-ethoxy-benzoic acid (24.4 mg, 50.9%). HRMS (ES⁺) m/z Calcd for $C_{33}H_{32}Cl_2F_2N_2O_4$+H [(M+H)⁺]: 629.1780, found: 629.1782.

Example 22

Preparation of rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-4-oxo-butyl}-benzoic acid

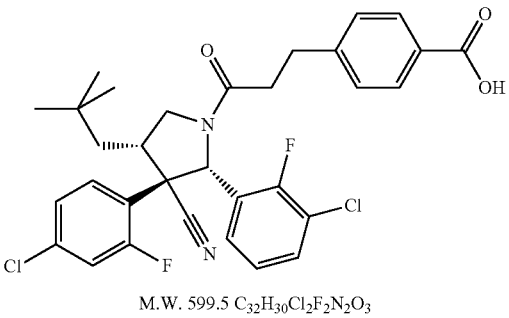

M.W. 599.5 $C_{32}H_{30}Cl_2F_2N_2O_3$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.3 mg, 0.10 mmol), 4-(4-oxo-pentyl)-benzoic acid (58.3 mg, 0.30 mmol), HATU (114.0 mg, 0.30 mmol) and iPr₂NEt (0.1 mL) in $CH_2Cl_2$ (2 mL) was stirred at rt 2 hrs. The mixture was then diluted with $CH_2Cl_2$ and washed with water, brine. The organic phase was separated, filtered and dried over $Na_2SO_4$. The mixture was then concentrated and the residue was purified by RP-HPLC to rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-4-oxo-butyl}-benzoic acid (28.9 mg, 48.2%). HRMS (ES⁺) m/z Calcd for $C_{33}H_{30}Cl_2F_2N_2O_3$+H [(M+H): 599.1675; Found: 599.1674.

Example 23

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid 4-fluoro-benzylamide

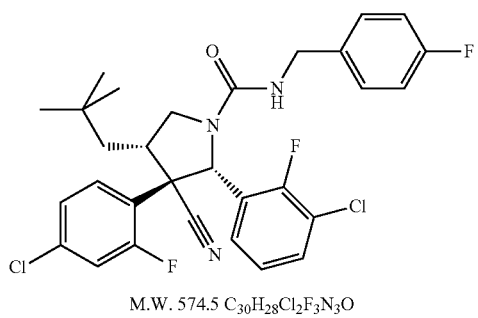

M.W. 574.5 $C_{30}H_{28}Cl_2F_3N_3O$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (30 mg, 0.07 mmol) and 1-fluoro-4-isocyanatomethyl-benzene (Aldrich, 16.1 mg, 0.11 mmol) in $CH_2Cl_2$ (2 mL) was stirred at rt for 1 h. The reaction mixture was then concentrated and purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-fluoro-phenyl)-amide (18.9 mg, 59.3%) as a white amorphous. HRMS (ES$^+$) m/z Calcd for $C_{30}H_{28}Cl_2F_3N_3O+H$ [(M+H)$^+$]: 574.1635, found: 574.1633

Example 24

Preparation of rac-4-{[(2S,3S,4S)-2,3-bis-(4-chloro-2-fluoro-phenyl)-3-cyano-4-(2,2-dimethyl-propyl)-pyrrolidine-1-carbonyl]-amino}-benzoic acid

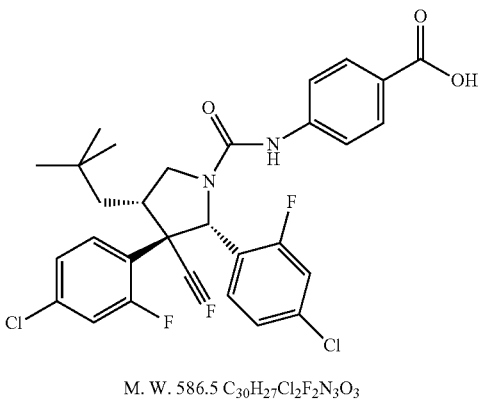

M. W. 586.5 $C_{30}H_{27}Cl_2F_2N_3O_3$

A mixture of rac-(2S,3S,4S)-2,3-bis(4-chloro-2-fluoro-phenyl)-4-(2,2-dimethyl-propyl)-pyrrolidine-3-carbonitrile (150.0 mg, 0.35 mmol) and 4-isocyanato-benzoic acid methyl ester (Aldrich, 86.0 mg, 0.53 mmol) in $CH_2Cl_2$ (5 mL) was stirred at rt for 3 h. The reaction mixture was then concentrated and purified by flash column to give rac-4-{[(2S,3S,4S)-2,3-bis-(4-chloro-2-fluoro-phenyl)-3-cyano-4-(2,2-dimethyl-propyl)-pyrrolidine-1-carbonyl]amino}-benzoic acid methyl ester (141.6 mg, 66.6%) which was used in the next step without further purification.

To a mixture of rac-4-{[(2S,3S,4S)-2,3-bis-(4-chloro-2-fluoro-phenyl)-3-cyano-4-(2,2-dimethyl-propyl)-pyrrolidine-1-carbonyl]-amino}-benzoic acid methyl ester (142.6 mg, 0.24 mmol) in THF/MeOH (3.4 mL/0.8 mL) was added 4 N LiOH (1.4 mL), and the reaction mixture was stirred at rt overnight. The reaction mixture was concentrated and quenched with 2 $NH_2SO_4$, extracted with EtOAc, and washed with water, brine. The organic phase was separated, and dried over $Na_2SO_4$. The mixture was then concentrated to give rac-4-{[(2S,3S,4S)-2,3-bis-(4-chloro-2-fluoro-phenyl)-3-cyano-4-(2,2-dimethyl-propyl)-pyrrolidine-1-carbonyl]-amino}-benzoic acid (111.6 mg, 80.6%). HRMS (ES$^+$) m/z Calcd for $C_{30}H_{27}Cl_2F_2N_3O_3+H$ [(M+H): 586.1471; Found: 586.1472.

Example 25

Preparation of rac-4-({[(2S,3S,4S)-2,3-bis-(4-chloro-2-fluoro-phenyl)-3-cyano-4-(2,2-dimethyl-propyl)-pyrrolidine-1-carbonyl]-amino}-methyl)-benzoic acid

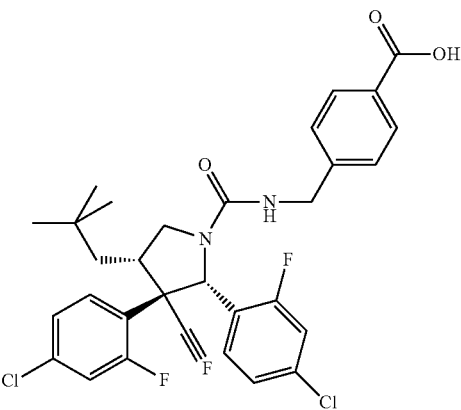

M. W. 600.5 $C_{31}H_{29}Cl_2F_2N_3O_3$

In a manner similar to the method described in Example 4, rac-(2S,3S,4S)-2,3-bis(4-chloro-2-fluoro-phenyl)-4-(2,2-dimethyl-propyl)-pyrrolidine-3-carbonitrile (126.9 mg, 0.30 mmol) was reacted with phosgene solution (Aldrich, 20% in toluene, 0.12 mL, 0.12 mmol), in the presence of triethylamine (TEA, 90 mg, 0.90 mmol) in $CH_2Cl_2$ (2 mL) followed by reacting with 4-aminomethyl-benzoic acid methyl ester hydrochloride (90.7 mg, 0.45 mmol) at rt for 30 min to give rac-4-({[(2S,3S,4S)-2,3-bis-(4-chloro-2-fluoro-phenyl)-3-cyano-4-(2,2-dimethyl-propyl)-pyrrolidine-1-carbonyl]-amino}-methyl)-benzoic acid methyl ester (110.5 mg, 60.9%) as a white amorphous solid.

To a mixture of rac-4-({[(2S,3S,4S)-2,3-bis-(4-chloro-2-fluoro-phenyl)-3-cyano-4-(2,2-dimethyl-propyl)-pyrrolidine-1-carbonyl]-amino}-methyl)-benzoic acid methyl ester (105.0 mg, 0.17 mmol) in THF/MeOH (1.8 mL/0.6 mL) was added 4 N LiOH (0.6 mL), and the reaction mixture was stirred at rt for 2 hrs. The reaction mixture was concentrated and quenched with 2 N $H_2SO_4$, extracted with EtOAc, and washed with water, brine. The organic phase was separated, and dried over $Na_2SO_4$. The mixture was then concentrated and purified by RP-HPLC to give rac-4-({[(2S,3S,4S)-2,3-bis-(4-chloro-2-fluoro-phenyl)-3-cyano-4-(2,2-dimethyl-propyl)-pyrrolidine-1-carbonyl]-amino}-methyl)-benzoic acid (100.1 mg, 97.6%). HRMS (ES$^+$) m/z Calcd for $C_{31}H_{29}Cl_2F_2N_3O_3+H$ [(M+H): 600.1627; Found: 600.1628.

Example 26

Preparation of rac-4-{[(2S,3S,4S)-3-(4-chloro-2-fluoro-phenyl)-3-cyano-2-(2,3-dichloro-phenyl)-4-(2,2-dimethyl-propyl)-pyrrolidine-1-carbonyl]amino}-benzoic acid

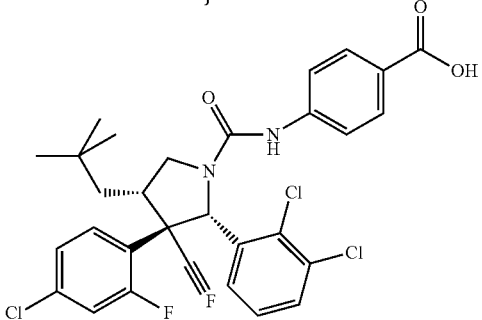

M. W. 602.9 $C_{30}H_{27}Cl_3FN_3O_3$

A mixture of rac-4-{[(2S,3S,4S)-3-(4-chloro-2-fluoro-phenyl)-2-(2,3-dichloro-phenyl)-4-(2,2-dimethyl-propyl)-pyrrolidine-3-carbonitrile (88.0 mg, 0.20 mmol) and 4-isocyanato-benzoic acid methyl ester (Aldrich, 42.5 mg, 0.22 mmol) in $CH_2Cl_2$ (2 mL) was stirred at rt for 1 h. The reaction mixture was then concentrated and purified by flash column to give rac-4-{[(2S,3S,4S)-3-(4-chloro-2-fluoro-phenyl)-3-cyano-2-(2,3-dichloro-phenyl)-4-(2,2-dimethyl-propyl)-pyrrolidine-1-carbonyl]-amino}-benzoic acid methyl ester (98.6 mg, 79.9%) which was used in the next step without further purification.

To a mixture of rac-4-{[(2S,3S,4S)-3-(4-chloro-2-fluoro-phenyl)-3-cyano-2-(2,3-dichloro-phenyl)-4-(2,2-dimethyl-propyl)-pyrrolidine-1-carbonyl]-amino}-benzoic acid methyl ester (85.0 mg, 0.14 mmol) in THF/MeOH (0.6 mL/0.2 mL) was added 4 N LiOH (0.2 mL), and the reaction mixture was stirred at rt for 2 hrs. The reaction mixture was concentrated and quenched with 2 $NH_2SO_4$, extracted with EtOAc, and washed with water, brine. The organic phase was separated, and dried over $Na_2SO_4$. The mixture was then concentrated to give rac-4-{[(2S,3S,4S)-3-(4-chloro-2-fluoro-phenyl)-3-cyano-2-(2,3-dichloro-phenyl)-4-(2,2-dimethyl-propyl)-pyrrolidine-1-carbonyl]-amino}-benzoic acid (54.3 mg, 65.4%). LC-MS (ES$^+$) m/z Calcd for $C_{30}H_{27}Cl_3FN_3O_3$+H [(M+H): 604; Found: 604.

Example 27

Preparation of rac-4-({[(2S,3S,4S)-3-(4-chloro-2-fluoro-phenyl)-3-cyano-2-(2,3-dichloro-phenyl)-4-(2,2-dimethyl-propyl)-pyrrolidine-1-carbonyl]-amino}-methyl)-benzoic acid

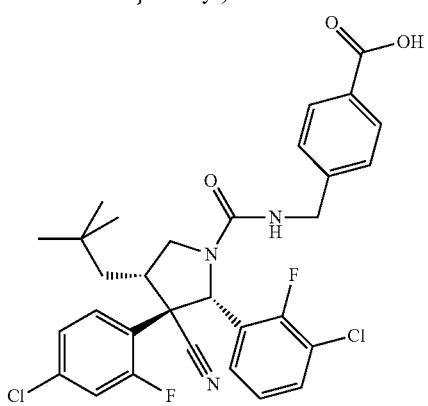

M. W. 617.0 $C_{31}H_{29}Cl_3FN_3O_3$

In a manner similar to the method described in Example 4, rac-(2S,3S,4S)-2-(2,3-dichloro-phenyl)-3-(4-chloro-2-fluoro-phenyl)-4-(2,2-dimethyl-propyl)-pyrrolidine-3-carbonitrile (88.0 mg, 0.20 mmol) was reacted with phosgene solution (Aldrich, 20% in toluene, 0.23 mL, 0.23 mmol), in the presence of triethylamine (TEA, 272.7 mg, 2.7 mmol) in $CH_2Cl_2$ (3 mL) followed by reacting with 4-aminomethyl-benzoic acid methyl ester (AK-Scientific, 60.5 mg, 0.30 mmol) at rt for 2 hrs to give rac-4-({[(2S,3S,4S)-2-(2,3-dichloro-phenyl)-3-(4-chloro-2-fluoro-phenyl)-3-cyano-4-(2,2-dimethyl-propyl)-pyrrolidine-1-carbonyl]-amino}-methyl)-benzoic acid methyl ester (126.0 mg, 43.8%) as a white amorphous solid which was used in the next step without further purification.

To a mixture of rac-4-({[(2S,3S,4S)-2-(2,3-dichloro-phenyl)-3-(4-chloro-2-fluoro-phenyl)-3-cyano-4-(2,2-dimethyl-propyl)-pyrrolidine-1-carbonyl]-amino}-methyl)-benzoic acid methyl ester (44.2 mg, 0.07 mmol) in THF/MeOH (0.6 mL/0.2 mL) was added 4 N LiOH (0.2 mL), and the reaction mixture was stirred at rt overnight. The reaction mixture was concentrated and quenched with 2 $NH_2SO_4$, extracted with EtOAc, and washed with water, brine. The organic phase was separated, and dried over $Na_2SO_4$. The mixture was then concentrated to give rac-4-({[(2S,3S,4S)-3-(4-chloro-2-fluoro-phenyl)-3-cyano-2-(2,3-dichloro-phenyl)-4-(2,2-dimethyl-propyl)-pyrrolidine-1-carbonyl]-amino}-methyl)-benzoic acid (43.0 mg, 99.6%). LC-MS (ES$^{+/-}$) m/z Calcd for $C_{31}H_{29}Cl_3FN_3O_3$: 617; Found: 617.

Example 28

Preparation of rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propenyl}-benzoic acid

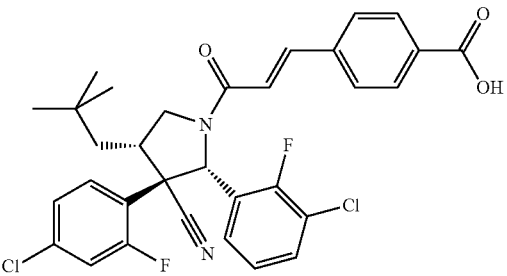

M. W. 598.5 $C_{32}H_{28}Cl_2F_2N_2O_3$

In a manner similar to the method described in Example 4, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (116 mg, 0.27 mmol) was reacted with 4-((E)-2-carboxyvinyl)-benzoic acid methyl ester* (84.7 mg, 0.41 mmol), in the presence of HATU (156.0 mg, 0.41 mmol) and iPr$_2$NEt (146.0 mg, 1.15 mmol) in $CH_2Cl_2$ (5 mL) at rt for 2 hrs to give rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propenyl}-benzoic acid methyl ester (120.2 mg, 71.5%) which was used in the next step without further purification.

*Preparation of 4-((E)-2-carboxyvinyl)-benzoic acid methyl ester

In a manner similar to the method described in Example 8, rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propenyl}-benzoic acid methyl ester (88.1 mg, 0.14 mmol) was treated with 2 N LiOH (1.0 mL) in THF/MeOH (3 mL/1 mL) at rt for 3 hrs and purified by RP-HPLC to rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propenyl}-benzoic acid (19.2 mg, 22.3%). HRMS (ES$^+$) m/z Calcd for $C_{32}H_{28}Cl_2F_2N_2O_3$+H [(M+H): 597.1518; Found: 597.1518.

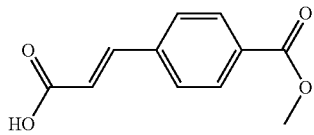

M. W. 206.2 $C_{11}H_{10}O_4$

To a solution of tert-butyl P,P-dimethylphosphonoacetate (Fluka, 1.43 g, 6.4 mmol) in THF (40 mL) was added NaH (Alderich, 60%, 536 mg, 13.4 mmol) portionwise at rt over 30 min. Methyl 4-formylbenzoate (Alderich, 1.0 g, 6.09 mmol) was then added and the reaction mixture was stirred at rt for 4 hrs. The reaction was quenched with water and extracted with EtOAc. The organic layer was separated, and dried over $Na_2SO_4$. The mixture was then concentrated to give the crude 4-((E)-2-tert-butoxycarbonyl-vinyl)-benzoic acid methyl ester (1.89 g, 118%).

The crude 4-((E)-2-tert-butoxycarbonyl-vinyl)-benzoic acid methyl ester (1.00 g, 3.81 mmol) was then treated with 4N HCl in dioxane (Aldrich, 4 mL, 16.0 mmol) at rt for 2 hrs to give 4-((E)-2-carboxyvinyl)-benzoic acid methyl ester (0.43 g, 64.5%, 2 steps) after work up.

Example 29

Preparation of rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propionic acid

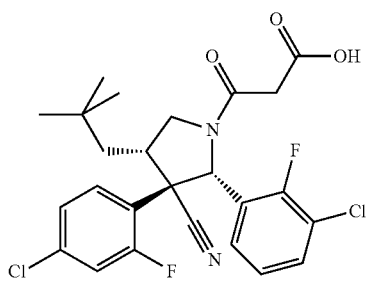

M. W. 509.4 $C_{25}H_{24}Cl_2F_2N_2O_3$

A mixture of methyl malonyl chloride (Aldrich, 127 mg, 0.93 mmol), DIPEA (Aldrich, 297.0 mg, 2.3 mmol) and rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (150 mg, 0.35 mmol) was stirred at rt overnight. The reaction mixture was concentrated and purified by RP-HPLC to give rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propionic acid methyl ester (136.2 mg, 73.5%). In a manner similar to the method described in Example 8, rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propionic acid methyl ester (120 mg, 0.23 mmol) was treated with 2 N LiOH (1.0 mL) in THF/MeOH (3 mL/1 mL) at rt for 3 hrs and purified by RP-HPLC to rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propionic acid (21.2 mg, 18.2%). HRMS (ES$^+$) m/z Calcd for $C_{25}H_{24}Cl_2F_2N_2O_3$+H [(M+H): 509.1205; Found: 509.1207.

Example 30

Preparation of intermediate rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid tert-butyl ester

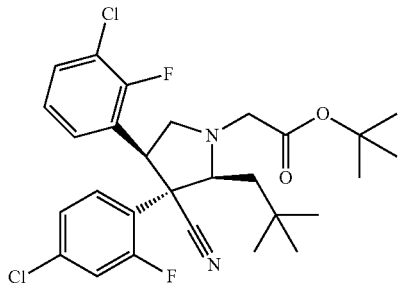

M. W. 537.48 $C_{28}H_{32}Cl_2F_2N_2O_2$

To a solution of rac-(2S,3R,4S)-4-(3-chloro-2-fluoro-phenyl)-3-(4-chloro-2-fluoro-phenyl)-2-(2,2-dimethyl-propyl)-pyrrolidine-3-carbonitrile (2.5 g, 5.9 mmol) in N,N-dimethylformamide (50 mL) was added tert-butyl bromoacetate (2.5 g, 12.8 mmol) and $Cs_2CO_3$ (5 g, 15.4 mmol). The reaction mixture was stirred at room temperature for 66 h. Water was added. The mixture was extracted with ethyl acetate. The organic layer was separated, and aqueous layer was extracted with ethyl acetate. The organic layers were combined, washed with water twice, dried over $MgSO_4$, then concentrated. The residue was purified by chromatography (EtOAc:hexanes=1:10) to give rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid tert-butyl ester as a white foam (2.1 g, 66%).

Example 31

Preparation of rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid

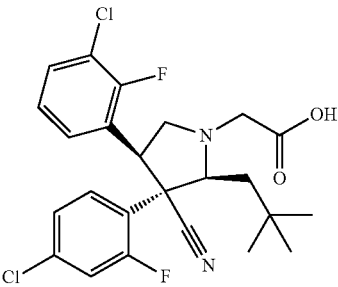

M. W. 481.37 $C_{24}H_{24}Cl_2F_2N_2O_2$

To a solution of rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid tert-butyl ester (2.1 g, 3.9 mmol) in dichloromethane (20 mL) was added trifluoroacetic acid (10 mL). The reaction mixture was stirred at room temperature for 24 h. The mixture was concentrated, and water was added. The "pH" of the mixture was adjusted to 6-7 by saturated aqueous NaHCO$_3$ solution, then extracted with ethyl acetate. The organic layer was separated, washed with water, brine, dried over MgSO$_4$, then concentrated to give rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid as a off-white solid (1.6 g, 85%). HRMS (ES$^+$) m/z Calcd for C$_{24}$H$_{24}$Cl$_2$F$_2$N$_2$O$_2$+H [(M+H): 481.1256; Found: 481.1254.

Example 32

Preparation of rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid methyl ester

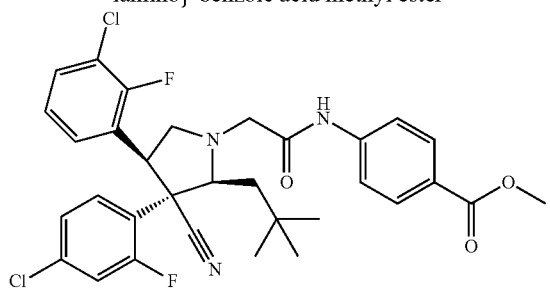

M. W. 614.52 C$_{32}$H$_{31}$Cl$_2$F$_2$N$_3$O$_3$

A mixture of rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid (0.5 g, 1.04 mmol), methyl 4-aminobenzoate (Aldrich) (0.3 g, 1.99 mmol), HATU (0.4 g, 1.05 mmol) and iPr$_2$NEt (0.3 g, 2.33 mmol) in CH$_2$Cl$_2$ (30 mL) was stirred at room temperature for 20 h. The mixture was then diluted with CH$_2$Cl$_2$ and washed with water, brine. The organic phase was separated, filtered and dried over Na$_2$SO$_4$. The mixture was then concentrated and purified by chromatography (EtOAc:hexanes=1:5) to give rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid methyl ester as a white solid (0.5 g, 81%).

Example 33

Preparation of rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid

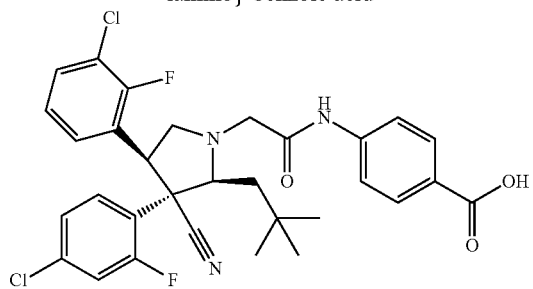

M. W. 600.50 C$_{31}$H$_{29}$Cl$_2$F$_2$N$_3$O$_3$

To a solution of rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid methyl ester (0.35 g, 0.57 mmol) in tetrahydrofuran (30 mL) was added an aqueous solution (1 N) of NaOH (10 mL, 10 mmol) and methanol (10 mL). The reaction mixture was stirred at room temperature for 24 h, and the "pH" of the solution was adjusted to 5-6 by aqueous HCl solution. The mixture was extracted ethyl acetate twice. The combined organic extracts were washed with water, brine, dried over MgSO$_4$, and concentrated to give rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid as a white solid (0.33 g, 96%). HRMS (ES$^+$) m/z Calcd for C$_{31}$H$_{29}$Cl$_2$F$_2$N$_3$O$_3$+H [(M+H): 600.1267; Found: 600.1628.

Example 34

Preparation of rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzamide

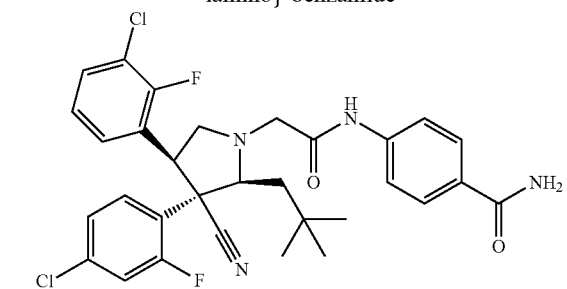

M. W. 599.51 C$_{31}$H$_{30}$Cl$_2$F$_2$N$_4$O$_2$

A mixture of rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid (0.33 g, 0.55 mmol), a solution of ammonia (0.5 M in dioxane, Aldrich, 2 mL, 1 mmol), HATU (0.3 g, 0.79 mmol) and iPr$_2$NEt (0.3 g, 2.33 mmol) in CH$_2$Cl$_2$ (20 mL) was stirred at room temperature for 20 h. The mixture was then diluted with CH$_2$Cl$_2$ and washed with water, brine. The organic phase was separated, filtered and dried over Na$_2$SO$_4$. The mixture was then concentrated and purified by chromatography (EtOAc) to give rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzamide as a white solid (0.33 g, 100%).

Example 35

Preparation of rac-2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-N—((S)-3,4-dihydroxy-butyl)-acetamide

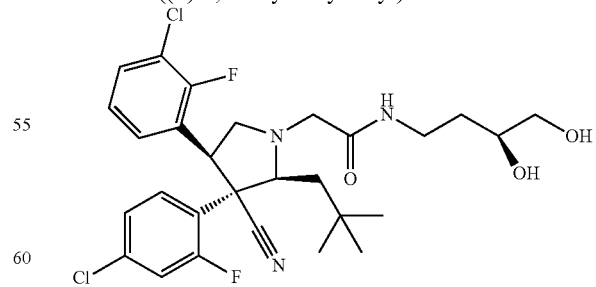

M. W. 568.50 C$_{28}$H$_{33}$Cl$_2$F$_2$N$_3$O$_3$

A mixture of rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid (0.2 g, 0.41 mmol), 2-((S)-2,2-dimethyl-[1,3]dioxolan-4-yl)-ethylamine (0.15 g, 1 mmol), HATU (0.23 g, 0.6 mmol) and iPr$_2$NEt (0.29 mL, 1.68 mmol) in CH$_2$Cl$_2$ (30 mL) was stirred at room temperature for 20 h. The reaction mixture was quenched with water was and the organic layer was separated, the aqueous layer was extracted with ethyl acetate. The organic layers were combined, dried over Na$_2$SO$_4$, and concentrated. The residue was dissolved into tetrahydrofuran (7 mL), and aqueous HCl solution (1 N, 3 mL, 3 mmol) was added to the solution. The reaction mixture was stirred at room temperature for 0.5 h. The solvent was removed, and the residue was partitioned between ethyl acetate and saturated aqueous NaHCO$_3$ solution. The organic layer was separated, washed with water, brine, dried over Na$_2$SO$_4$, and concentrated. The residue was purified by chromatography (5% MeOH in EtOAc) to give rac-2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-N—((S)-3,4-dihydroxy-butyl)-acetamide as an off-white solid (0.1 g, 42%). HRMS (ES$^+$) m/z Calcd for C$_{28}$H$_{33}$Cl$_2$F$_2$N$_3$O$_3$+H [(M+H)+]: 568.1940; Found: 568.1943.

Example 36

Preparation of intermediate rac-(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl chloride

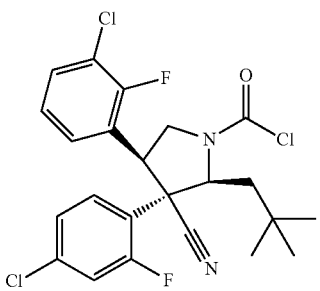

M. W. 485.79 C$_{23}$H$_{21}$Cl$_3$F$_2$N$_2$O

To a solution of rac-(2S,3R,4S)-4-(3-chloro-2-fluoro-phenyl)-3-(4-chloro-2-fluoro-phenyl)-2-(2,2-dimethyl-propyl)-pyrrolidine-3-carbonitrile prepared in Example 3 (0.3 g, 0.71 mmol) in dichloromethane (5 mL) was added saturated aqueous NaHCO$_3$ solution (5 mL). The temperature of the mixture was lowered to 0° C., and a solution of phosgene (Aldrich, 20% in toluene, 0.67 mL, 1.28 mmol) was added dropwise via a syringe. The reaction mixture was stirred at room temperature for 30 min, then diluted dichloromethane. The organic layer was separated, the aqueous layer was extracted with dichloromethane (2×). The combined organic layers were washed with water, brine, dried over MgSO$_4$, and concentrated to give crude rac-(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl chloride as a light yellow oil (0.34 g, 100%).

Example 37

Preparation of rac-(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carboxylic acid ((S)-3,4-dihydroxy-butyl)-amide

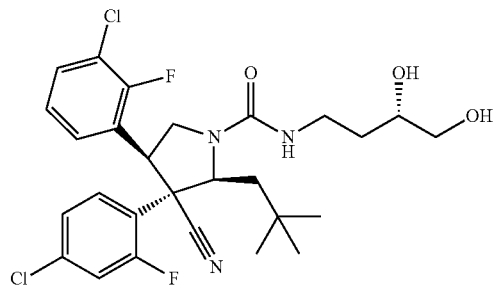

M. W. 554.54 C$_{27}$H$_{31}$Cl$_2$F$_2$N$_2$O$_3$

To a solution of rac-(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl chloride (0.34 g, 0.7 mmol) in tetrahydrofuran (5 mL) was added 2-((S)-2,2-dimethyl-[1,3]dioxolan-4-yl)-ethylamine (0.1 g, 0.71 mmol) and triethylamine (0.15 mL, 1 mmol). The reaction mixture was stirred at room temperature for 30 min. An aqueous HCl solution (1 N, 5 mL, 5 mmol) was added. The reaction mixture was stirred at room temperature for 1 h. The solvents were removed and the residue was partitioned between ethyl acetate and NaHCO$_3$ (sat.) solution. The organic layer was separated, washed with water, brine, dried over MgSO$_4$, and concentrated. The residue was purified by column chromatography (EtOAc) to afford rac-(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carboxylic acid ((S)-3,4-dihydroxy-butyl)-amide as a white solid (0.11 g, 28%). HRMS (ES$^+$) m/z Calcd for C$_{27}$H$_{31}$Cl$_2$F$_2$N$_3$O$_3$+H [(M+H)+]: 554.1784; Found: 554.1785.

Example 38

Preparation of rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl]-amino}-benzoic acid ethyl ester

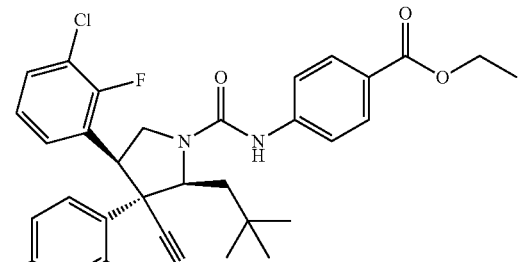

M. W. 614.52 C$_{32}$H$_{31}$Cl$_2$F$_2$N$_3$O$_3$

To a solution of rac-(2S,3R,4S)-4-(3-chloro-2-fluoro-phenyl)-3-(4-chloro-2-fluoro-phenyl)-2-(2,2-dimethyl-propyl)-pyrrolidine-3-carbonitrile prepared in Example 3 (0.44 g, 1.04 mmol) in dichloromethane (5 mL) was added 4-isocyanato-benzoic acid ethyl ester (Aldrich, 0.22 g, 1.14 mmol) and triethylamine (0.22 mL, 1.56 mmol). The reaction mixture was stirred at room temperature for 30 min. Water was added, the mixture was partitioned between ethyl acetate and water. The organic layer was separated, washed with water, brine, dried over MgSO$_4$, and concentrated. The residue was purified by chromatography (25% EtOAc in hexanes) to give rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl]-amino}-benzoic acid ethyl ester as a white solid (0.59 g, 92%)

HRMS (ES$^+$) m/z Calcd for C$_{32}$H$_{31}$Cl$_2$F$_2$N$_3$O$_3$+H [(M+H)+]: 614.1784; Found: 614.1782.

Example 39

Preparation of rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl]-amino}-benzoic acid

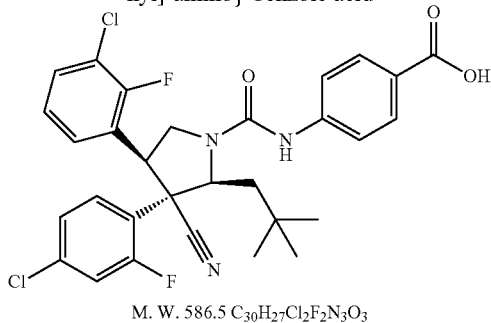

M. W. 586.5 C$_{30}$H$_{27}$Cl$_2$F$_2$N$_3$O$_3$

A mixture of rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl]-amino}-benzoic acid ethyl ester (0.2 g, 0.32 mmol) in methanol (5 mL) was added an aqueous solution (1 N) of NaOH (5 mL, 5 mmol). The reaction mixture was stirred at room temperature for 20 h. The "pH" of the mixture was adjusted to 5-6 by diluted aqueous HCl solution. The mixture was partitioned between EtOAc and water. The organic layer was separated, and the aqueous layer was extracted with ethyl acetate. The organic layers were combined, washed with water, brine, dried over MgSO$_4$, and concentrated. The residue was purified by chromatography (75% EtOAc in hexanes) to give rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl] amino}-benzoic acid as a white solid (0.1 g, 50%). HRMS (ES$^+$) m/z Calcd for C$_{30}$H$_{27}$Cl$_2$F$_2$N$_3$O$_3$+H [(M+H): 586.1471; Found: 586.1473.

Example 40

Preparation of intermediate rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid methyl ester

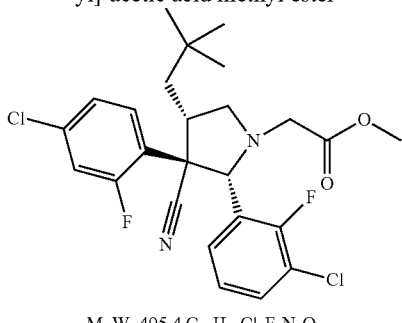

M. W. 495.4 C$_{25}$H$_{26}$Cl$_2$F$_2$N$_2$O$_2$

In a 10 mL round-bottomed flask, (2S,3S,4S)-2-(3-chloro-2-fluorophenyl)-3-(4-chloro-2-fluorophenyl)-4-neopentylpyrrolidine-3-carbonitrile (200 mg, 0.47 mmol), methyl 2-bromoacetate (159 mg, 1.04 mmol), K$_2$CO$_3$ and KOH (58.3 mg, 1.04 mmol) were combined with CH$_2$Cl$_2$ (5 mL) to give a brown suspension.

The reaction mixture was and stirred at rt for 3 h. The RM was dilute with CH$_2$Cl$_2$, washed with water, brine, dried over Na$_2$SO$_4$ and concentrated. The crude material was purified by flash chromatography (1-20% of EtOA in hexanes) to give rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid methyl ester as a white amorphous solid (121.3 mg, 51.8%).

Example 41

Preparation of rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid

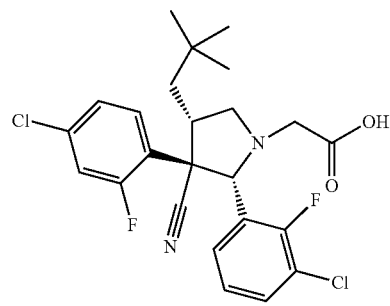

M. W. 481.37 C$_{24}$H$_{24}$Cl$_2$F$_2$N$_2$O$_2$

In a manner similar to the method described in Example 8, rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid methyl ester (115 mg, 0.23 mmol) in THF/MeOH (1.8/0.6 mL) was treated with 2N KOH (0.6 mL) at rt overnight to give rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid (108.5 mg, 97.0%).

Example 42

Preparation of rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-benzoic acid methyl ester

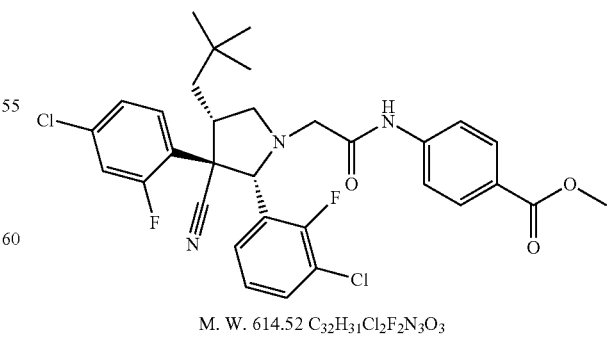

M. W. 614.52 C$_{32}$H$_{31}$Cl$_2$F$_2$N$_3$O$_3$

In a manner similar to the method described in Example 11, rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid (48.2 mg, 0.10 mmol) was reacted with 4-amino-benzoic acid methyl ester (30.2 mg, 0.20 mmol), in the presence of HATU (57.0 mg, 0.15 mmol) and iPr$_2$NEt (0.03 mL) in CH$_2$Cl$_2$ (2 mL) at rt for 2 hrs to give rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid methyl ester as a white solid (39.6 mg, 64.5%).

Example 43

Preparation of rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-benzoic acid

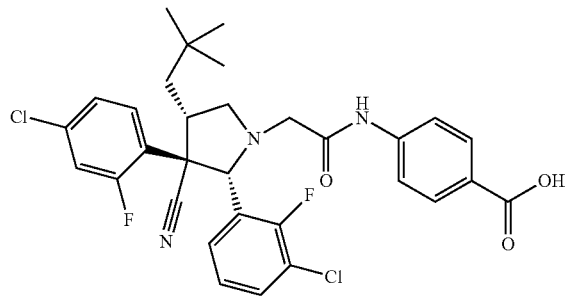

M. W. 600.50 C$_{31}$H$_{29}$Cl$_2$F$_2$N$_3$O$_3$

To a mixture of rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-benzoic acid methyl ester (30.0 mg, 0.05 mmol) in THF/MeOH (0.6 mL/0.2 mL) was added 2 N LiOH (0.2 mL), and the reaction mixture was stirred at rt for 2 hrs. The reaction mixture was concentrated and quenched with 2 NH$_2$SO$_4$, extracted with EtOAc, and washed with water, brine. The organic phase was separated, and dried over Na$_2$SO$_4$. The mixture was then concentrated to give rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-benzoic acid (29.0 mg, 98.9%). LC-MS (ES$^+$) m/z Calcd for C$_{31}$H$_{29}$Cl$_2$F$_2$N$_3$O$_3$+H [(M+H): 600.5; Found: 602.

Example 44

Preparation of rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid methyl ester

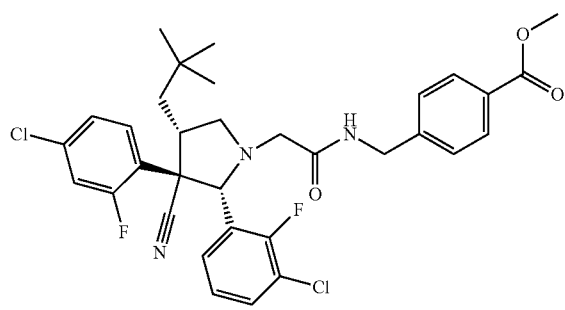

M. W. 628.6 C$_{33}$H$_{33}$Cl$_2$F$_2$N$_3$O$_3$

In a manner similar to the method described in Example 11, rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid (48.2 mg, 0.10 mmol) prepared in Example 31 was reacted with methyl 4-(aminomethyl)benzoate hydrochloride (24.2 mg, 0.12 mmol), in the presence of HATU (38.0 mg, 0.10 mmol) and iPr$_2$NEt (0.04 mL, 0.24 mmol) in CH$_2$Cl$_2$ (2 mL) at rt for 2 hrs to give rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid methyl ester as a white amorphous (59.5 mg, 94.7%). HRMS (ES$^+$) m/z Calcd for C$_{33}$H$_{33}$Cl$_2$F$_2$N$_3$O$_3$+H [(M+H): 628.1940; Found: 628.1939.

Example 45

Preparation of rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid

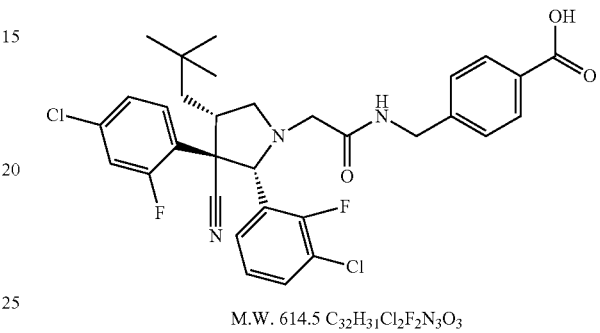

M.W. 614.5 C$_{32}$H$_{31}$Cl$_2$F$_2$N$_3$O$_3$

To a mixture of rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid methyl ester (50.0 mg, 0.08 mmol) in THF/MeOH (0.6 mL/0.2 mL) was added 2 N LiOH (0.2 mL), and the reaction mixture was stirred at rt for 2 hrs. The reaction mixture was concentrated and quenched with 2 NH$_2$SO$_4$, extracted with EtOAc, and washed with water, brine. The organic phase was separated, and dried over Na$_2$SO$_4$. The mixture was then concentrated to give rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid (48.8 mg, 99.8%). HRMS (ES$^+$) m/z Calcd for C$_{32}$H$_{31}$Cl$_2$F$_2$N$_3$O$_3$+H [(M+H): 614.1784; Found: 614.1783.

Example 46

Preparation of rac-2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-N—((S)-3,4-dihydroxy-butyl)-acetamide

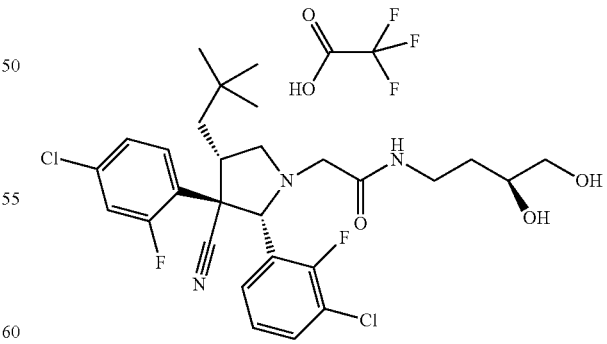

M. W. 568.50/682.5 C$_{28}$H$_{33}$Cl$_2$F$_2$N$_3$O$_3$/C$_2$HF$_2$O

In a manner similar to the method described in Example 11, rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid (48.2 mg, 0.10 mmol) was reacted with 2-((S)-2,2-dimethyl-[1,3]dioxolan-4-yl)-ethylamine (Example 4, 87.1 mg, 0.30 mmol), in the presence of HATU (72.0 mg, 0.20 mmol) and iPr₂NEt (0.1 mL) in CH₂Cl₂ (2 mL) at rt for 2 hrs to give 2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-N-[2-((S)-2,2-dimethyl-[1,3]dioxolan-4-yl)-ethyl]-acetamide (58.2 mg, 95.7%) which was used in the next step without further purification.

2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-N-[2-((S)-2,2-dimethyl-[1,3]dioxolan-4-yl)-ethyl]-acetamide (50 mg, 0.08 mmol) was diluted with MeOH and treated with PPTS (cat.) at 120° C. for 5 min with CEM microwave reactor. The reaction mixture was concentrated and diluted with CH₂Cl₂ and washed with water and brine. The organic phase was separated, filtered and dried over Na₂SO₄. The mixture was then concentrated and purified by RP-HPLC to give 2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-N—((S)-3,4-dihydroxy-butyl)-acetamide TFA salt (28.8 mg, 51.3%) as a white amorphous solid. HRMS (ES⁺) m/z Calcd for C₂₈H₃₃Cl₂F₂N₃O₃+H [(M+H)+]: 568.1940; Found: 568.1936.

Example 47

Preparation of rac-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid ethyl ester

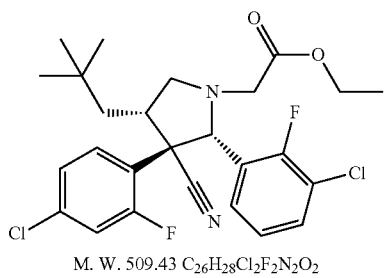

M. W. 509.43 C₂₆H₂₈Cl₂F₂N₂O₂

To a solution of rac (2S,3S,4S)-2-(3-chloro-2-fluoro-phenyl)-3-(4-chloro-2-fluoro-phenyl)-4-(2,2-dimethyl-propyl)-pyrrolidine-3-carbonitrile (42.1 mg, 0.10 mmol) in DMF (3 mL) was added potassium carbonate (43.3 mg, 0.313 mmol) and the reaction mixture was stirred at rt under argon for 21 hrs. The reaction mixture was diluted with ethyl acetate and washed with water (2×) and brine. The organic phase was separated, filtered and dried over Na₂SO₄. The mixture was then concentrated and purified by flash chromatography to give rac [(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid ethyl ester (22.3 mg, 44.2%,) as a white amorphous solid. HRMS (ES⁺) m/z Calcd for C₂₆H₂₈Cl₂F₂N₂O₂+H [(M+H)+]: 509.1569; Found: 509.1569.

Example 48

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid pyridin-4-ylamide

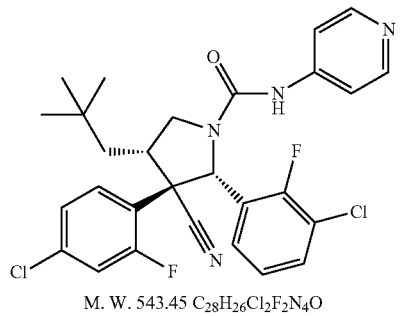

M. W. 543.45 C₂₈H₂₆Cl₂F₂N₄O

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (39.4 mg, 0.093 mmol) and 4-isocyanatopyridine (Princeton, 27.8 mg, 0.231 mmol) in CH₂Cl₂ (5 mL) was stirred at rt for 7.5 hrs then more 4-isocyanatopyridine (Princeton, 23.6 mg, 0.196 mmol) was added. After and additions 16 hrs, the reaction mixture was then concentrated and purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid pyridin-4-ylamide (45.3 mg, 89.5%). HRMS (ES⁺) m/z Calcd for C₂₈H₂₆Cl₂F₂N₄O+H [(M+H)+]: 543.1525; Found: 543.1525.

Example 49

Preparation of rac-2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid methyl ester

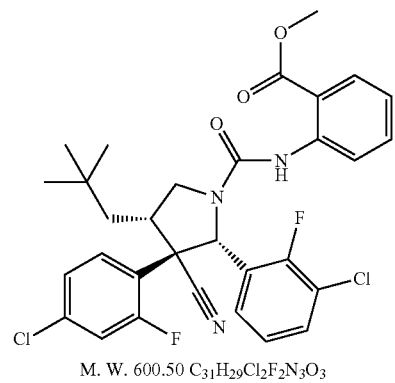

M. W. 600.50 C₃₁H₂₉Cl₂F₂N₃O₃

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (70.3 mg, 0.166 mmol) and methyl 2-isocyanatobenzoate (Aldrich, 150.7 mg, 0.851 mmol) in CH₂Cl₂ (9 mL) was stirred at rt for 18 hrs. The reaction mixture was then concentrated and purified by flash column to give rac-2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid methyl ester (67.9 mg, 68.1%). HRMS (ES⁺) m/z Calcd for $C_{31}H_{29}Cl_2F_2N_3O_3$+Na [(M+Na): 622.1446; Found: 622.1449.

Example 50

Preparation of rac-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid

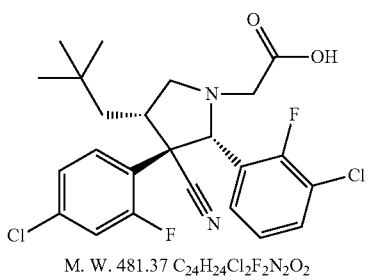

M. W. 481.37 $C_{24}H_{24}Cl_2F_2N_2O_2$

To a mixture of rac [(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid ethyl ester (14.7 mg, 0.0288 mmol, Example C1) in THF (1.8 mL) was added a solution of LiOH (Aldrich, 8.5 mg, 0.02 mmol) in water (1.2 mL) and the reaction mixture was stirred at rt for 22 hrs. The reaction mixture was partly concentrated and quenched with 1 N HCl (pH 4-5), extracted with EtOAc, and washed with water, saturated NaCl. The organic phase was separated, and dried over $Na_2SO_4$. The mixture was then concentrated to give rac-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid (14.2 mg, 102%). HRMS (ES⁺) m/z Calcd for $C_{24}H_{24}Cl_2F_2N_2O_2$+H [(M+H)+]: 481.1256; Found: 481.1255.

Example 51

Preparation of 2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid

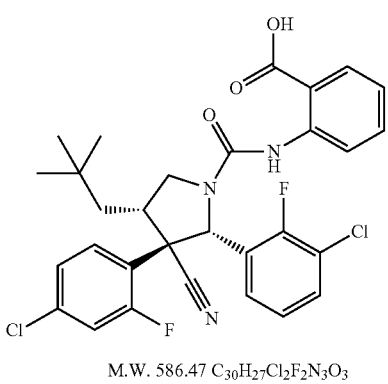

M.W. 586.47 $C_{30}H_{27}Cl_2F_2N_3O_3$

To a mixture of rac-2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-benzoic acid methyl ester (53.0 mg, 0.0883 mmol, Example C3) in THF (3 mL) was added a solution of LiOH (Aldrich, 21.8 mg, 0.52 mmol) in water (2 mL) and the reaction mixture was stirred at rt for 23 hrs. The reaction mixture was partly concentrated and quenched with 1 N HCl (pH 4-5), extracted with EtOAc, and washed with water, saturated NaCl. The organic phase was separated, and dried over $Na_2SO_4$. The mixture was then concentrated to give 2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid (49.1 mg, 95%). HRMS (ES⁺) m/z Calcd for $C_{30}H_{27}Cl_2F_2N_3O_3$+H [(M+H)+]: 586.1471; Found: 586.1474.

Example 52

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-fluoro-phenyl)-amide

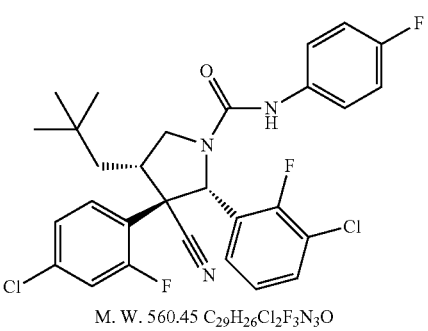

M. W. 560.45 $C_{29}H_{26}Cl_2F_3N_3O$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (43.1 mg, 0.102 mmol) and 4-fluorophenyl isocyanate (Aldrich, 71.0 mg, 0.512 mmol) in $CH_2Cl_2$ (5 mL) was stirred at rt for 24 hrs. The reaction mixture was then concentrated and purified by flash column to give (2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-fluoro-phenyl)-amide (45.6 mg, 79.8%). HRMS (ES⁺) m/z Calcd for $C_{29}H_{26}Cl_2F_3N_3O$+H [(M+H)+]: 560.1478; Found: 560.1479.

Example 53

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methylsulfanyl-phenyl)-amide

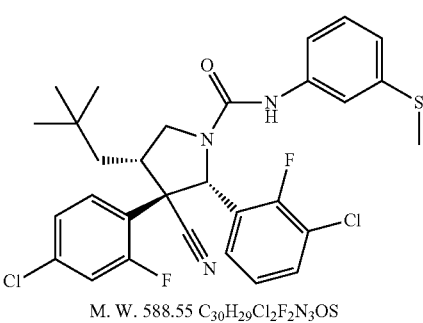

M. W. 588.55 $C_{30}H_{29}Cl_2F_2N_3OS$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (59.9 mg, 0.142 mmol) and 3-methyl(thio)phenyl isocyanate (Aldrich, 117.0 mg, 0.711 mmol) in $CH_2Cl_2$ (7 mL) was stirred at rt for 72 hrs. The reaction mixture was then concentrated and purified by flash column to give rac-(2S,3S,4S)-2-(3-chloro-2-fluoro-phenyl)-3-(4- chloro-2-fluoro-phenyl)-3-cyano-4-(2,2-dimethyl-propyl)-pyrrolidine-1-carboxylic acid (3-methylsulfanyl-phenyl)-amide (67.7 mg, 81%). HRMS (ES+) m/z Calcd for $C_{30}H_{29}Cl_2F_2N_3OS+H$ [(M+H)+]: 588.1449; Found: 588.1452.

Example 54

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methanesulfonyl-phenyl)-amid

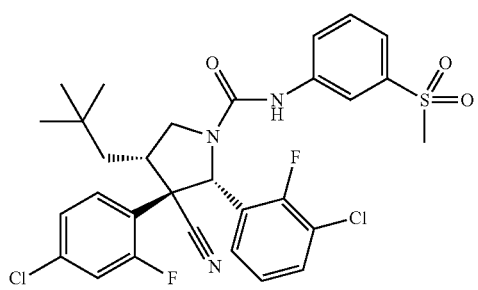

M. W. 620.55 $C_{30}H_{29}Cl_2F_2N_3O_3S$

A mixture of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methylsulfanyl-phenyl)-amide (Example 53) in CHCl₃ (4 mL) was stirred at 0° C. for 30 min then at rt for 80 min. The reaction mixture was extracted with EtOAc, and washed with water, saturated NaCl. The organic phase was separated, and dried over Na₂SO₄. to give rac-(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carboxylic acid (3-methanesulfonyl-phenyl)-amide (67.7 mg, 81%). HRMS (ES+) m/z Calcd for $C_{30}H_{29}Cl_2F_2N_3O_3S+H$ [(M+H)+]: 642.1167; Found: 642.1169.

Example 55

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid pyridin-3-ylamide

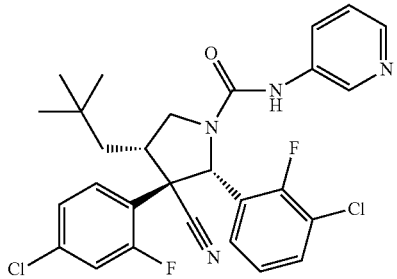

M.W. 543.45 $C_{28}H_{26}Cl_2F_2N_4O$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (40 mg, 0.095 mmol) and 3-isocyanatopyridine (Oakwood, 29.1 mg, 0.242 mmol) in CH₂Cl₂ (5 mL) was stirred at rt for 17 hrs. The reaction mixture was then purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid pyridin-3-ylamide (15.5 mg, 30%).

HRMS (ES+) m/z Calcd for $C_{28}H_{26}Cl_2F_2N_4O+H$ [(M+H)+]: 543.1525; Found: 543.1527.

Example 56

Preparation of rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid ethyl ester

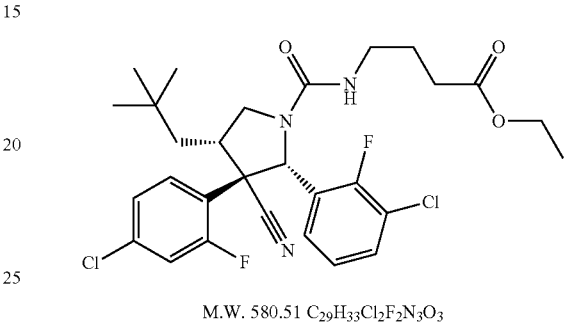

M.W. 580.51 $C_{29}H_{33}Cl_2F_2N_3O_3$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (101 mg, 0.239 mmol) and ethyl 4-iaocyanatobutyrate (Aldrich, 196 mg, 1.25 mmol) in CH₂Cl₂ (10 mL) was stirred at rt for 22 hrs. The reaction mixture was then purified by flash column to give rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid ethyl Ester (121.8 mg, 87.8%). HRMS (ES+) m/z Calcd for $C_{29}H_{33}Cl_2F_2N_3O_3+H$ [(M+H)+]: 602.1759; Found: 602.1756.

Example 57

Preparation of rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid

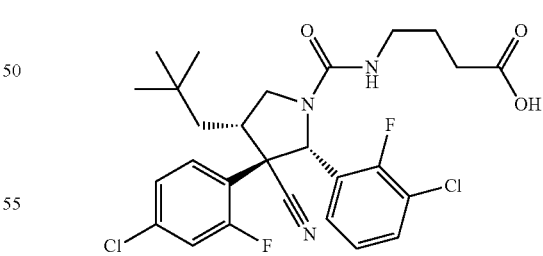

M.W. 552.45 $C_{27}H_{29}Cl_2F_2N_3O_3$

To a mixture rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid ethyl ester (98.6 mg, 0.170 mmol, Example C10) in THF (6 mL) was added a solution of LiOH (Aldrich, 47.1 mg, 1.12 mmol) in water (4 mL) and the reaction mixture was stirred at rt for 6 hrs. The reaction mixture was partly concentrated and quenched with 1 N HCl (pH 4-5), extracted with EtOAc, and washed with water, saturated NaCl. The organic phase was separated, and dried over Na₂SO₄. The mixture was then concentrated to give rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid (93.9 mg, 100%). HRMS (ES⁺) m/z Calcd for C₂₇H₂₉Cl₂F₂N₃O₃+H [(M+H)+]: 552.1627; Found: 552.1628.

Example 58

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-carbamoyl-propyl)-amide

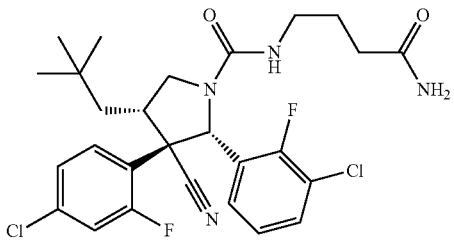

M.W. 551.47 C₂₇H₃₀Cl₂F₂N₄O₂

To a mixture rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid (22.7 mg, 0.041 mmol, Example C11) in N,N-dimethyl formamide (2.5 mL) was added DIPEA (37.1 mg, 0.287 mmol) and HATU (25.1 mg, 0.066 mmol). After it was stirred at rt for 35 min, ground ammonium chloride (5.1 mg, 0.095 mmol,) was added. After 3 hrs the reaction mixture was extracted with EtOAc, and washed with water, 10% ammonium chloride, saturated sodium bicarbonate, water, and saturated NaCl. The organic phase was separated, and dried over Na₂SO₄. The reaction mixture was then purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-carbamoyl-propyl)-amide (19.4 mg, 85.6%). HRMS (ES⁺) m/z Calcd for C₂₇H₃₀Cl₂F₂N₄O₂+Na [(M+Na): 573.1606; Found: 573.1609.

Example 59

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methylcarbamoyl-propyl)-amide

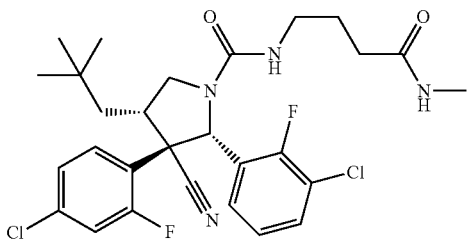

M.W. 565.50 C₂₈H₃₂Cl₂F₂N₄O₂

To a mixture rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid (24.0 mg, 0.043 mmol, Example 58) in N,N-dimethyl formamide (2.5 mL) was added DIPEA (48.2 mg, 0.373 mmol), HoBt (12.2 mg, 0.090 mmol), HBTU (30.7 mg, 0.081 mmol) and methylamine hydrochloride (9.6 mg, 0.142 mmol). After it was stirred at rt for 5.5 hrs, the solvent was removed and the reaction mixture was extracted with EtOAc, and washed with 1N sodium hydroxide (2×), water, and saturated NaCl. The organic phase was separated, and dried over Na₂SO₄. The reaction mixture was then purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methylcarbamoyl-propyl)-amide (23.0 mg, 93.7%). HRMS (ES⁺) m/z Calcd for C₂₈H₃₂Cl₂F₂N₄O₂+H [(M+H)+]: 565.1943; Found: 565.1944.

Example 60

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (1-methanesulfonyl-piperidin-4-yl)-amide

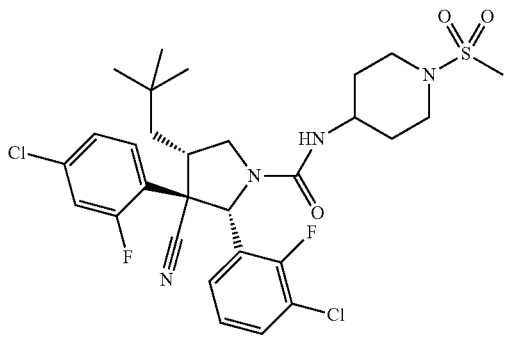

M.W. 627.59 C₂₉H₃₄Cl₂F₂N₄O₃S

To a mixture of 1-methanesulfonyl-piperidin-4-ylamine; compound with trifluoro-acetic acid (229.4 mg, 0.785 mmol, US20060014708) in N,N-dimethyl formamide (4.0 mL) was added TEA (101 mg, 1.004 mmol) and 1,1'-carbonyldiimidazole (Aldrich, 134 mg, 0.826 mmol). After it was stirred at rt for 2 hrs, the solvent was removed and the reaction mixture was extracted with EtOAc, and washed with water (2×), and saturated NaCl. The organic phase was separated, dried over Na₂SO₄, filtered and concentrated to give imidazole-1-carboxylic acid (1-methanesulfonyl-piperidin-4-yl)-amide (150.7 mg, 70.5%) which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (30.5 mg, 0.072 mmol) and imidazole-1-carboxylic acid (1-methanesulfonyl-piperidin-4-yl)-amide (75.4 mg, 0.277 mmol) in CH₂Cl₂ (4 mL) was stirred at rt for 72 hrs. The reaction mixture was then purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (1-methanesulfonyl-piperidin-4-yl)-amide (15.7 mg, 34.7%). HRMS (ES⁺) m/z Calcd for C₂₉H₃₄Cl₂F₂N₄O₃S+H [(M+H)+]: 627.1770; Found: 627.1770.

Example 61

Preparation of rac-2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetamide

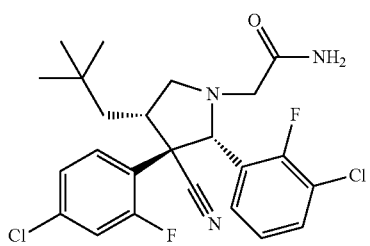

M.W. 480.39 C$_{24}$H$_{25}$Cl$_2$F$_2$N$_3$O

To a mixture rac-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid (23.0 mg, 0.048 mmol, Example 51) in N,N-dimethyl formamide (2.5 mL) was added DIPEA (44.5 mg, 0.344 mmol) and HATU (29.6 mg, 0.078 mmol). After it was stirred at rt for 22 min, ground ammonium chloride (6.4 mg, 0.12 mmol,) was added. After 3 hrs the reaction mixture was extracted with EtOAc, and washed with water, 10% ammonium chloride, saturated sodium bicarbonate, water, and saturated NaCl. The organic phase was separated, and dried over Na$_2$SO$_4$. The reaction mixture was then purified by flash column to give rac-2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetamide (3.7 mg, 16.1%). HRMS (ES$^+$) m/z Calcd for C$_{24}$H$_{25}$Cl$_2$F$_2$N$_3$O+Na [(M+Na): 502.1235; Found: 502.1235.

Example 62

Preparation of rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid ethyl ester

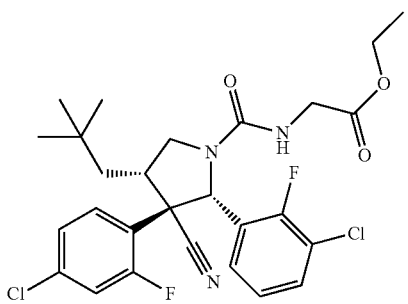

MW. 552.45 C$_{27}$H$_{29}$Cl$_2$F$_2$N$_3$O$_3$

In a manner similar to the method described in Example C3, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (80 mg, 0.189 mmol) was reacted with isocyanato-acetic acid ethyl ester (122 mg, 0.945 mmol) to give rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid ethyl ester (91.2 mg, 87%). HRMS (ES$^+$) m/z Calcd for C$_{27}$H$_{29}$Cl$_2$F$_2$N$_3$O$_3$+H [(M+H)+]: 552.1627; Found: 552.1629.

Example 63

Preparation of rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid

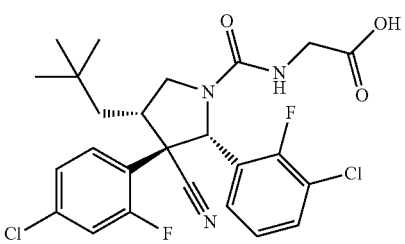

M.W. 524.40 C$_{25}$H$_{25}$Cl$_2$F$_2$N$_3$O$_3$

In a manner similar to the method described in Example 52, rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid ethyl ester (83 mg, 0.144 mmol, example C16) was reacted with lithium hydroxide hydrate (36 mg, 0.945 mmol, Aldrich) to give rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid (71 mg, 92%) HRMS (ES$^+$) m/z Calcd for C$_{25}$H$_{25}$Cl$_2$F$_2$N$_3$O$_3$+H [(M+H)+]: 524.1314; Found: 524.1315.

Example 64

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid methylcarbamoylmethyl-amide

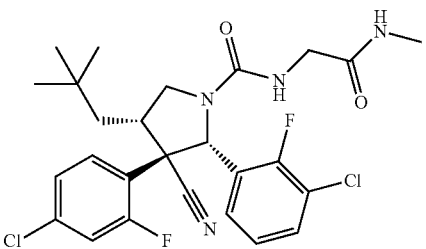

M.W. 537.44 C$_{26}$H$_{28}$Cl$_2$F$_2$N$_4$O$_2$

In a manner similar to the method described in Example 60, a mixture of rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid (22.6 mg, 0.0432 mmole, example 64) was reacted with a solution of methylamine (0.04 mL, 2M in THF, 0.080 mmol, Aldrich) to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid methylcarbamoylmethyl-amide (17.9 mg, 77%) as a white solid. HRMS (ES+) m/z Calcd for C26H28Cl2F2N4O2+H [(M+H)+]: 537.1630; Found: 537.1630.

Example 65

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid carbamoylmethyl-amide

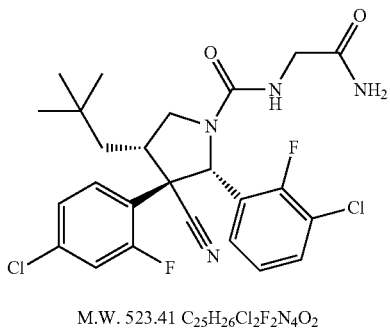

M.W. 523.41 C25H26Cl2F2N4O2

To a mixture rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid (25.4 mg, 0.048 mmol, example 17) in N,N-dimethyl formamide (2.5 mL) was added DIPEA (44.5 mg, 0.344 mmol) and HATU (30.3 mg, 0.080 mmol). After it was stirred at rt for 22 min, ground ammonium chloride (6.6 mg, 0.12 mmol,) was added. After 3 hrs the reaction mixture was extracted with EtOAc, and washed with water, 10% ammonium chloride, saturated sodium bicarbonate, water, and saturated NaCl. The organic phase was separated, and dried over Na2SO4. The reaction mixture was then purified by flash column to give rac-2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetamide (16.3 mg, 64.3%).

HRMS (ES+) m/z Calcd for C25H26Cl2F2N4O2+Na [(M+Na): 545.1293; Found: 545.1294.

Example 66

Preparation of rac-(2S,3S,4S)-2-(3-chloro-2-fluoro-phenyl)-3-(4-chloro-2-fluoro-phenyl)-4-(2,2-dimethyl-propyl)-1-(pyridine-3-sulfonyl)-pyrrolidine-3-carbonitrile

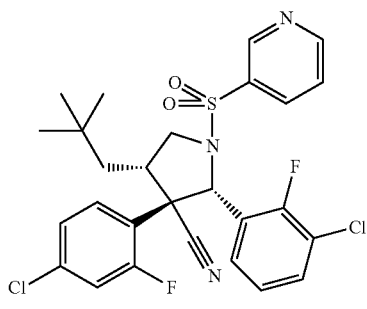

M.W. 564.49 C27H25Cl2F2N3O2S

To a mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (30.2 mg, 0.071 mmol) in CH2Cl2 (3 mL) was added DIPEA (29.7 mg, 0.230 mmol) and pyridine-3-sulfonyl chloride hydrochloride (22.8 mg, 0.106 mmol, Acme Bioscience). It was stirred at rt for 3 hrs under argon. More DIPEA (29.7 mg, 0.230 mmol) and pyridine-3-sulfonyl chloride hydrochloride (Acme Bioscience, 25.2 mg, 0.118 mmol) were added. After 4 hrs the reaction mixture was extracted with EtOAc, washed with water, saturated sodium bicarbonate, water, and saturated NaCl. The organic phase was separated, and dried over Na2SO4. The reaction mixture was then purified by flash column to give rac (2S,3S,4S)-2-(3-chloro-2-fluoro-phenyl)-3-(4-chloro-2-fluoro-phenyl)-4-(2,2-dimethyl-propyl)-1-(pyridine-3-sulfonyl)-pyrrolidine-3-carbonitrile (20.3 mg, 50.4%). HRMS (ES+) m/z Calcd for C27H25Cl2F2N3O2S+H [(M+H)+]: 564.1086; Found: 564.1087.

Example 67

Preparation of rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid methyl ester

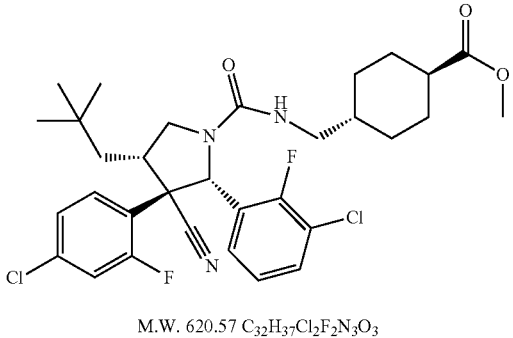

M.W. 620.57 C32H37Cl2F2N3O3

To a mixture of 4-aminomethyl-cyclohexanecarboxylic acid methyl ester (1.008 g, 4.758 mmol, Astatech,) in N,N-dimethyl formamide (20.0 mL) was added TEA (617 mg, 6.098 mmol) and 1,1'-carbonyldiimidazole (810.3 mg, 4.997 mmol, Aldrich,). After it was stirred at rt for 21 hrs under an argon atmosphere, the solvent was removed and the reaction mixture was extracted with EtOAc, and washed with water (2×), and saturated NaCl. The organic phase was separated, dried over Na2SO4, filtered and concentrated to give 4-{[(imidazole-1-carbonyl)-amino]-methyl}cyclohexanecarboxylic acid methyl ester (1.184 g, 4.46 mmol, 93%) which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (70.2 mg, 0.165 mmol) and 4-{[(imidazole-1-carbonyl)-amino]-methyl}cyclohexanecarboxylic acid methyl ester (509.6 mg, 1.921 mmol) in CH2Cl2 (9 mL) was stirred at rt for 17 hrs and at reflux for 7 hrs. The reaction mixture was then purified by flash column to give rac 4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid methyl ester (87.7 mg, 85.1%). HRMS (ES+) m/z Calcd for C32H37Cl2F2N3O3+H [(M+H)+]: 620.2253; Found: 620.2254.

Example 68

Preparation of rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid

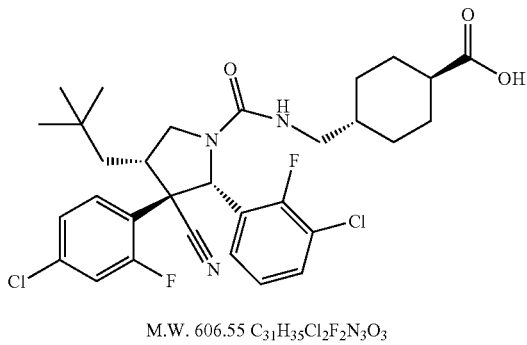

M.W. 606.55 $C_{31}H_{35}Cl_2F_2N_3O_3$

To a mixture of rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid methyl ester (65.0 mg, 0.105 mmol, example 21) in THF (4 mL) was added a solution of LiOH (Aldrich, 31.5 mg, 0.75 mmol) in water (2 mL) and the reaction mixture was stirred at rt for 6.5 hrs then more THF (2 mL) and water (1 mL) was added and stirred for 6 more hrs. The reaction mixture was partly concentrated and quenched with 1 N HCl (pH 5-6), extracted with EtOAc, and washed with water, saturated NaCl. The organic phase was separated, and dried over $Na_2SO_4$. The mixture was then concentrated to rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]amino}-methyl)-cyclohexanecarboxylic acid (95.8 mg, 100%). HRMS (ES$^+$) m/z Calcd for $C_{31}H_{35}Cl_2F_2N_3O_3$+H [(M+H)+]: 606.2097; Found: 606.2097.

Example 69

Preparation of rac-(2S,3S,4S)-2-(3-chloro-2-fluoro-phenyl)-3-(4-chloro-2-fluoro-phenyl)-4-(2,2-dimethyl-propyl)-1-(6-morpholin-4-yl-pyridine-3-sulfonyl)-pyrrolidine-3-carbonitrile

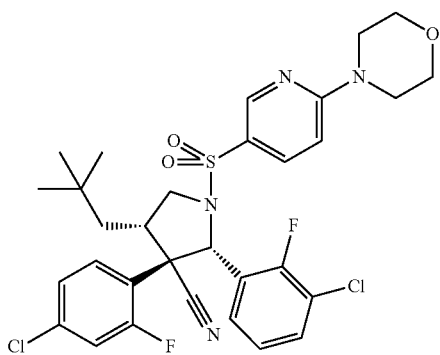

M.W. 649.59 $C_{31}H_{32}Cl_2F_2N_4O_3S$

To a mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (35.4 mg, 0.084 mmol) in $CH_2Cl_2$ (3 mL) was added DIPEA (44.5 mg, 0.344 mmol) and 6-morpholin-4-yl-pyridine-3-sulfonyl chloride (45.0 mg, 0.171 mmol, Maybridge). It was stirred at rt for 3.5 hrs under argon. More DIPEA (29.7 mg, 0.230 mmol) and 6-morpholin-4-yl-pyridine-3-sulfonyl chloride (18.7 mg, 0.071 mmol, Maybridge) were added. After 1.75 hrs the reaction mixture was extracted with EtOAc, washed with water, saturated sodium bicarbonate, water, and saturated NaCl. The organic phase was separated, and dried over $Na_2SO_4$. The reaction mixture was then purified by flash column to give rac-(2S,3S,4S)-2-(3-chloro-2-fluoro-phenyl)-3-(4-chloro-2-fluoro-phenyl)-4-(2,2-dimethyl-propyl)-1-(6-morpholin-4-yl-pyridine-3-sulfonyl)-pyrrolidine-3-carbonitrile (19.4 mg, 35.7%). HRMS (ES$^+$) m/z Calcd for $C_{31}H_{32}Cl_2F_2N_4O_3S$ H [(M+H)+]: 649.1613; Found: 649.1615.

Example 70

Preparation of rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-2-methoxy-benzoic acid methyl ester

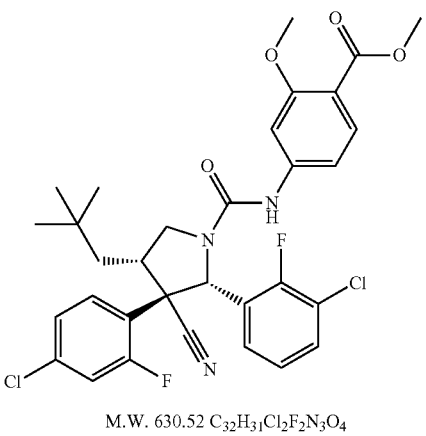

M.W. 630.52 $C_{32}H_{31}Cl_2F_2N_3O_4$

To a mixture of 4-amino-2-methoxy-benzoic acid methyl ester (1.000 g, 5.246 mmol, Maybridge) in N,N-dimethyl formamide (20.0 mL) was added 1,1'-carbonyldiimidazole (Aldrich, 919.8 mg, 5.502 mmol). After it was stirred at rt for 21 hrs under an argon atmosphere, the solvent was removed and the reaction mixture was extracted with EtOAc, and washed with water (2×), and saturated NaCl. The organic phase was separated, dried over $Na_2SO_4$, filtered and concentrated to give 4-[(imidazole-1-carbonyl)-amino]-2-methoxy-benzoic acid methyl ester (1.34 g, 4.87 mmol, 92.8%) which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (50.5 mg, 0.119 mmol) and 4-[(imidazole-1-carbonyl)-amino]-2-methoxy-benzoic acid methyl ester (325.2 mg, 1.181 mmol) in $CH_2Cl_2$ (8 mL) was stirred at reflux for 16 hrs. The reaction mixture was then purified by flash column to give rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-2-methoxy-benzoic acid methyl ester (48.5 mg, 64.6%). HRMS (ES$^+$) m/z Calcd for $C_{32}H_{31}Cl_2F_2N_3O_4$+H [(M+H)+]: 630.1733; Found: 630.1738.

Example 71

Preparation of rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid

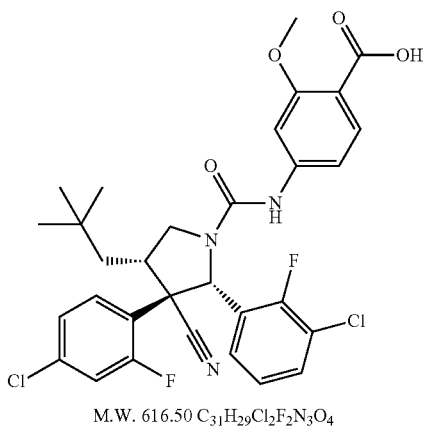

M.W. 616.50 $C_{31}H_{29}Cl_2F_2N_3O_4$

To a mixture of rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-2-methoxy-benzoic acid methyl ester (26.5 mg, 0.042 mmol, Example 70) in THF (2.4 mL) was added a solution of LiOH (Aldrich, 12.9 mg, 0.307 mmol) in water (1.2 mL) and the reaction mixture was stirred at rt for 16 hrs then more THF (3 mL) and water (1.5 mL) was added and stirred for 5 additional hrs at 50° C. The reaction mixture was partly concentrated and quenched with 1 N HCl (pH 5-7), extracted with EtOAc, and washed with water, saturated NaCl. The organic phase was separated, and dried over $Na_2SO_4$. The mixture was then concentrated to give rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid (25.7 mg, 99.2%). HRMS (ES$^+$) m/z Calcd for $C_{31}H_{29}O_2F_2N_3O_4$+H [(M+H)+]: 616.1576; Found: 616.1573.

Example 72

Preparation of rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid ethyl Ester

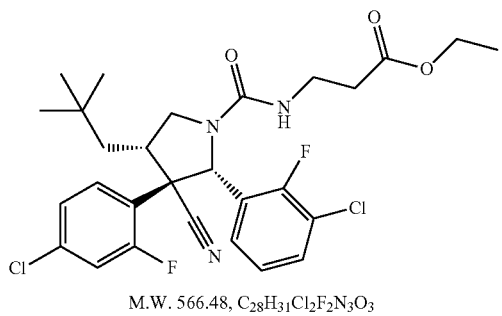

M.W. 566.48, $C_{28}H_{31}Cl_2F_2N_3O_3$

In a manner similar to the method described in Example 49, rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (100 mg, 0.236 mmol) was reacted with 3-isocyanato-propionic acid ethyl ester (168 mg, 1.174 mmol) to give rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid ethyl ester (113.2 mg, 85%). HRMS (ES$^+$) m/z Calcd for $C_{28}H_{31}Cl_2F_2N_3O_3$+H [(M+H)+]: 566.1784; Found: 566.1785.

Example 73

Preparation of rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid

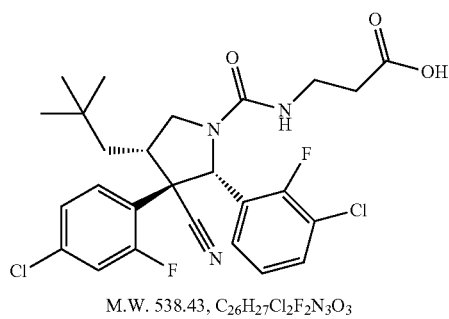

M.W. 538.43, $C_{26}H_{27}Cl_2F_2N_3O_3$

In a manner similar to the method described in Example 8, rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid ethyl ester (99 mg, 0.175 mmol, example 72) was reacted with lithium hydroxide hydrate (44 mg, 1.047 mmol, Aldrich) to give rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid (94 mg, 99%). HRMS (ES$^+$) m/z Calcd for $C_{26}H_{27}Cl_2F_2N_3O_3$+H [(M+H)+]: 538.1471; Found: 538.1470.

Example 74

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-methylcarbamoyl-ethyl)-amide

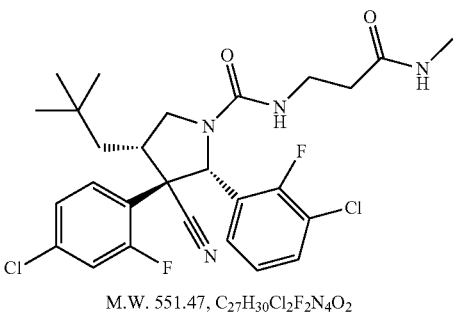

M.W. 551.47, $C_{27}H_{30}Cl_2F_2N_4O_2$

In a manner similar to the method described in Example 59, a mixture of rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid (24 mg, 0.0446 mmole, example 73) was reacted with a solution of methylamine (0.05 mL, 2M in THF, 0.10 mmol, Aldrich) to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-methylcarbamoyl-ethyl)- amide (17.2 mg, 70%) as a white solid. HRMS (ES⁺) m/z Calcd for C₂₇H₃₀Cl₂F₂N₄O₂+H [(M+H)+]: 551.1787; Found: 551.1789.

Example 75

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-dimethylcarbamoyl-ethyl)-amide

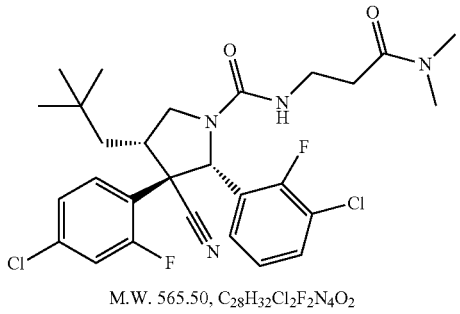

M.W. 565.50, C₂₈H₃₂Cl₂F₂N₄O₂

In a manner similar to the method described in Example 59, a mixture of rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid (24 mg, 0.0446 mmole, example 73) was reacted with a solution of dimethylamine (0.05 mL, 2M in THF, 0.10 mmol, Aldrich) to rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-dimethylcarbamoyl-ethyl)-amide (8.2 mg, 32%) as a white solid. HRMS (ES⁺) m/z Calcd for C₂₈H₃₂Cl₂F₂N₄O₂+H [(M+H)+]: 565.1943; Found: 565.1944.

Example 76

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-carbamoyl-ethyl)-amide

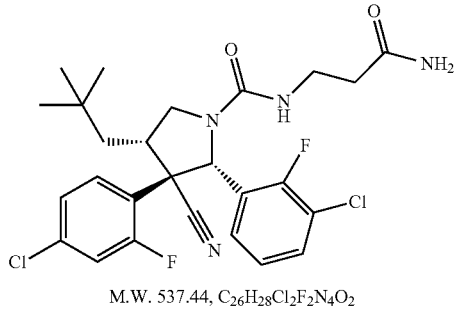

M.W. 537.44, C₂₆H₂₈Cl₂F₂N₄O₂

In a manner similar to the method described in Example 63, a mixture of rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid (25 mg, 0.0464 mmole, example 73), DIPEA (42 mg, 0.324 mmol) and HATU (26.4 mg, 0.069 mmol) in DMF was reacted with ammonium chloride (6.2 mg, 0.11 mmol) to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-carbamoyl-ethyl)-amide (14.1 mg, 57%). HRMS (ES⁺) m/z Calcd for C₂₆H₂₈Cl₂F₂N₄O₂+H [(M+H)+]: 537.1630; Found: 537.1630.

Example 77

Preparation of rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid ethyl ester

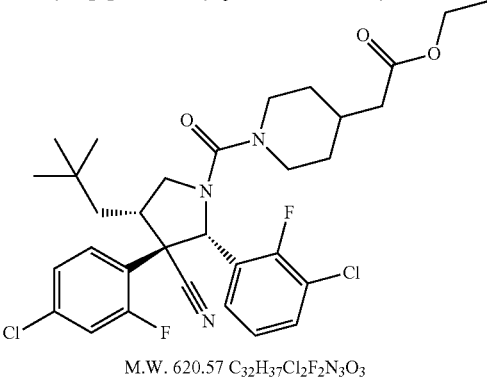

M.W. 620.57 C₃₂H₃₇Cl₂F₂N₃O₃

To a mixture of 2-(piperidin-4-yl)-acetic acid ethyl ester (211.4 mg, 1.234 mmol, Oakwood,) in N,N-dimethyl formamide (5.0 mL) was added 1,1'-carbonyldiimidazole (216 mg, 1.332 mmol Aldrich). After it was stirred at rt for 4 days under an argon atmosphere, the solvent was removed and the reaction mixture was extracted with EtOAc, and washed with water (2×), and saturated NaCl. The organic phase was separated, dried over Na₂SO₄, filtered and concentrated to give [1-(imidazole-1-carbonyl)-piperidin-4-yl]acetic acid ethyl ester (293.3 mg, 1.10 mmol, 89.6%) which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (51.6 mg, 0.122 mmol) and [1-(imidazole-1-carbonyl)-piperidin-4-yl]-acetic acid ethyl ester (293.3 mg, 1.10 mmol) in CH₂Cl₂ (8 mL) was stirred at reflux for 16 hrs then 1 h at 140° C. in a microwave tube and finally at 160° C. for 1 hr. The reaction mixture was then purified by flash column to give rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid ethyl ester (40.4 mg, 53.4%). HRMS (ES⁺) m/z Calcd for C₃₂H₃₇Cl₂F₂N₃O₃+H [(M+H)+]: 620.2253; Found: 620.2254.

Example 78

Preparation of rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid

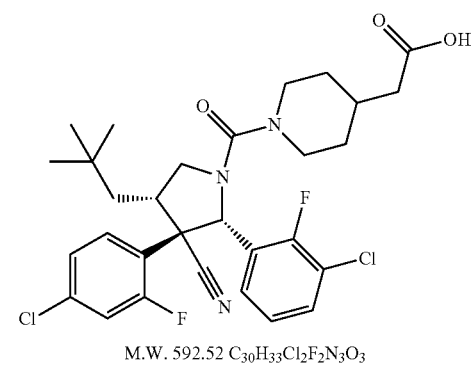

M.W. 592.52 C₃₀H₃₃Cl₂F₂N₃O₃

To a mixture of rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid ethyl ester (33.0 mg, 0.053 mmol) in THF (3 mL) was added a solution of LiOH (Aldrich, 15.7 mg, 0.374 mmol) in water (1.5 mL) and the reaction mixture was stirred at rt for 24 hrs. The reaction mixture was partly concentrated and quenched with 1 N HCl (pH 6-7), extracted with EtOAc, and washed with water, saturated NaCl. The organic phase was separated, and dried over $Na_2SO_4$. The mixture was then concentrated to give rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid (29.5 mg, 93.6%). HRMS (ES$^+$) m/z Calcd for $C_{30}H_{33}Cl_2F_2N_3O_3$+H [(M+H)+]: 592.1940; Found: 592.1940.

Example 79

Preparation of rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-propionic acid

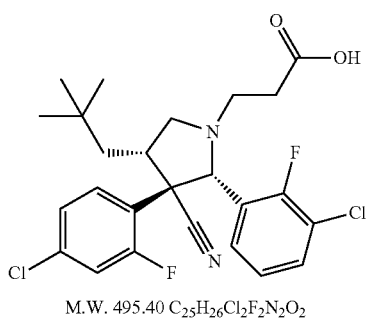

M.W. 495.40 $C_{25}H_{26}Cl_2F_2N_2O_2$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (30.6 mg, 0.0723 mmol), ethyl acrylate (73.7 mg, 0.728 mmol, Aldrich) and samarium(III) trifluoromethanesulfonate (34.9 mg, 0.0572 mmol) in THF (1.5 mL) were heated for 3 h at 160° C. in a microwave tube. The reaction mixture was then diluted with $CH_2Cl_2$, extracted with water, and saturated NaCl. The organic phase was separated, dried over $Na_2SO_4$, and purified by flash column to give rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-propionic acid ethyl ester (12.3 mg, 32.5%).

To a mixture of rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-propionic acid ethyl ester (12.3 mg, 0.0235 mmol) in THF (2 mL) was added a solution of LiOH (Aldrich, 6.7 mg, 0.16 mmol) in water (1 mL) and the reaction mixture was stirred at rt for 22 hrs. The reaction mixture was partly concentrated and quenched with 1 N HCl (pH 6-7), extracted with EtOAc, washed with water (2×), and saturated NaCl. The organic phase was separated, and dried over $Na_2SO_4$. The mixture was then concentrated to give rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-propionic acid (11 mg, 100%). HRMS (ES$^+$) m/z Calcd for $C_{25}H_{26}Cl_2F_2N_2O_2$+H [(M+H)+]: 495.1412; Found: 495.1413.

Example 80

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (6-chloro-pyridin-3-ylmethyl)-amide

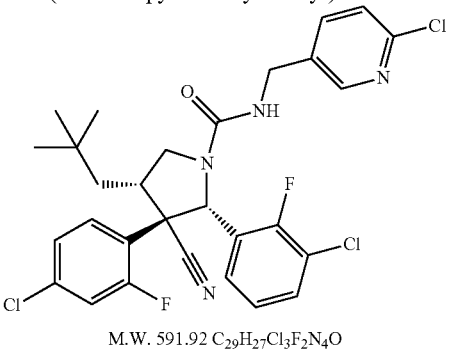

M.W. 591.92 $C_{29}H_{27}Cl_3F_2N_4O$

To a mixture of 5-aminomethyl-2-chloropyridine (194.5 mg, 1.323 mmol, Alfa Asear) in N,N-dimethyl formamide (5.0 mL) was added 1,1'-carbonyldiimidazole (236.5 mg, 1.415 mmol, Aldrich). After it was stirred at rt for 18 hrs under an argon atmosphere, the solvent was removed and the reaction mixture was extracted with EtOAc, washed with water (4×), and saturated NaCl. The organic phase was separated, dried over $Na_2SO_4$, filtered and concentrated to give [1-(imidazole-1-carbonyl)-piperidin-4-yl]acetic acid ethyl ester which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (56.5 mg, 0.133 mmol) and [1-(imidazole-1-carbonyl)-piperidin-4-yl]-acetic acid ethyl ester (1.32 mmol) in $CH_2Cl_2$ (8 mL) was stirred at rt for 4 days. The reaction mixture was then purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (6-chloro-pyridin-3-ylmethyl)-amide (70.1 mg, 89.0%). HRMS (ES$^+$) m/z Calcd for $C_{29}H_{27}Cl_3F_2N_4O$+H [(M+H)+]: 591.1292; Found: 591.1293.

Example 81

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (6-chloro-pyridin-3-yl)-amide

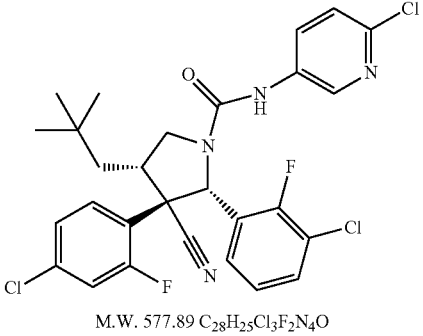

M.W. 577.89 $C_{28}H_{25}Cl_3F_2N_4O$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (60.8 mg, 0.144 mmol) and 2-chloro-5-isocyanatopyridine (109.1 mg, 0.144 mmol, Maybridge) in $CH_2Cl_2$ (6 mL) was stirred at rt for 16 hrs. The reaction mixture was then purified by flash column to give rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (6-chloro-pyridin-3-yl)-amide (59.1 mg, 71.1%). HRMS (ES+) m/z Calcd for C28H25Cl3F2N4O+H [(M+H)+]: 577.1135; Found: 577.1135.

Example 82

Preparation of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (1-methyl-2-oxo-1,2-dihydro-pyridin-4-yl)-amide

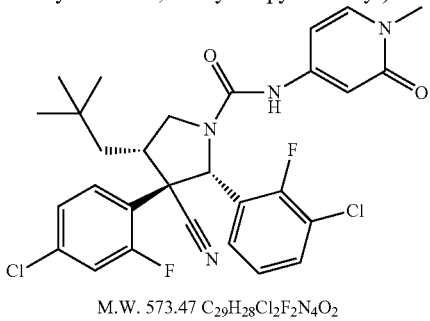

M.W. 573.47 C29H28Cl2F2N4O2

To a mixture of 4-amino-1-methyl-pyrin-2-one (149.5 mg, 1.180 mmol, MolBridge) in N,N-dimethyl formamide (4.0 mL) was added 1,1'-carbonyldiimidazole (208.5 mg, 1.247 mmol, Aldrich). After it was stirred at rt for 3 days under an argon atmosphere, a precipitate formed which was filtered, dissolved in EtOAc, washed with water, and saturated NaCl. The organic phase was separated, dried over Na2SO4, filtered and concentrated to give imidazole-1-carboxylic acid (1-methyl-2-oxo-1,2-dihydro-pyridin-4-yl)-amide which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (15.8 mg, 0.0373 mmol) and imidazole-1-carboxylic acid (1-methyl-2-oxo-1,2-dihydro-pyridin-4-yl)-amide (76.3 mg, 0.105 mmol) in CH2Cl2 (1.5 mL) was stirred at rt for 1 day. The reaction mixture was then purified by flash column to rac (2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (1-methyl-2-oxo-1,2-dihydro-pyridin-4-yl)-amide (19.7 mg, 92.1%). HRMS (ES+) m/z Calcd for C29H28Cl2F2N4O2+H [(M+H)+]: 573.1630; Found: 573.1629.

Example 83

Preparation of rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-sulfonyl]-benzoic acid

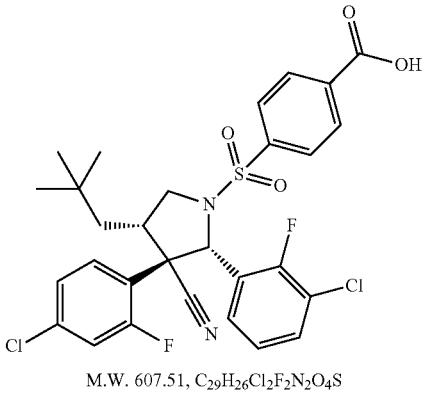

M.W. 607.51, C29H26Cl2F2N2O4S

To a mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (80 mg, 0.0189 mmol) and diisopropylethylamine (122 mg, 0.942 mmol) in CH2Cl2 (6 mL) was added p-(chlorosulfonyl)benzoic acid (70.0 mg, 0.283 mmol, Eastman) and the reaction mixture was stirred at room temp. for 6 hrs. The resulting mixture was diluted with EtOAc, washed with aqueous Na2CO3, 1N HCl and brine, and concentrated to dryness to give rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-sulfonyl]-benzoic acid (44.2 mg, 38%) as a white solid. HRMS (ES+) m/z Calcd for C29H26Cl2F2N2O4S H [(M+H)+]: 607.1031; Found: 607.1032.

Example 84

Preparation of rac-(2S,3S,4S)-2-(3-chloro-2-fluoro-phenyl)-3-(4-chloro-2-fluoro-phenyl)-1-(6-chloro-pyridine-3-sulfonyl)-4-(2,2-dimethyl-propyl)-pyrrolidine-3-carbonitrile

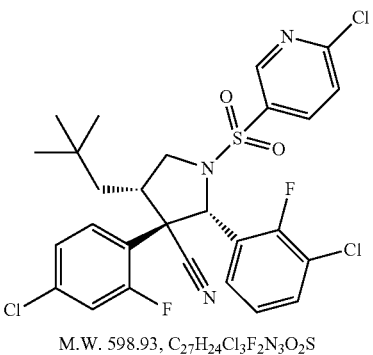

M.W. 598.93, C27H24Cl3F2N3O2S

In a manner similar to the method described in Example 83, a mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (82 mg, 0.0195 mmol) was reacted with 6-chloropyridine-3-sulfonyl chloride (66 mg, 0.311 mmol, Enamine) to give rac-(2S,3S,4S)-2-(3-chloro-2-fluoro-phenyl)-3-(4-chloro-2-fluoro-phenyl)-1-(6-chloro-pyridine-3-sulfonyl)-4-(2,2-dimethyl-propyl)-pyrrolidine-3-carbonitrile (116.6 mg, 97%) as a light yellow solid.

HRMS (ES+) m/z Calcd for C27H24Cl3F2N3O2S+H [(M+H)+]: 598.0696; Found: 598.0696.

Example 85

Preparation of rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-sulfonyl)-pyrrolidine-3-carbonitrile

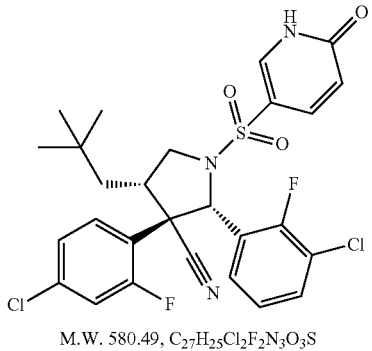

M.W. 580.49, C27H25Cl2F2N3O3S

A suspension of rac-(2S,3S,4S)-2-(3-chloro-2-fluoro-phenyl)-3-(4-chloro-2-fluoro-phenyl)-1-(6-chloro-pyridine-3-sulfonyl)-4-(2,2-dimethyl-propyl)-pyrrolidine-3-carbonitrile (24.4 mg, 0.041 mmol, example 37) in acetic acid (2 mL)

and water (2 mL) was heated at 220° C. for 1 hr in microwave condition. The solvent was removed in vacuum and the residue was taken up in EtOAc, washed with aqueous $Na_2CO_3$ and brine, dried and evaporated. The crude product was purified by flash column to give rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-sulfonyl)-pyrrolidine-3-carbonitrile (17.6 mg, 71%) as a white solid. HRMS (ES$^+$) m/z Calcd for $C_{27}H_{25}Cl_2F_2N_3O_3S$+H [(M+H)+]: 580.1035; Found: 580.1035.

Example 86

Preparation of rac-(2S,3S,4S)-2-(3-chloro-2-fluoro-phenyl)-3-(4-chloro-2-fluoro-phenyl)-1-(6-chloro-pyridine-3-carbonyl)-4-(2,2-dimethyl-propyl)-pyrrolidine-3-carbonitrile

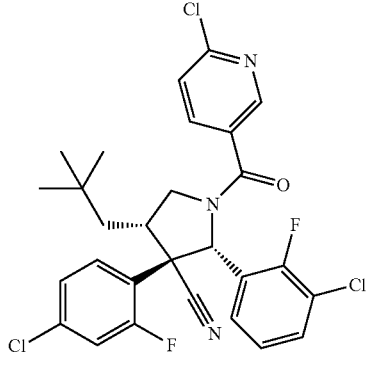

M.W. 562.88, $C_{28}H_{24}Cl_3F_2N_3O$

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (53 mg, 0.125 mmol), diisopropylethylamine (64.7 mg, 0.50 mmol), dimethylaminopyridine (3 mg, 0.024 mmol, Aldrich) in $CH_2Cl_2$ (6 mL) and 6-chloronicotinoyl chloride (41.0 mg, 0.232 mmol, Aldrich) was stirred at room temp. for 2 hrs before diluted with EtOAc, washed with aqueous $Na_2CO_3$, brine, and concentrated. The residue was purified by flash column to give rac-(2S,3S,4S)-2-(3-chloro-2-fluoro-phenyl)-3-(4-chloro-2-fluoro-phenyl)-1-(6-chloro-pyridine-3-carbonyl)-4-(2,2-dimethyl-propyl)-pyrrolidine-3-carbonitrile (58.3 mg, 83%) as a white solid. HRMS (ES$^+$) m/z Calcd for $C_{28}H_{24}Cl_3F_2N_3O$+H [(M+H)+]: 562.1026; Found: 562.1026

Example 87

Preparation of rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-carbonyl)-pyrrolidine-3-carbonitrile

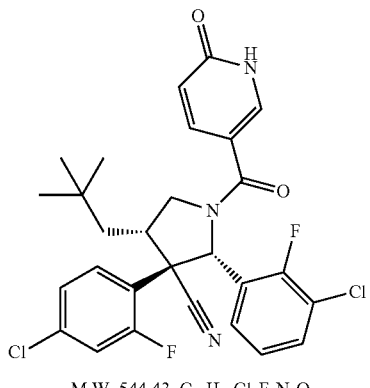

M.W. 544.43, $C_{28}H_{25}Cl_2F_2N_3O_2$

A suspension of rac-(2S,3S,4S)-2-(3-chloro-2-fluoro-phenyl)-3-(4-chloro-2-fluoro-phenyl)-1-(6-chloro-pyridine-3-carbonyl)-4-(2,2-dimethyl-propyl)-pyrrolidine-3-carbonitrile (63.9 mg, 0.113 mmol, example 39) in acetic acid (8 mL) and water (8 mL) was heated at 180° C. for 1 hr in microwave condition. The solvent was removed in vacuum and the residue was taken up in EtOAc, washed with aqueous $Na_2CO_3$ and brine, dried and evaporated. The crude product was purified by flash column to give rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-carbonyl)-pyrrolidine-3-carbonitrile (61.4 mg, 85%) as a white solid. HRMS (ES$^+$) m/z Calcd for $C_{28}H_{25}Cl_2F_2N_3O_2$+H [(M+H)+]: 544.1365; Found: 544.1364

Example 88

Preparation of rac-(2S,3S,4S)-2-(3-chloro-2-fluoro-phenyl)-3-(4-chloro-2-fluoro-phenyl)-4-(2,2-dimethyl-propyl)-1-(1-methyl-6-oxo-1,6-dihydro-pyridine-3-carbonyl)-pyrrolidine-3-carbonitrile

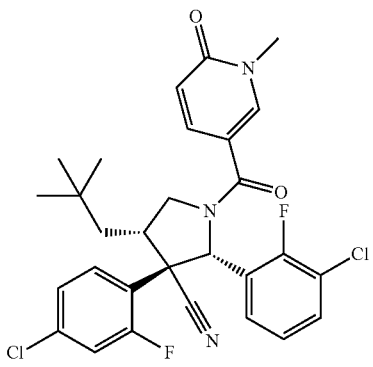

M.W. 558.46, $C_{29}H_{27}Cl_2F_2N_3O_2$

A mixture of rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-carbonyl)-pyrrolidine-3-carbonitrile (15.1 mg, 0.0277 mmol, example 40), cesium carbonate (27 mg, 0.0829 mmol, Aldrich) in DMF (3 mL) and iodomethane was stirred at room temp. for 3 hrs before it was diluted with EtOAc, washed with water and brine, dried and concentrated. The residue was purified by flash column to give rac-(2S,3S,4S)-2-(3-chloro-2-fluoro-phenyl)-3-(4-chloro-2-fluoro-phenyl)-4-(2,2-dimethyl-propyl)-1-(1-methyl-6-oxo-1,6-dihydro-pyridine-3-carbonyl)-pyrrolidine-3-carbonitrile (15.0 mg, 96%) as a white solid.

HRMS (ES$^+$) m/z Calcd for $C_{29}H_{27}Cl_2F_2N_3O_2$+H [(M+H)+]: 558.1521; Found: 558.1520

Example 89

Preparation of rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid methyl ester

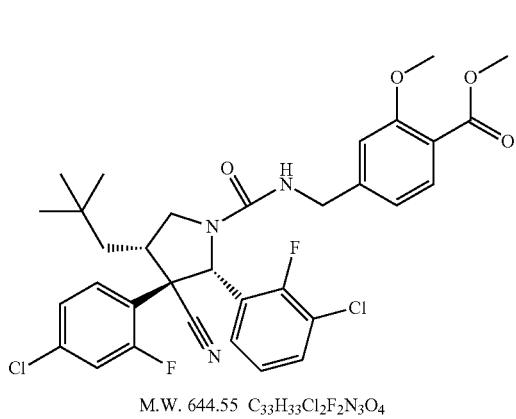

M.W. 644.55 C₃₃H₃₃Cl₂F₂N₃O₄

To a mixture of 4-cyano-2-methoxybenzoic acid (1.00 g, 5.648 mmol, Biogene) in methanol (15.0 mL) was added p-toluenesulfonic acid monohydrate (286 mg, 1.48 mmol, Aldrich) and it was heated to reflux under an argon atmosphere for 16 hrs. The solvent was removed and the reaction mixture was extracted with EtOAc, washed with saturated Na₂CO₃, water, and saturated NaCl. The organic phase was separated, dried over Na₂SO₄, filtered and concentrated to give 4-cyano-2-methoxy-benzoic acid methyl ester (1.04 g, 96.4%).

A mixture of 4-cyano-2-methoxy-benzoic acid methyl ester (1.01 g, 5.28 mmol) in methanol (50 mL) was added to Raney-nickel 2800 slurry in water (a few grams washed with methanol to remove the water, Aldrich) and it was put under a 50 psi hydrogen atmosphere for 16 hrs. The mixture was filtered through Celite under an argon atmosphere and concentrated and then purified by flash chromatography to give 4-aminomethyl-2-methoxy-benzoic acid methyl ester (385.7 mg, 34.7%).

To a mixture of 4-aminomethyl-2-methoxy-benzoic acid methyl ester (149 mg, 0.763 mmol) in N,N-dimethyl formamide (4.0 mL) was added 1,1'-carbonyldiimidazole (Aldrich, 127 mg, 0.762 mmol). After it was stirred at rt for 16 hrs under an argon atmosphere, the reaction mixture was extracted with EtOAc, and washed with water (2×), and saturated NaCl. The organic phase was separated, dried over Na₂SO₄, filtered and concentrated to give 4-{[(imidazole-1-carbonyl)-amino]-methyl}-2-methoxy-benzoic acid methyl ester (224.3 mg, 101% crude) which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (49.2 mg, 0.116 mmol) and 4-{[(imidazole-1-carbonyl)-amino]-methyl}-2-methoxy-benzoic acid methyl ester (224.3 mg, 0.775 mmol) in CH₂Cl₂ (8 mL) was stirred rt for 16 hrs. The reaction mixture was then purified by flash column to give rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid methyl ester (61.9 mg, 82.8%). HRMS (ES⁺) m/z Calcd for C₃₃H₃₃Cl₂F₂N₃O₄: 644.1889; Found: 644.1888

Example 90

Preparation of rac-4-(((2S,3S,4S)-2-(3-chloro-2-fluorophenyl)-3-(4-chloro-2-fluorophenyl)-3-cyano-4-neopentylpyrrolidine-1-carboxamido)methyl)-2-methoxybenzoic acid

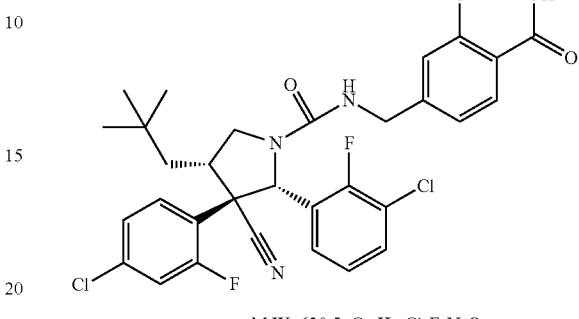

M.W. 630.5, C₃₀H₃₃Cl₂F₂N₃O₃

To a mixture of rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid methyl ester (52.1 mg, 0.0813 mmol, example 89) in THF (5 mL) was added a solution of LiOH (Aldrich, 25 mg, 0.595 mmol) in water (2.5 mL) and the reaction mixture was stirred at rt for 48 hrs. The reaction mixture was partly concentrated and quenched with 1 N HCl (pH 5), extracted with EtOAc, and washed with water, saturated NaCl. The organic phase was separated, and dried over Na₂SO₄. The mixture was then concentrated to give rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid (16.2 mg, 31.6%). LC-MS (ES⁺/⁻) m/z Calcd for C₃₀H₃₃Cl₂F₂N₃O₃+H [(M+H): 629; Found: 629.

Example 91

Preparation of rac-(2S,3S,4S)-2-(3-chloro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide

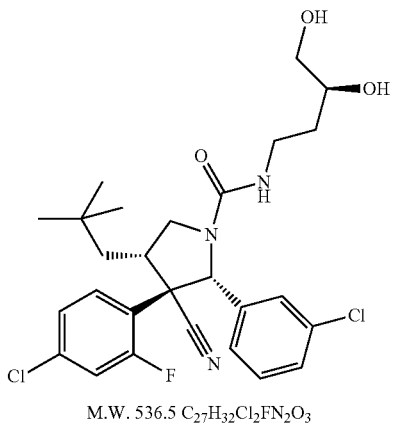

M.W. 536.5 C₂₇H₃₂Cl₂FN₂O₃

To a mixture of rac-(2S,3S,4S)-2-(3-chloro-phenyl)-3-(4-chloro-2-fluoro-phenyl)-4-(2,2-dimethyl-propyl)-pyrrolidine-3-carbonitrile (40.5 mg, 0.10 mmol) and triethylamine (TEA, 20.0 mg, 0.20 mmol) in CH₂Cl₂ (1 mL) was added phosgene solution (Aldrich, 20% in toluene, 0.12 mL, 0.12 mmol) by injection, and the reaction mixture was stirred at rt for 20 min. 2-((S)-2,2-dimethyl-[1,3]dioxolan-4-yl)-ethylamine (29.4 mg, 0.20 mmol) was then added. The reaction mixture was stirred at rt for another 30 min then concentrated to give the crude product (checked by LCMS) which was diluted with MeOH and treated with PPTS (cat.) at 120° C. for 5 min with CEM microwave reactor. The reaction mixture was concentrated and diluted with $CH_2Cl_2$ and washed with water and brine. The organic phase was separated, filtered and dried over $Na_2SO_4$. The mixture was then concentrated and purified by RP-HPLC to give rac-(2S,3S,4S)-2-(3-chloro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide (23.5 mg, 43.8%, 2 steps) as a white amorphous. HRMS (ES+) m/z Calcd for $C_{27}H_{32}Cl_2FN_3O_3$+H [(M+H)+]: 536.1878; Found: 536.1879.

Example 92

Preparation of rac-(2R,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid benzylamide

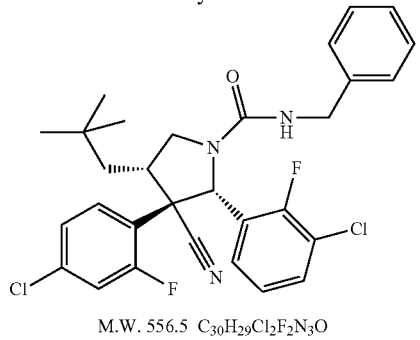

M.W. 556.5  $C_{30}H_{29}Cl_2F_2N_3O$

A mixture of rac-(2R,3S,4S)-2-(4-chloro-3-fluoro-phenyl)-3-(4-chloro-2-fluoro-phenyl)-3-cyano-4-(2,2-dimethyl-propyl)-pyrrolidine-3-carbonitrile (42.3 mg, 0.10 mmol) prepared in Example 3 and (isocyanatomethyl)benzene (Aldrich, 16.0 mg, 0.12 mmol) in $CH_2Cl_2$ (2 mL) was stirred at rt for 1 h. The reaction mixture was then concentrated and purified by flash column to give rac-(2R,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid benzylamide (46.8 mg, 84.2%) as a white solid HRMS (ES+) m/z Calcd for $C_{30}H_{29}Cl_2F_2N_3O$+H [(M+H): 556.1729; Found: 556.1725.

Example 93

Preparation of rac N-[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-benzamide

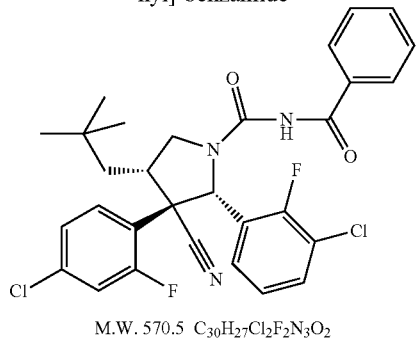

M.W. 570.5  $C_{30}H_{27}Cl_2F_2N_3O_2$

A mixture of rac-(2R,3S,4S)-2-(4-chloro-3-fluoro-phenyl)-3-(4-chloro-2-fluoro-phenyl)-3-cyano-4-(2,2-dimethyl-propyl)-pyrrolidine-3-carbonitrile (42.3 mg, 0.10 mmol) prepared in Example 3 and benzoyl isocyanate (Aldrich, 17.6 mg, 0.12 mmol) in $CH_2Cl_2$ (2 mL) was stirred at rt for 2 h. The reaction mixture was then concentrated and purified by flash column to give rac-(2R,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid benzylamide (52.1 mg, 91.4%) as a white solid HRMS (ES+) m/z Calcd for $C_{30}H_{27}Cl_2F_2N_3O_2$+H [(M+H): 570.1521; Found: 570.1521.

Example 94

Preparation of chiral 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid and chiral 4-({[(2R,3R,4R)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino})-methyl)-2-methoxy-benzoic acid

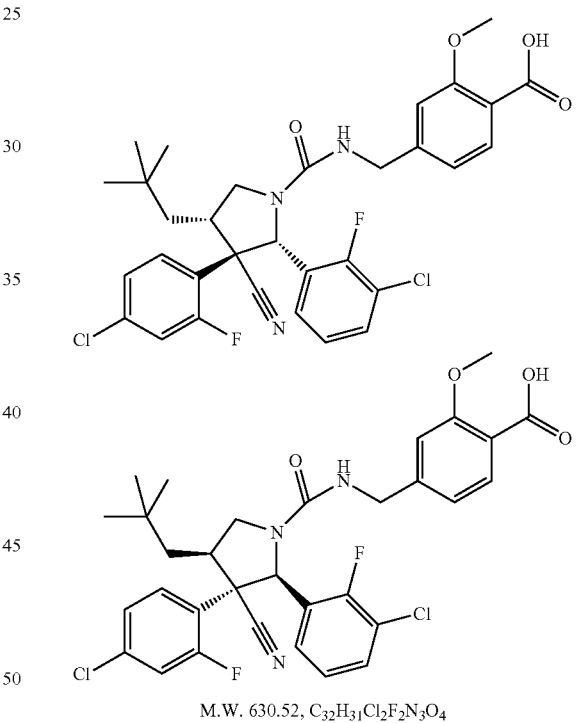

M.W. 630.52, $C_{32}H_{31}Cl_2F_2N_3O_4$

The mixture of rac-4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid was separated by SFC, 30% $CH_3OH$ on a Kromasil 5-CelluCoat OD prep column to give chiral 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid as a white lyophilized solid. MS (ES+) m/z Calcd: [(M+H)+]: 630.17, found: 630.2 and chiral 4-({[(2R,3R,4R)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid as a white lyophilized solid. MS (ES+) m/z Calcd: [(M+H)+]: 630.17, found: 630.2

Example 95

Preparation of 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid methyl ester

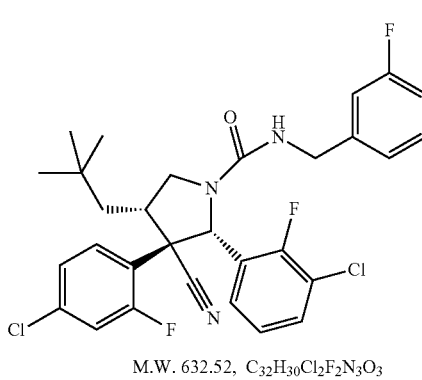

M.W. 632.52, $C_{32}H_{30}Cl_2F_2N_3O_3$

Preparation of methyl 4-(aminomethyl)-2-fluorobenzoate: A solution of 4-cyano-2-fluorobenzoic acid (4.02 g, 24.36 mmol, Aldrich) in methanol (50 mL) was treated with p-toluenesulfonic acid monohydrate (0.46 g, 2.43 mmol) and heated to reflux overnight. The solvent was removed and the reaction residue was extracted with EtOAc, washed with saturated $Na_2CO_3$, brine and dried over $Na_2SO_4$ to give Methyl 4-cyano-2-fluorobenzoate (4.46 g, 95%). This Methyl ester (1.03 g, 5.77 mmol) was combined with methanol (60 mL) and Raney Ni (2 spatula tip fulls were added after washing with methanol under argon). It was then put under Hydrogen at 50 PSI on a PARR shaker for 18 hrs. The reaction was filtered through celite and washed with methanol while being kept under $N_2$. It was then purified by silica gel chromatography with methanol and methylene chloride to give methyl 4-(aminomethyl)-2-fluorobenzoate (247.6 mg, 23%) as off-white solid.

To a mixture of methyl 4-(aminomethyl)-2-fluorobenzoate (106.9 mg, 0.584 mmol) in N,N-dimethyl formamide (4.0 mL) was added 1,1'-carbonyldiimidazole (Aldrich, 98.9 mg, 0.592 mmol). After it was stirred at rt overnight under an argon atmosphere, the reaction mixture was extracted with EtOAc, and washed with water (2×), and saturated NaCl. The organic phase was separated, dried over $Na_2SO_4$, filtered and concentrated to give 2-Fluoro-4-{[(imidazole-1-carbonyl)-amino]-methyl}-benzoic acid methyl ester (187.0 mg) which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (48.8 mg, 0.115 mmol) and 2-Fluoro-4-{[(imidazole-1-carbonyl)-amino]-methyl}-benzoic acid methyl ester (183.3 mg, 0.764 mmol) in $CH_2Cl_2$ (8 mL) was stirred rt for 16 hrs. The reaction mixture was then purified by flash column to give 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]amino}-methyl)-2-fluoro-benzoic acid methyl ester (64.5 mg, 88%).

HRMS (ES$^+$) m/z Calcd $C_{32}H_{30}Cl_2F_3N_3O_3$+H (M+H): 632.1689; Found: 632.1686

Example 96

Preparation of rac 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]amino}-methyl)-2-fluoro-benzoic acid

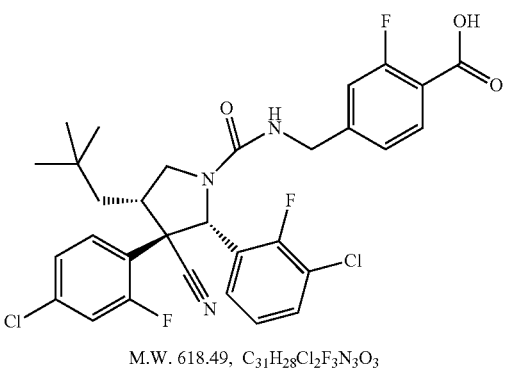

M.W. 618.49, $C_{31}H_{28}Cl_2F_3N_3O_3$

To a mixture of rac-4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]amino}-methyl)-2-fluoro-benzoic acid methyl ester (53.0 mg, 0.0838 mmol) in THF (6 mL) was added a solution of LiOH.H2O (Aldrich, 26 mg, 0.615 mmol) in water (3 mL) and the reaction mixture was stirred at rt overnight. The reaction mixture was partly concentrated and quenched with 1 N HCl (pH 5), extracted with EtOAc, and washed with water, saturated NaCl. The organic phase was separated, and dried over $Na_2SO_4$. The mixture was then concentrated to give rac-4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid (38.9 mg, 75%). HRMS (ES$^+$) m/z Calcd $C_{31}H_{28}Cl_2F_3N_3O_3$+H (M+H): 618.1533; Found: 618.1532

Example 97

Preparation of chiral 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid and chiral 4-({[(2R,3R,4R)-2-(3-Chloro-2-fluoro-phenyl)-3-(4-chloro-2-fluoro-phenyl)-3-cyano-4-(2,2-dimethyl-propyl)-pyrrolidine-1-carbonyl]amino}-methyl)-2-fluoro-benzoic acid

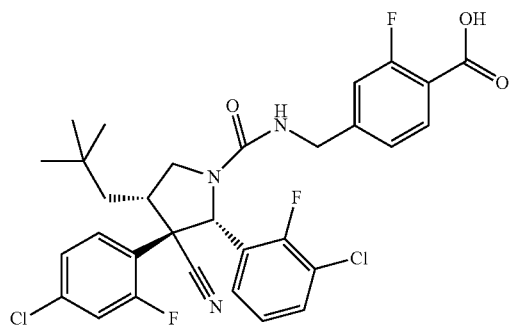

-continued

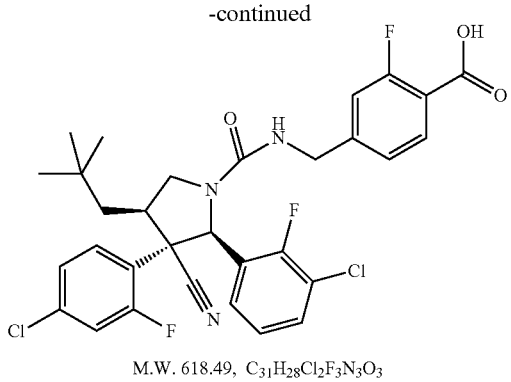

M.W. 618.49, $C_{31}H_{28}Cl_2F_3N_3O_3$

The mixture of rac-4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]amino}-methyl)-2-fluoro-benzoic acid was separated by SFC, 25% $CH_3OH$ on a Diacel AD prep column to give chiral chiral-4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]amino}-methyl)-2-fluoro-benzoic acid as a white lyophilized solid. MS (ES$^+$) m/z Calcd: [(M+H)$^+$]: 617.15, found: 617.2 and chiral 4-({[(2R,3R,4R)-2-(3-Chloro-2-fluoro-phenyl)-3-(4-chloro-2-fluoro-phenyl)-3-cyano-4-(2,2-dimethyl-propyl)-pyrrolidine-1-carbonyl]amino}-methyl)-2-fluoro-benzoic acid as a white lyophilized solid. MS (ES$^+$) m/z Calcd: [(M+H)$^+$]: 617.15, found: 617.2

Example 98

4-{[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-2-methyl-benzoic acid

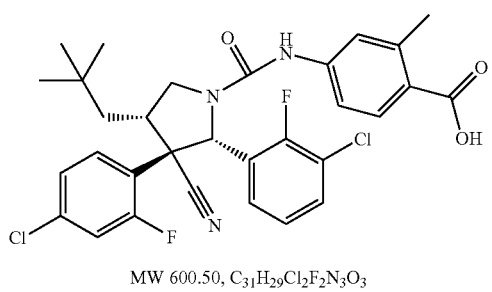

MW 600.50, $C_{31}H_{29}Cl_2F_2N_3O_3$

To a mixture of methyl 4-amino-2-methylbenzoate (208.9 mg, 1.230 mmol) in N,N-dimethyl formamide (5 mL) was added 1,1'-carbonyldiimidazole (Aldrich, 215 mg, 1.29 mmol). After it was stirred at rt overnight under an argon atmosphere, the reaction mixture was extracted with EtOAc, and washed with water (2×), and saturated NaCl. The organic phase was separated, dried over $Na_2SO_4$, filtered and concentrated to give 4-[(Imidazole-1-carbonyl)-amino]-2-methyl-benzoic acid methyl ester (342.0 mg) which was used without further purification.

A mixture of rac-(2S,3S,4S)-2-(3-chloro-2-fluoro-phenyl)-3-(4-chloro-2-fluoro-phenyl)-4-(2,2-dimethyl-propyl)-pyrrolidine-3-carbonitrile (49.5 mg, 0.117 mmol) and 4-[(Imidazole-1-carbonyl)-amino]-2-methyl-benzoic acid methyl ester (342.4 mg, 1.32 mmol) in $CH_2Cl_2$ (8 mL) was stirred rt for 16 hrs. The reaction mixture was then purified by flash column to give 4-{[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]amino}-2-methyl-benzoic acid methyl ester (63.2 mg, 88%).

This methyl ester (61.0 mg, 0.099 mmol) in THF (6 mL) was added a solution of LiOH.H2O (Aldrich, 30 mg, 0.717 mmol) in water (3 mL) and the reaction mixture was stirred at rt overnight. The reaction mixture was partly concentrated and quenched with 1 N HCl (pH 5), extracted with EtOAc, and washed with water, saturated NaCl. The organic phase was separated, and dried over $Na_2SO_4$. The mixture was then concentrated to give rac-4-{[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-2-methyl-benzoic acid (39 mg, 66%). HRMS (ES$^+$) m/z Calcd $C_3$, $H_{29}Cl_2F_2N_3O_3$+H [(M+H): 600.1627; Found: 600.1626

Example 99

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing:90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

Activity data for some of the Example compounds expressed as IC$_{50}$:bsa:0.02% are as follows:

| Example Number | IC$_{50}$: bsa: 0.02% |
| --- | --- |
| 4 | 0.269 |
| 12 | 0.644 |
| 16 | 3.228 |
| 41 | 0.869 |
| 48 | 1.734 |

What is claimed:
1. A compound of the formula

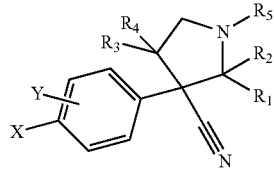

wherein
X is selected from the group consisting of H, F, Cl, Br, I, cyano, nitro, ethynyl, cyclopropyl, methyl, ethyl, isopropyl, vinyl and methoxy,
Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, heteroaryl, heterocycle, COOR', OCOR', CONR'R", NR'COR", NR"SO$_2$R', SO$_2$NR'R" and NR'R" wherein
R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle
and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, one of $R_1$ and $R_2$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen
one of $R_3$ and $R_4$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen,
$R_5$ is selected from the group consisting of lower alkyl, substituted lower alkyl, —CH$_2$(CH$_2$)$_n$—CHOH—R', —CH$_2$(CH$_2$)$_n$—CHOH—CH$_2$—(CH$_2$)$_n$—NR'R", CH$_2$(CH$_2$)$_n$—CO(CH$_2$)$_n$NR'R", CO(CH$_2$)$_n$—R', —CO(CH$_2$)$_n$—NR'—(CH$_2$)$_n$—CHOH—R', —CO(CH$_2$)$_n$—NR'R", (CH$_2$)$_n$—NR'SO$_2$R", —COCH$_2$(CH$_2$)$_n$—COOH, (CH$_2$)$_n$—COOR', (CH$_2$)$_n$—CONR'R", —CO(CH$_2$)$_n$—OR', —COCH$_2$(CH$_2$)$_n$—SR', —COCH$_2$(CH$_2$)$_n$—SOR', —COCH$_2$(CH$_2$)$_n$—SO$_2$R', —COCH$_2$(CH$_2$)$_n$—COR', —COCH$_2$(CH$_2$)$_n$—SO$_3$H, —COCH$_2$(CH$_2$)$_n$—SONR'R", —COCH$_2$(CH$_2$)$_n$—SO$_2$NR'R", —COCH$_2$(CH$_2$CH$_2$O)$_m$—(CH$_2$)$_n$—R', —COCH$_2$(CH$_2$CH$_2$O)$_m$—(CH$_2$)$_n$—OH, —COCH$_2$(CH$_2$CH$_2$O)$_m$—(CH$_2$)$_n$—OR', —COCH$_2$(CH$_2$CH$_2$O)$_m$—(CH$_2$)$_n$—NR'R", —COCH$_2$(CH$_2$CH$_2$O)$_m$—(CH$_2$)$_n$—NR'COR", —COCH$_2$(CH$_2$CH$_2$O)$_m$—(CH$_2$)$_n$—NR'SO$_2$R", —COCH$_2$(CH$_2$CH$_2$O)$_m$—(CH$_2$)$_n$—COOH, —COCH$_2$(CH$_2$CH$_2$O)$_m$—(CH$_2$)$_n$—COOR', —COCH$_2$(CH$_2$CH$_2$O)$_m$—(CH$_2$)$_n$—CONR'R", —COCH$_2$(CH$_2$CH$_2$O)$_m$—(CH$_2$)$_n$—SO$_2$R', —COCH$_2$(CH$_2$CH$_2$O)$_m$—(CH$_2$)$_n$—COR', —COCH$_2$(CH$_2$CH$_2$O)$_m$—(CH$_2$)$_n$—SONR'R", —COCH$_2$(CH$_2$CH$_2$O)$_m$—(CH$_2$)$_n$—SO$_2$NR'R", —COCH$_2$(CH$_2$)$_p$—(CH$_2$CH$_2$O)$_m$—(CH$_2$)$_n$—R', —COCH$_2$(CH$_2$)$_p$—(CH$_2$CH$_2$O)$_m$—(CH$_2$)$_n$—OH, —COCH$_2$(CH$_2$)$_p$—(CH$_2$CH$_2$O)$_m$—(CH$_2$)$_n$—OR', —COCH$_2$(CH$_2$)$_p$—(CH$_2$CH$_2$O)$_m$—(CH$_2$)$_n$—NR'R", —COCH$_2$(CH$_2$)$_p$—(CH$_2$CH$_2$O)$_m$—(CH$_2$)$_n$—NR'COR", —COCH$_2$(CH$_2$)$_p$—(CH$_2$CH$_2$O)$_m$—(CH$_2$)$_n$—NR'SO$_2$R", —COCH$_2$(CH$_2$)$_p$—(CH$_2$CH$_2$O)$_m$—(CH$_2$)$_n$—COOH, —COCH$_2$(CH$_2$)$_p$—(CH$_2$CH$_2$O)$_m$—(CH$_2$)$_n$—COOR', —COCH$_2$(CH$_2$)$_p$—(CH$_2$CH$_2$O)$_m$—(CH$_2$)$_n$—CONR'R", —COCH$_2$(CH$_2$)$_p$—(CH$_2$CH$_2$O)$_m$—(CH$_2$)$_n$—SO$_2$R', —COCH$_2$(CH$_2$)$_p$—(CH$_2$CH$_2$O)$_m$—(CH$_2$)$_n$—COR', —COCH$_2$(CH$_2$)$_p$—(CH$_2$CH$_2$O)$_m$—(CH$_2$)$_n$—SONR'R", —COCH$_2$(CH$_2$)$_p$—(CH$_2$CH$_2$O)$_m$—(CH$_2$)$_n$—SO$_2$NR'R", —COCH$_2$—COR', —COCH$_2$—SOR' and —COCH$_2$SO$_2$R' wherein R' and R" are as above,
m, n, and p are independently 0 to 6,
or a pharmaceutically acceptable salt or ester or enantiomer thereof.
2. A compound of claim 1 of the formula

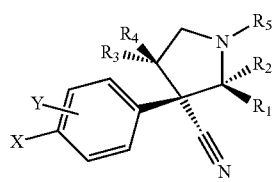

wherein
X is selected from the group consisting of F, Cl and Br,
Y is one to two group(s) independently selected from the group consisting of H, F, Cl, Br, I, CN, OH, nitro, lower alkyl, cycloalkyl and lower alkoxy,
$R_1$ is hydrogen,
one of $R_2$ and $R_3$ is selected from aryl, substituted aryl, heteroaryl or substituted heteroaryl and the other is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl,
$R_4$ is hydrogen,
$R_5$ is selected from the group consisting of lower alkyl, substituted lower alkyl, —CH$_2$(CH$_2$)$_n$—CHOH—R', —CH$_2$(CH$_2$)$_n$—CHOH—CH$_2$—(CH$_2$)$_n$—NR'R", CH$_2$(CH$_2$)$_n$—CO(CH$_2$)$_n$NR'R", CO(CH$_2$)$_n$—R', —CO(CH$_2$)$_n$—NR'—(CH$_2$)$_n$—CHOH—R', —CO(CH$_2$)$_n$—NR'R", (CH$_2$)$_n$—NR'SO$_2$R", —COCH$_2$(CH$_2$)$_n$—COOH, (CH$_2$)$_n$—COOR', (CH$_2$)$_n$—CONR'R", —CO(CH$_2$)$_n$—OR', —COCH$_2$(CH$_2$)$_n$—SR', —COCH$_2$(CH$_2$)$_n$—SOR', —COCH$_2$(CH$_2$)$_n$—SO$_2$R', —COCH$_2$(CH$_2$)$_n$—COR', —COCH$_2$(CH$_2$)$_n$—SO$_3$H, —COCH$_2$(CH$_2$)$_n$—SONR'R", —COCH$_2$(CH$_2$)$_n$—SO$_2$NR'R", —COCH$_2$(CH$_2$CH$_2$O)$_m$—(CH$_2$)$_n$—R', —COCH$_2$(CH$_2$CH$_2$O)$_m$—(CH$_2$)$_n$—OH, —COCH$_2$(CH$_2$CH$_2$O)$_m$—(CH$_2$)$_n$—OR', —COCH$_2$(CH$_2$CH$_2$O)$_m$—(CH$_2$)$_n$—NR'R", —COCH$_2$(CH$_2$CH$_2$O)$_m$—(CH$_2$)$_n$—NR'COR", —COCH$_2$(CH$_2$CH$_2$O)$_m$—(CH$_2$)$_n$—NR'SO$_2$R", —COCH$_2$(CH$_2$CH$_2$O)$_m$—(CH$_2$)$_n$—COOH, —COCH$_2$(CH$_2$CH$_2$O)$_m$—(CH$_2$)$_n$—COOR', —COCH$_2$(CH$_2$CH$_2$O)$_m$—(CH$_2$)$_n$—CONR'R", —COCH$_2$(CH$_2$CH$_2$O)$_m$—(CH$_2$)$_n$—SO$_2$R', —COCH$_2$(CH$_2$CH$_2$O)$_m$—(CH$_2$)$_n$—COR', —COCH$_2$(CH$_2$CH$_2$O)$_m$—(CH$_2$)$_n$—SONR'R", —COCH$_2$(CH$_2$CH$_2$O)$_m$—(CH$_2$)$_n$—SO$_2$NR'R", —COCH$_2$(CH$_2$)$_p$—(CH$_2$CH$_2$O)$_m$—(CH$_2$)$_n$—R', —COCH$_2$ (CH$_2$)$_p$— (CH$_2$CH$_2$O)$_m$—(CH$_2$)$_n$—OH, —COCH$_2$(CH$_2$)$_p$—(CH$_2$CH$_2$O)$_m$—(CH$_2$)$_n$—OR', —COCH$_2$(CH$_2$)$_p$—(CH$_2$CH$_2$O)$_m$—(CH$_2$)$_n$—NR'R", —COCH$_2$(CH$_2$)$_p$—(CH$_2$CH$_2$O)$_m$—(CH$_2$)$_n$—NR'COR", —COCH$_2$(CH$_2$)$_p$—(CH$_2$CH$_2$O)$_m$—(CH$_2$)$_n$—NR'SO$_2$R", —COCH$_2$(CH$_2$)$_p$—(CH$_2$CH$_2$O)$_n$—(CH$_2$)$_n$—COOH, —COCH$_2$(CH$_2$)$_p$—(CH$_2$CH$_2$O)$_m$—(CH$_2$)$_n$—COOR', —COCH$_2$(CH$_2$)$_p$—(CH$_2$CH$_2$O)$_m$—(CH$_2$)$_n$—CONR'R", —COCH$_2$(CH$_2$)$_p$—(CH$_2$CH$_2$O)$_m$—(CH$_2$)$_n$—SO$_2$R', —COCH$_2$(CH$_2$)$_p$—(CH$_2$CH$_2$O)$_m$—(CH$_2$)$_n$—COR', —COCH$_2$(CH$_2$)$_p$—(CH$_2$CH$_2$O)$_m$—(CH$_2$)$_n$—SONR'R", —COCH$_2$(CH$_2$)$_p$—(CH$_2$CH$_2$O)$_m$—(CH$_2$)$_n$—SO$_2$NR'R", —COCH$_2$—COR', —COCH$_2$—SOR' and —COCH$_2$SO$_2$R'

R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, m, n, and p are independently 0 to 6 or a pharmaceutically acceptable salt or ester or enantiomer thereof.

3. The compound of claim 2 of the formula

IB wherein

X is F, Cl or Br

Y is a mono substituting group selected from H and F

Z is F, Cl or Br,

W is H, F or Cl

R$_1$ is H

R$_4$ is H

R$_5$ is selected from the group consisting of lower alkyl, substituted lower alkyl, —CH$_2$(CH$_2$)$_n$—CHOH—R', —CH$_2$(CH$_2$)$_n$—CHOH—CH$_2$—(CH$_2$)$_n$—NR'R", CH$_2$(CH$_2$)$_n$—CO(CH$_2$)$_n$NR'R", CO(CH$_2$)$_n$—R', —CO(CH$_2$)$_n$—NR'—(CH$_2$)$_n$—CHOH—R', —CO(CH$_2$)$_n$—NR'R", (CH$_2$)$_n$—NR'SO$_2$R", —COCH$_2$(CH$_2$)$_n$—COOH, (CH$_2$)$_n$—COOR', (CH$_2$)$_n$—CONR'R", —CO(CH$_2$)$_n$—OR', —COCH$_2$(CH$_2$)$_n$—SR', —COCH$_2$(CH$_2$)$_n$—SOR', —COCH$_2$(CH$_2$)$_n$—SO$_2$R', —COCH$_2$(CH$_2$)$_n$—COR', —COCH$_2$(CH$_2$)$_n$—SO$_3$H, —COCH$_2$(CH$_2$)$_n$—SONR'R", —COCH$_2$(CH$_2$)$_n$—SO$_2$NR'R", —COCH$_2$(CH$_2$CH$_2$O)$_m$—(CH$_2$)$_n$—R', —COCH$_2$(CH$_2$CH$_2$O)$_m$—(CH$_2$)$_n$—OH, —COCH$_2$(CH$_2$CH$_2$O)$_m$—(CH$_2$)$_n$—OR', —COCH$_2$(CH$_2$CH$_2$O)$_m$—(CH$_2$)$_n$—NR'R", —COCH$_2$(CH$_2$CH$_2$O)$_m$—(CH$_2$)$_n$—NR'COR", —COCH$_2$(CH$_2$CH$_2$O)$_m$—(CH$_2$)$_n$—NR'SO$_2$R", —COCH$_2$(CH$_2$CH$_2$O)$_m$—(CH$_2$)$_n$—COOH, —COCH$_2$(CH$_2$CH$_2$O)$_m$—(CH$_2$)$_n$—COOR', —COCH$_2$(CH$_2$CH$_2$O)$_m$—(CH$_2$)$_n$—CONR'R", —COCH$_2$(CH$_2$CH$_2$O)$_m$—(CH$_2$)$_n$—SO$_2$R', —COCH$_2$(CH$_2$CH$_2$O)$_m$—(CH$_2$)$_n$—COR', —COCH$_2$(CH$_2$CH$_2$O)$_m$—(CH$_2$)$_n$—SONR'R", —COCH$_2$(CH$_2$CH$_2$O)$_m$—(CH$_2$)$_n$—SO$_2$NR'R", —COCH$_2$(CH$_2$)$_p$—(CH$_2$CH$_2$O)$_m$—(CH$_2$)$_n$—R', —COCH$_2$(CH$_2$)$_p$— (CH$_2$CH$_2$O)$_m$—(CH$_2$)$_n$—OH, —COCH$_2$(CH$_2$)$_p$—(CH$_2$CH$_2$O)$_m$—(CH$_2$)$_n$—OR', —COCH$_2$(CH$_2$)$_p$—(CH$_2$CH$_2$O)$_m$—(CH$_2$)$_n$—NR'R", —COCH$_2$(CH$_2$)$_p$—(CH$_2$CH$_2$O)$_m$—(CH$_2$)$_n$—NR'COR", —COCH$_2$(CH$_2$)$_p$—(CH$_2$CH$_2$O)$_m$—(CH$_2$)$_n$—NR'SO$_2$R", —COCH$_2$(CH$_2$)$_p$—(CH$_2$CH$_2$O)$_m$—(CH$_2$)$_n$—COOH, —COCH$_2$(CH$_2$)$_p$—(CH$_2$CH$_2$O)$_m$—(CH$_2$)$_n$—COOR', —COCH$_2$(CH$_2$)$_p$—(CH$_2$CH$_2$O)$_m$—(CH$_2$)$_n$—CONR'R", —COCH$_2$(CH$_2$)$_p$—(CH$_2$CH$_2$O)$_m$—(CH$_2$)$_n$—SO$_2$R', —COCH$_2$(CH$_2$)$_p$—(CH$_2$CH$_2$O)$_m$—(CH$_2$)$_n$—COR', —COCH$_2$(CH$_2$)$_p$—(CH$_2$CH$_2$O)$_m$—(CH$_2$)$_n$—SONR'R", —COCH$_2$(CH$_2$)$_p$—(CH$_2$CH$_2$O)$_m$—(CH$_2$)$_n$—SO$_2$NR'R", —COCH$_2$—COR', —COCH$_2$—SOR' and —COCH$_2$SO$_2$R', R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, m, n, and p are independently 0 to 6, R$_6$, R$_7$ are both methyl, or linked to form cyclopropyl, cyclobutyl, cyclopentyl or cyclohexyl, R$_8$ is (CH$_2$)$_q$—R$_9$, q is 0, 1 or 2

R$_9$ is selected from hydrogen, hydroxyl, lower alkyl, lower alkoxy, lower cycloalkyl, aryl, substituted aryl, heteroaryl, substituted heteroaryl, heterocycle or substituted heterocycle, or a pharmaceutically acceptable salt or ester or enantiomer thereof.

4. The compound of claim 2 having the formula

IC wherein

X is F, Cl or Br,

Y is a mono substituting group selected from H and F

Z is F, Cl or Br,

W is H or F,

R$_1$ is H,

R$_4$ is H,

R$_5$ is selected from the group consisting of —CO(CH$_2$)$_n$—R', —CO(CH$_2$)$_n$—NR'R", (CH$_2$)$_n$—CONR'R", —CH$_2$(CH$_2$)$_n$—CHOH—R', —CH$_2$(CH$_2$)$_n$—CHOH—CH$_2$—(CH$_2$)$_n$—NR'R", CH$_2$(CH$_2$)$_n$—CO(CH$_2$)$_n$ NR'R", CO(CH$_2$)$_n$—R', —CO(CH$_2$)$_n$—NR'—(CH$_2$)$_n$—CHOH—R', and —CO(CH$_2$)$_n$—NR'R", n is 0, 1 or 2, R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle, and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, R$_6$, R$_7$ are both methyl, or linked to form cyclopropyl, cyclobutyl, cyclopentyl or cyclohexyl, R$_8$ is (CH$_2$)$_q$—R$_9$, q is 0, 1 or 2

R$_9$ is selected from hydrogen, hydroxyl, lower alkyl, lower alkoxy, cycloalkyl, aryl, substituted aryl, heteroaryl, substituted heteroaryl, heterocycle or substituted heterocycle, or a pharmaceutically acceptable salt or ester thereof.

5. A compound of claim 1 selected from the group consisting of rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide, (2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide, rac-(2S,3S,4S)-2-(3-chloro-phenyl)-3-(4-chloro-2-fluoro-phenyl)-3-cyano-4-(2,2-dimethyl-propyl)-pyrrolidine-1-carboxylic acid ((S)-3,4-dihydroxy-butyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid [1-(2-hydroxy-2-methyl-propyl)-1H-pyrazol-3-yl]-amide, rac-(2S,3S,4S)-2-(3-chloro-2-fluoro-phenyl)-3-(4-chloro-2-fluoro-phenyl)-4-(2,2-dimethyl-propyl)-1-(4-ethyl-piperazine-1-carbonyl)-pyrrolidine-3-carbonitrile, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (piperidin-4-ylmethyl)-amide, rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)benzoic acid, 4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)benzoic acid, rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid, 4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid and rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid.

6. A compound of claim 1 selected from the group consisting of rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid, rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzoic acid, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-chloro-phenyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-fluoro-phenyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid 4-chloro-benzylamide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid [3-(1H-tetrazol-5-yl)-phenyl]-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-cyano-phenyl)-amide, rac-(2S,3S,4S)-2-(3-chloro-2-fluoro-phenyl)-3-(4-chloro-2-fluoro-phenyl)-1-(4-cyano-benzoyl)-4-(2,2-dimethyl-propyl)-pyrrolidine-3-carbonitrile, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-carbamoyl-phenyl)-amide, rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-benzamide and rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-2-oxo-ethyl}-2-ethoxy-benzoic acid.

7. A compound of claim 1 selected from the group consisting of rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-4-oxo-butyl}-benzoic acid, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid 4-fluoro-benzylamide, rac-4-{4-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propenyl}-benzoic acid, rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-3-oxo-propionic acid, rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid tert-butyl ester, rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid, rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid methyl ester, rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzoic acid, rac-4-{2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetylamino}-benzamide, rac-2-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-N—((S)-3,4-dihydroxy-butyl)-acetamide and rac-(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carboxylic acid ((S)-3,4-dihydroxy-butyl)-amide.

8. A compound of claim 1 selected from the group consisting of rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl]-amino}-benzoic acid ethyl ester, rac-4-{[(2S,3R,4S)-4-(3-chloro-2-fluoro-phenyl)-3-(4-chloro-2-fluoro-phenyl)-3-cyano-2-(2,2-dimethyl-propyl)-pyrrolidine-1-carbonyl]-amino}-benzoic acid, rac-[(2S,3R,4S)-4-(3-chloro-2-fluoro-phenyl)-3-(4-chloro-2-fluoro-phenyl)-3-cyano-2-(2,2-dimethyl-propyl)-pyrrolidin-1-yl]-acetic acid, rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-benzoic acid methyl ester, rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-benzoic acid, rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid methyl ester, rac-4-{2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetylamino}-methyl-benzoic acid, rac-2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-N—((S)-3,4-dihydroxy-butyl)-acetamide, rac-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid ethyl ester, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid pyridin-4-ylamide and rac-2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid methyl ester.

9. A compound of claim 1 selected from the group consisting of rac-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetic acid, 2-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-benzoic acid, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (4-fluoro-phenyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methylsulfanyl-phenyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methanesulfonyl-phenyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid pyridin-3-ylamide, rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid ethyl ester, rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-butyric acid, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-carbamoyl-propyl)-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (3-methylcarbamoyl-propyl)-amide and rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (1-methanesulfonyl-piperidin-4-yl)-amide.

10. A compound of claim 1 selected from the group consisting of rac-2-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-acetamide, rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid ethyl ester, rac-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-acetic acid, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid methylcarbamoylmethyl-amide, rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid carbamoylmethyl-amide, rac-(2S,3S,4S)-2-(3-chloro-2-fluoro-phenyl)-3-(4-chloro-2-fluoro-phenyl)-4-(2,2-dimethyl-propyl)-1-(pyridine-3-sulfonyl)-pyrrolidine-3-carbonitrile, rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)cyclohexanecarboxylic acid methyl ester, rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)cyclohexanecarboxylic acid, rac-(2S,3S,4S)-2-(3-chloro-2-fluoro-phenyl)-3-(4-chloro-2-fluoro-phenyl)-4-(2,2-dimethyl-propyl)-1-(6-morpholin-4-yl-pyridine-3-sulfonyl)-pyrrolidine-3-carbonitrile, rac-4-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-2-methoxy-benzoic acid methyl ester and rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-cyclohexanecarboxylic acid.

11. A compound of claim 1 selected from the group consisting of rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid ethyl ester, rac-3-{[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-propionic acid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-methylcarbamoyl-ethyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-dimethylcarbamoyl-ethyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (2-carbamoyl-ethyl)-amide,
rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid ethyl ester,
rac-{1-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-piperidin-4-yl}-acetic acid,
rac-3-[(2S,3S,4S)-2-(3-chloro-2-fluoro-phenyl)-3-(4-chloro-2-fluoro-phenyl)-3-cyano-4-(2,2-dimethyl-propyl)-pyrrolidin-1-yl]-propionic acid,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (6-chloro-pyridin-3-ylmethyl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (6-chloro-pyridin-3-yl)-amide,
rac-(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid (1-methyl-2-oxo-1,2-dihydro-pyridin-4-yl)-amide and
rac-4-[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-sulfonyl]-benzoic acid.

12. A compound of claim 1 selected from the group consisting of
rac-(2S,3S,4S)-2-(3-chloro-2-fluoro-phenyl)-3-(4-chloro-2-fluoro-phenyl)-1-(6-chloro-pyridine-3-sulfonyl)-4-(2,2-dimethyl-propyl)-pyrrolidine-3-carbonitrile,
rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-sulfonyl)-pyrrolidine-3-carbonitrile,
rac-(2S,3S,4S)-2-(3-chloro-2-fluoro-phenyl)-3-(4-chloro-2-fluoro-phenyl)-1-(6-chloro-pyridine-3-carbonyl)-4-(2,2-dimethyl-propyl)-pyrrolidine-3-carbonitrile,
rac-(2S,3S,4S)-2-(3-chloro-2-fluoro-phenyl)-3-(4-chloro-2-fluoro-phenyl)-4-(2,2-dimethyl-propyl)-1-(6-oxo-1,6-dihydro-pyridine-3-carbonyl)-pyrrolidine-3-carbonitrile,
rac-(2S,3S,4S)-2-(3-chloro-2-fluoro-phenyl)-3-(4-chloro-2-fluoro-phenyl)-4-(2,2-dimethyl-propyl)-1-(1-methyl-6-oxo-1,6-dihydro-pyridine-3-carbonyl)-pyrrolidine-3-carbonitrile,
rac-4-({[(2S,3S,4S)-2-(3-chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid methyl ester,
rac-4-(((2S,3S,4S)-2-(3-chloro-2-fluorophenyl)-3-(4-chloro-2-fluorophenyl)-3-cyano-4-neopentylpyrrolidine-1-carboxamido)methyl)-2-methoxybenzoic acid,
rac-(2R,3S,4S)-2-(3-chloro-2-fluoro-phenyl)-3-(4-chloro-2-fluoro-phenyl)-3-cyano-4-(2,2-dimethyl-propyl)-pyrrolidine-1-carboxylic acid benzylamide,
rac N-[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-benzamide,
chiral 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid,
chiral 4-({[(2R,3R,4R)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-methoxy-benzoic acid,
4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid methyl ester,
rac 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid,
chiral 4-({[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid,
chiral 4-({[(2R,3R,4R)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-methyl)-2-fluoro-benzoic acid and
4-{[(2S,3S,4S)-2-(3-Chloro-2-fluoro-phenyl)-3-(4-chloro-2-fluoro-phenyl)-3-cyano-4-(2,2-dimethyl-propyl)-pyrrolidine-1-carbonyl]-amino}-2-methyl-benzoic acid.

13. A pharmaceutical formulation comprising a compound of the formula

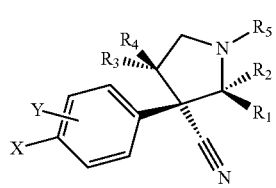

IA wherein
X is selected from the group consisting of F, Cl and Br,
Y is one to two group(s) independently selected from the group consisting of H, F, Cl, Br, I, CN, OH, nitro, lower alkyl, cycloalkyl and lower alkoxy,
$R_1$ is hydrogen,
one of $R_2$ and $R_3$ is selected from aryl, substituted aryl, heteroaryl or substituted heteroaryl and the other is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl,
$R_4$ is hydrogen,
$R_5$ is selected from the group consisting of lower alkyl, substituted lower alkyl, —$CH_2(CH_2)_n$—CHOH—R', —$CH_2(CH_2)_n$—CHOH—$CH_2$—$(CH_2)_n$—NR'R", $CH_2$ $(CH_2)_n$—CO$(CH_2)_n$NR'R", CO$(CH_2)_n$—R', —CO $(CH_2)_n$—NR'—$(CH_2)_n$—CHOH—R', —CO$(CH_2)_n$— NR'R", $(CH_2)_n$—NR'SO$_2$R", —COCH$_2$(CH$_2$)$_n$— COOH, $(CH_2)_n$—COOR', $(CH_2)_n$—CONR'R", —CO $(CH_2)_n$—OR', —COCH$_2$(CH$_2$)$_n$—SR', —COCH$_2$ $(CH_2)_n$—SOR', —COCH$_2$(CH$_2$)$_n$—SO$_2$R', —COCH$_2$ $(CH_2)_n$—COR', —COCH$_2$(CH$_2$)$_n$—SO$_3$H, —COCH$_2$ $(CH_2)_n$—SONR'R", —COCH$_2$(CH$_2$)$_n$—SO$_2$NR'R", —COCH$_2$(CH$_2$CH$_2$O)$_m$—(CH$_2$)$_n$—R', —COCH$_2$ (CH$_2$CH$_2$O)$_m$—(CH$_2$)$_n$—OH, —COCH$_2$(CH$_2$CH$_2$O)$_m$ —(CH$_2$)$_n$—OR', —COCH$_2$(CH$_2$CH$_2$O)$_m$—(CH$_2$)$_n$— NR'R", —COCH$_2$(CH$_2$CH$_2$O)$_m$—(CH$_2$)$_n$—NR'COR", —COCH$_2$(CH$_2$CH$_2$O)$_m$—(CH$_2$)$_n$—NR'SO$_2$R", —COCH$_2$(CH$_2$CH$_2$O)$_m$—(CH$_2$)$_n$—COOH, —COCH$_2$ (CH$_2$CH$_2$O)$_m$—(CH$_2$)$_n$—COOR', —COCH$_2$ (CH$_2$CH$_2$O)$_m$—(CH$_2$)$_n$—CONR'R", —COCH$_2$ (CH$_2$CH$_2$O)$_m$—(CH$_2$)$_n$—SO$_2$R', —COCH$_2$ (CH$_2$CH$_2$O)$_m$—(CH$_2$)$_n$—COR', —COCH$_2$ (CH$_2$CH$_2$O)$_m$—(CH$_2$)$_n$—SONR'R", —COCH$_2$ (CH$_2$CH$_2$O)$_m$—(CH$_2$)$_n$—SO$_2$NR'R", —COCH$_2$ (CH$_2$)$_p$—(CH$_2$CH$_2$O)$_m$—(CH$_2$)$_n$—R', —COCH$_2$ (CH$_2$)$_p$—(CH$_2$CH$_2$O)$_m$—(CH$_2$)$_n$—OH, —COCH$_2$ (CH$_2$)$_p$—(CH$_2$CH$_2$O)$_m$—(CH$_2$)$_n$—OR', —COCH$_2$ (CH$_2$)$_p$—(CH$_2$CH$_2$O)$_m$—(CH$_2$)$_n$—NR'R", —COCH$_2$ (CH$_2$)$_p$—(CH$_2$CH$_2$O)$_m$—(CH$_2$)$_n$—NR'COR", —COCH$_2$(CH$_2$)$_p$—(CH$_2$CH$_2$O)$_m$—(CH$_2$)$_n$— NR'SO$_2$R", —COCH$_2$(CH$_2$)$_p$—(CH$_2$CH$_2$O)$_m$— (CH$_2$)$_n$—COOH, —COCH$_2$(CH$_2$)$_p$—(CH$_2$CH$_2$O)$_m$— (CH$_2$)$_n$—COOR', —COCH$_2$(CH$_2$)$_p$—(CH$_2$CH$_2$O)$_m$— (CH$_2$)$_n$—CONR'R", —COCH$_2$(CH$_2$)$_p$—(CH$_2$CH$_2$O)$_m$ —(CH$_2$)$_n$—SO$_2$R', —COCH$_2$(CH$_2$)$_p$—(CH$_2$CH$_2$O)$_m$ —(CH$_2$)$_n$—COR', —COCH$_2$(CH$_2$)$_p$—(CH$_2$CH$_2$O)$_m$— (CH$_2$)$_n$—SONR'R", —COCH$_2$(CH$_2$)$_p$—(CH$_2$CH$_2$O)$_m$ —(CH$_2$)$_n$—SO$_2$NR'R", —COCH$_2$—COR', —COCH$_2$—SOR' and —COCH$_2$SO$_2$R'

R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, heterocycle, or substituted heterocycle and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, m, n, and p are independently 0 to 6 or a pharmaceutically acceptable salt or ester or enantiomers thereof together with a pharmaceutically acceptable excipient and/or carrier.

\* \* \* \* \*